(12) United States Patent
Ben Oren et al.

(10) Patent No.: US 10,537,387 B2
(45) Date of Patent: *Jan. 21, 2020

(54) METHODS AND SYSTEMS FOR BLOCKING NEURAL ACTIVITY IN AN ORGAN OF A SUBJECT, PREFERABLY IN THE SMALL INTESTINE OR THE DUODENUM

(71) Applicant: DIGMA MEDICAL LTD., Petah Tikva (IL)

(72) Inventors: Ilan Ben Oren, Modiin (IL); Irit Yaniv, Ramat Gan (IL); Tamir Wolf, Tel Aviv (IL); Avia Herschkovitz, Rehovot (IL)

(73) Assignee: DIGMA MEDICAL LTD., Petah Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/303,080

(22) PCT Filed: Apr. 16, 2015

(86) PCT No.: PCT/IL2015/050410
§ 371 (c)(1),
(2) Date: Oct. 10, 2016

(87) PCT Pub. No.: WO2015/159296
PCT Pub. Date: Oct. 22, 2015

(65) Prior Publication Data
US 2017/0027645 A1    Feb. 2, 2017

Related U.S. Application Data

(60) Provisional application No. 62/030,641, filed on Jul. 30, 2014, provisional application No. 61/980,618, filed on Apr. 17, 2014.

(51) Int. Cl.
*A61B 18/20* (2006.01)
*A61B 18/00* (2006.01)
(Continued)

(52) U.S. Cl.
CPC ............ *A61B 18/22* (2013.01); *A61B 5/4255* (2013.01); *A61B 1/012* (2013.01); *A61B 5/0066* (2013.01);
(Continued)

(58) Field of Classification Search
CPC . A61N 5/0603; A61N 2005/063; A61B 18/22
(Continued)

(56) References Cited

U.S. PATENT DOCUMENTS 3,858,577 A    1/1975    Bass
5,029,574 A    8/1991    Shimamura
(Continued)

FOREIGN PATENT DOCUMENTS

EP    0288576    11/1988
WO    2004069331    8/2004
(Continued)

OTHER PUBLICATIONS

Cummings, et al., (2004) Gastric bypass for obesity: mechanisms of weight loss and diabetes resolution, J Clin Endocrinol Metab 89(6): 2608-2615.
(Continued)

*Primary Examiner* — Nathan J Jenness
(74) *Attorney, Agent, or Firm* — The Roy Gross Law Firm, LLC; Roy Gross

(57) ABSTRACT

The present disclosure provides, according to some embodiments, methods and systems for selectively reducing, blocking or inhibiting at least part of the neural activity in an organ of a subject. In preferred embodiments, the method and system are used for selectively blocking at least part of
(Continued)

the neural activity in a duodenum of a subject in need thereof. According to some embodiments, the selective blocking occurs through use of laser radiation. According to some embodiments, the selective blocking occurs through use of ultrasound energy. According to some embodiments, the selective blocking comprises causing damage to at least part of sensory nerves located within a target area while maintaining functional activity of tissue surrounding the sensory nerves by means of shielding it from the effects of laser radiation. According to some embodiments, the sensory nerves include neurons configured to transmit signals triggered by food passing through the duodenum, such as, but not limited to, neurohormonal signals.

9 Claims, 20 Drawing Sheets

(51) Int. Cl.
| | | |
|---|---|---|
| *A61B 5/00* | (2006.01) | |
| *A61B 18/22* | (2006.01) | |
| *A61B 8/08* | (2006.01) | |
| *A61B 8/12* | (2006.01) | |
| *A61B 1/012* | (2006.01) | |
| *A61B 5/026* | (2006.01) | |
| *A61B 5/055* | (2006.01) | |
| *A61B 5/107* | (2006.01) | |

(52) U.S. Cl.
CPC .............. *A61B 5/0086* (2013.01); *A61B 5/026* (2013.01); *A61B 5/055* (2013.01); *A61B 5/1076* (2013.01); *A61B 8/085* (2013.01); *A61B 8/12* (2013.01); *A61B 2018/00029* (2013.01); *A61B 2018/00285* (2013.01); *A61B 2018/00434* (2013.01); *A61B 2018/00494* (2013.01); *A61B 2018/00577* (2013.01); *A61B 2018/00589* (2013.01); *A61B 2018/00601* (2013.01); *A61B 2018/00702* (2013.01); *A61B 2018/00714* (2013.01); *A61B 2018/00744* (2013.01); *A61B 2018/00785* (2013.01); *A61B 2018/00904* (2013.01); *A61B 2018/00982* (2013.01); *A61B 2018/20355* (2017.05); *A61B 2018/2261* (2013.01); *A61B 2018/2266* (2013.01); *A61B 2018/2277* (2013.01); *A61B 2018/2283* (2013.01); *A61B 2218/001* (2013.01)

(58) Field of Classification Search
USPC ........................................................ 606/1–19
See application file for complete search history.

(56) References Cited

U.S. PATENT DOCUMENTS

| | | | |
|---|---|---|---|
| 5,693,043 | A | 12/1997 | Kittrell |
| 6,134,003 | A | 10/2000 | Boppart |
| 6,832,114 | B1 | 12/2004 | Whitehurst et al. |
| 6,914,733 | B2 | 7/2005 | Dong |
| 7,096,070 | B1 | 8/2006 | Jenkins |
| 7,363,076 | B2 | 4/2008 | Yun |
| 7,430,450 | B2 | 9/2008 | Imran |
| 7,494,661 | B2 | 2/2009 | Sanders |
| 7,582,081 | B2 | 9/2009 | Hofer |
| 7,620,455 | B2 | 11/2009 | Maschino |
| 7,835,074 | B2 | 11/2010 | Jacobsen |
| 8,095,218 | B2 | 1/2012 | Gross |
| 8,150,518 | B2 | 4/2012 | Levin |
| 8,340,760 | B2 | 12/2012 | Dobak, III |
| 8,568,399 | B2 | 10/2013 | Azamian |
| 2002/0183622 | A1 | 12/2002 | Zuluaga |
| 2003/0144708 | A1 | 7/2003 | Starkebaum |
| 2004/0082859 | A1 | 4/2004 | Schaer |
| 2004/0172088 | A1 | 9/2004 | Knudson |
| 2004/0215180 | A1 | 10/2004 | Starkebaum et al. |
| 2005/0183732 | A1 | 8/2005 | Edwards |
| 2006/0122584 | A1 | 6/2006 | Bommannan |
| 2007/0060906 | A1 | 3/2007 | Wu |
| 2007/0081236 | A1 | 4/2007 | Tearney |
| 2008/0086180 | A1 | 4/2008 | Ben-Ezra |
| 2008/0275445 | A1 | 11/2008 | Kelly |
| 2009/0030473 | A1 | 1/2009 | Khawaled |
| 2009/0062881 | A1 | 3/2009 | Gross |
| 2009/0086213 | A1 | 4/2009 | Masuda |
| 2009/0234417 | A1 | 9/2009 | Pastena |
| 2009/0253990 | A1 | 10/2009 | Lieber |
| 2010/0049188 | A1 | 2/2010 | Nelson |
| 2010/0114150 | A1 | 5/2010 | Magal |
| 2010/0268297 | A1 | 10/2010 | Neisz |
| 2010/0280504 | A1 | 11/2010 | Manzke |
| 2011/0130708 | A1 | 6/2011 | Perry |
| 2011/0208173 | A1 | 8/2011 | Sobotka |
| 2011/0208175 | A1 | 8/2011 | Sobotka |
| 2011/0257641 | A1 | 10/2011 | Hastings |
| 2012/0179228 | A1 | 7/2012 | Decharms |
| 2013/0197555 | A1 | 8/2013 | Schaer |
| 2013/0345670 | A1 | 12/2013 | Rajagopalan et al. |
| 2014/0017635 | A1 | 1/2014 | Fisher |
| 2014/0074077 | A1 | 3/2014 | Lane |
| 2014/0088575 | A1* | 3/2014 | Loeb ...................... A61B 18/24 606/7 |
| 2014/0088581 | A1 | 3/2014 | Kelly |
| 2014/0187619 | A1 | 7/2014 | Pasricha et al. |
| 2015/0148738 | A1 | 5/2015 | Caplan et al. |

FOREIGN PATENT DOCUMENTS

| | | |
|---|---|---|
| WO | 2004112883 | 12/2004 |
| WO | 2011156736 | 12/2011 |
| WO | 2012099974 | 7/2012 |
| WO | 2012122460 | 9/2012 |
| WO | 2013012892 | 1/2013 |
| WO | 2013082587 | 6/2013 |
| WO | 2013130655 | 9/2013 |
| WO | 2013159066 | 10/2013 |
| WO | 2014022436 | 2/2014 |
| WO | 2014026055 | 2/2014 |
| WO | 2014055997 | 4/2014 |
| WO | 2014197632 A2 | 12/2014 |
| WO | 2015159296 | 10/2015 |

OTHER PUBLICATIONS

Myslovich (2001) Stomach and duodenum ulcer: comparing the efficiency of three laser therapeutic techniques. Proc. SPIE 4422, Low-Level Laser Therapy, 74 (Apr. 26, 2001); doi: 101117/12. 425517.

Oraevsky, et al.(1996) Plasma Mediated Ablation of Biological Tissues with Nanosecond-to-Femtosecond Laser Pulses:Relative Role of Linear and Nonlinear Absorption, IEEE Journal of Selected Topics in Quantum Electronics, vol. 2, No. 4: 801-809.

Pories, W.J., et al. (2001) Etiology of types II diabetes mellitus: a role of the foregut, World J Surg (25(4): 572-31.

Rubino, et al, (2004) The early effects of the Roux-en-Y gastric bypass on hormones involved in body weight regulation and glucose metabolism, Annals of Surgery, vol. 240, No. 2: 236-42.

Rubino, et al, (2006) The Mechanism of Diabetes Control After Gastrointestinal Bypass Surgery Reveals a Role of the Proximal Small Intestine in the Pathophysiology of Type 2 Diabetes, The Annals of Surgery, vol. 244, No. 5: 741-9.

Verdam, F.J. at al. (2012), An Update on less invasive and encoscopic techniques mimicking the effect of bariatric surgery, J Obesity 2012: 597871.

Wikipedia (2012) Submucosa, Retrieved on Aug. 13, 2019, [https://en.wikipedia.org/wiki/Submucosa].

(56) References Cited

OTHER PUBLICATIONS

Dougherty, et al (1998) Photodynamic Therapy, J Natl Cancer Inst 90(12): 889-95.

* cited by examiner

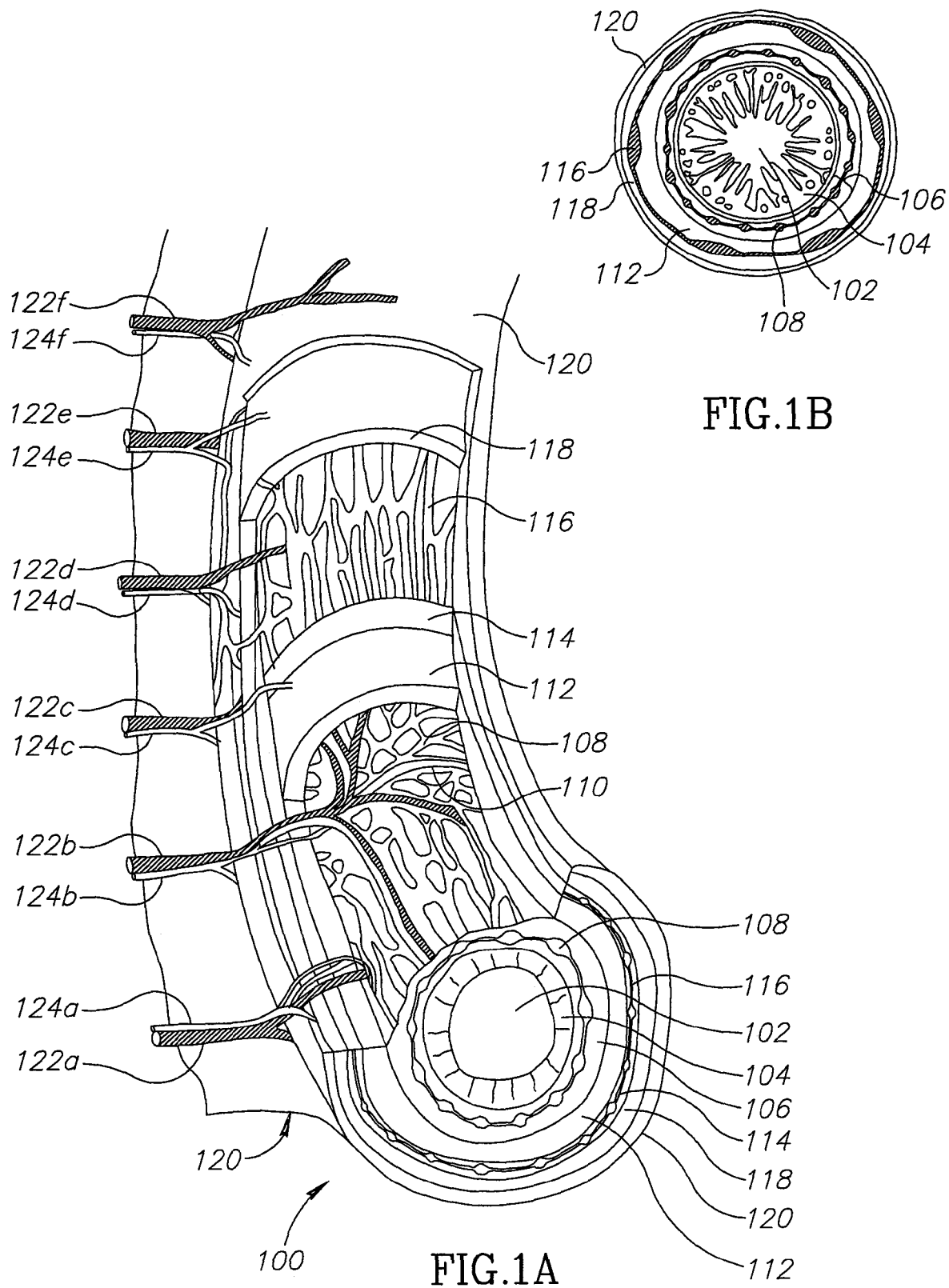

METHODS AND SYSTEMS FOR BLOCKING NEURAL ACTIVITY IN AN ORGAN OF A SUBJECT, PREFERABLY IN THE SMALL INTESTINE OR THE DUODENUM

This application is a 35 U.S.C. § 371 national phase application of PCT/IL2015/050410, filed Apr. 16, 2015, which claims priority to U.S. 61/980,618 filed on Apr. 17, 2014 and U.S. 62/030,641 filed Jul. 30, 2014. All applications are incorporated herein by reference as if fully set forth.

TECHNICAL FIELD

The present disclosure relates generally to methods and systems for selectively blocking part of the neural activity in a bodily organ. In preferred embodiments, the methods and systems are used for selectively blocking part of the neural activity in the small intestine, and preferably in the duodenum of a subject. In preferred embodiments, the invention is directed at endoluminal interventions that block, modulate and/or impact neurohormonal and other signals triggered by food passing through the gastrointestinal (GI) tract.

BACKGROUND

As opposed to Type 1 Diabetes mellitus, in which there is an absolute insulin deficiency due to destruction of islet cells in the pancreas, Type 2 Diabetes mellitus (T2D), formerly known as noninsulin-dependent diabetes mellitus (NIDDM) or adult-onset diabetes, is a metabolic disorder characterized by high blood glucose and a relative insulin deficiency due to insulin resistance. Type 2 diabetes constitutes about 90% of cases of diabetes worldwide and demonstrates an increasingly growing rate of prevalence. Type-2 diabetes is typically managed by changes in lifestyle, such as exercise and dietary modification, and in certain cases by medications and surgery.

Obesity is thought to be one of the primary causes of type 2 diabetes, especially in people who are genetically predisposed for the disease. Obesity is often treated by performing a bariatric surgery procedure (also known as weight-loss surgery) on the gastrointestinal tract of an obese patient in order to reduce weight. Multiple clinical studies and reports have indicated that in addition to weight-loss, certain bariatric surgery procedures can contribute to remission or improvement in disease management of type-2 diabetes, as well as to reduction in insulin resistance. This is specifically the case in certain bariatric procedures that bypass the proximal part of the gastrointestinal (GI) tract, such as Roux-en-Y gastric bypass (RYGB), duodenal-jejunal bypass (DJB) surgery and gastrojejunal bypass (GJB) surgery, all aimed at bypassing the duodenum. Unfortunately, bariatric surgery is associated with high risk and high cost and is not the optimal solution for management of the majority of T2D and non-obese patients, estimated at hundreds of millions worldwide. Thus, bariatric surgery is not used in the majority of T2D patients for disease management.

Previous attempts to obtain effects similar to bariatric surgery have included the use of minimally invasive devices, such as those inserted endoluminally. Such attempts have included use of staplers to reduce stomach size, insertion of devices into the stomach (most common of which is the intra-gastric balloon), implantation of electrical stimulators that intervene with stomach function (gastric electrical stimulation) via the modulation of gastric nerves activity, use of sleeves that bypass the duodenum such as the Endo-Barrier® (GI Dynamics™) and radio-frequency (RF) ablation applied to the surface of the organ in the gastrointestinal tract with non-penetrating electrodes, as described in US Patent Publication No. 2008/0275445 A1 assigned to BarrX, or in WO 2012099974 A2 assigned to Fractyl Laboratories, Inc., which targets duodenum mucosa, and ablation of the area around the pyloric sphincter as described in EP1567082 A1 to Curon.

Each of these methods, however, suffers from inherent limitations. For example, use of the EndoBarrier® is associated with adverse events and has unwarranted side effects, such as vomiting, nausea, abdominal pain, mucosal tear, bleeding, migration and obstruction, necessitating early device removal. (Verdam F J et al. Obesity 2012, Vol 2012-(2012), Article ID 597871, 10 pages). The use of staplers suffers from complications and failed to show the effectiveness of surgery. The use of intra-gastric balloons suffers from side effects, such as migration. The use of gastric electrical stimulation suffers from limited efficacy. Metabolic syndrome is a medical disorder, including comorbidity of at least three of the following medical conditions: abdominal (central) obesity, elevated blood pressure, elevated fasting plasma glucose, high serum triglycerides, and low high-density cholesterol (HDL) levels. Metabolic syndrome patients are of higher risk of medical condition deterioration. Several studies have shown a link between reduction of some neural activity, and the improvement of medical condition of these patients; other studies have shown an improvement of other metabolic syndrome conditions following improvement in diabetes of these patients.

Accordingly, it is desired to provide a novel solution for endoluminal interventions that will overcome the deficiencies of the prior art.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods that are meant to be exemplary and illustrative, not limiting in scope.

The present disclosure provides, according to some embodiments, methods and systems for selectively blocking, reducing or limiting part of the neural activity in a target area by directing laser radiation configured to cause damage to sensory neurons located within the target area. According to some embodiments, the target area is located in an organ in a subject's body. According to some embodiments, the target area is located in the small intestine or a wall of the duodenum.

According to some embodiments, the method and systems are for selectively blocking, reducing or limiting part of the neural activity within a duodenal wall or in contact with a duodenal wall in a subject. According to some embodiments, the methods and systems cause damage to sensory neurons in the target area, while maintaining functional activity of tissue surrounding the sensory neurons. According to some embodiments, the tissue surrounding the sensory neurons is not affected by the methods and systems, such that the methods and systems are localized only to sensory neurons in the target area. According to some embodiments, the tissue surrounding the sensory neurons is minimally affected by the methods and systems, such that it can recuperate post procedure, such that the long term effect of treatment is localized only to sensory neurons in the target area, and to non-important tissue substances such as connective tissue.

According to some embodiments, the sensory neurons are sensory neurons activated by passage of food through the duodenum. According to some embodiments, the sensory neurons are activated by signals received by mechano-sensors and/or chemo-receptors in at least one layer of the duodenal wall. Each possibility represents a separate embodiment of the present disclosure. According to some embodiments, the sensory neurons are neurons which deliver internal neural signals within the duodenum. According to other embodiments, the sensory neurons are neurons which deliver signals out of the duodenum through neurons such as, but not limited to, vagal nerves, sympathetic nerves and parasympathetic nerves.

According to some embodiments, the methods and systems block and/or modulate neurohormonal and other signals triggered by food passing through the GI tract while minimizing side effects by selective spatially localized interventions.

According to some embodiments, the methods and systems include laser radiation configured to specifically target at least one target area, the target area comprising sensory neurons. According to some embodiments, the target area may include one or both extrinsic and intrinsic neural pathways. According to some embodiments, the laser radiation is focused on a target area comprising sensory neurons such that tissue surrounding the target area maintains functional activity. According to a non-limiting example, pulsed laser radiation may be used and ablation may occur only within the target area on which the laser radiation is focused. According to some embodiments, the laser radiation is focused on a target area such that only neurons within the target area are damaged, while non-neural tissues within the target area maintain functional activity. According to some embodiments, the laser radiation is focused at an intensity and/or duration such that it induces thermal damage in neural tissue within the target area while attempting to induce no damage or minimal damage to tissue other than neural tissue within the target area. According to some embodiments minimal thermal damage to the surrounding tissues is achieved by cooling the surrounding tissues, tissue in the path of the energy transfer and/or shielding it from the effects of the thermal damage induced to the target tissue. According to some embodiments, the laser radiation is not focused, and is introduced in culminated form; according to some embodiments, the power of the laser is set to reach some preferred portions of the target area, and not reach some other portions of the target area. Each possibility represents a separate embodiment of the present disclosure. Without wishing to be bound by any theory or mechanism, neural tissue is more sensitive to thermal damage than tissues such as, but not limited to, blood vessels, muscle tissue and lymphatic vessels, thus enabling to direct thermal damage specifically to neurons within a target area. According to some embodiments, the laser radiation is de-focused; according to some embodiments, defocused laser is positioned close enough to the tissue surface to create smaller damage to a surface of the tissue, expanding geometrically into the target area.

Advantageously, using laser radiation and/or ultrasound energy to selectively induce damage to sensory neurons within the duodenal wall while minimally damaging functional activity of other duodenal tissues may enable efficient treatment of medical conditions such as, but not limited to, obesity and type-2 diabetes, while inducing minimal side effects. Without wishing to be bound by any theory or mechanism, the methods of the disclosure prevent sensing of food-passage through the duodenum. Thus, according to some embodiments, the disclosed methods lead to modulation of the metabolic balance and/or motility and/or physiology of the gastrointestinal tract in a way which enables treatment/amelioration of medical condition such as obesity and/or type-2 diabetes and/or other metabolic syndrome related disease. According to some embodiments, the methods of the invention are able to treat/ameliorate a medical condition such as, but not limited to, obesity and/or type-2 diabetes without impeding duodenal functions not related to treatment of the conditions, such as, but not limited to bicarbonate secretion, maintenance of fluid/electrolyte imbalance and function of duodenal villi.

According to some embodiments, the laser radiation is delivered endoluminally from the duodenal lumen towards at least one target area comprising sensory nerves, the target area residing being within the duodenal wall or in contact with the duodenal wall. Each possibility represents a separate embodiment of the present disclosure. According to some embodiments, the present disclosure provides minimally invasive solutions for endoluminal interventions that selectively block, reduce, limit and/or modulate neuronal activity triggered by food passing through the gastrointestinal (GI) tract, typically through the duodenum, while minimizing side effects by selective spatially localized interventions and/or active/passive cooling/shielding of surrounding tissues and/or layers. According to a non-limiting example, signals triggered by food passing through the GI are neurohormonal signals. According to some embodiments, the target area for intervention may include intrinsic neural pathways, extrinsic neural pathways or a combination thereof. Each possibility represents a separate embodiment of the present disclosure. In certain embodiments, blocking, reducing, limiting or modulating neural activity comprises at least one of: impacting, denervating, modifying, ablating, damaging, severing or otherwise impeding at least part of the neurons in the target area. According to some embodiments, the neurons targeted by the methods of the disclosure are sensory neurons. According to certain embodiments, the neurons targeted by the methods of the disclosure are motor neurons, such as, but not limited to, motor neurons affecting motility of the small intestine. According to some embodiments the targeted tissues compose of axons or the targeted tissues compose of cell-bodies, or both; according to some embodiments the targeted nerves compose of afferent nerves, or the targeted nerves compose of efferent nerves, or both.

According to some embodiments, methods, systems and apparatuses are provided to block and/or affect neural signals generated when a meal passes through the duodenum by impacting, denervating, modifying, blocking, ablating, damaging, cutting, severing or otherwise impeding neural activity of the plexus that reside in the submucosa of the duodenal wall (the submucosal or Meissner's plexus) that transmits locally as well as to extrinsic nerves, such as the Vagal and Ganglia, parasympathetic & sympathetic nerves, signals acquired through the passage of food through chemical sensors in the duodenum while inducing no or minimal damage to the surrounding tissues or layers or substantially impeding their functions.

According to some embodiments, methods, systems and apparatuses are provided for modifying, impacting, blocking, ablating, cutting, damaging, severing or otherwise impeding neural activity of the plexus that reside in the tunica muscularis of the duodenal wall (the Auerbach's plexus or Myenteric plexus), the method and apparatus can enable blocking of signals from mechano-sensors and other chemo-receptors that pass through the Myenteric plexus.

According to some embodiments, methods, systems and apparatuses are provided for modifying, impacting, blocking, ablating, cutting, damaging, severing or otherwise impeding neural activity of the interconnecting synapses and/or other elements of the enteric nervous system (ENS) preferably the intrinsic nervous system that reside within the duodenum wall.

According to some embodiments, methods, systems and apparatuses are provided to block and/or affect signals generated when a meal passes through the duodenum by impacting, denervating, modifying, blocking, ablating, damaging, severing or otherwise impeding neural activity of the local Vagal and Ganglia, parasympathetic & sympathetic nerves at the interface with the duodenum (and/or jejunum) wall or close to it.

According to some embodiments, methods and apparatus are provided to "blind" the duodenum or portions thereof to the meal, chime and nutrients traversing into the intestines from the stomach. This modulates and impacts the metabolic balance and/or motility and/or impacts GI physiology in line with the "foregut hypothesis" set forth by several publications (such as Cummings D E et al. 2004; Pories W. J. et al. 2001; Rubino F. et al. 2002, 2004, 2006; incorporated herein as reference in their entirety). In particular, it has been proposed that this region of the intestines may play a significant role in the development of T2D when overstimulated with nutrients insusceptible individuals, for example via the induction of a putative signal that promotes insulin resistance and T2D.

According to some embodiments, the impact on the plexus is obtained by several impacts across the GI lumen in a form of at least part of a circle to leave most of the tissue without any impact and reduce side effects of intervention.

According to some embodiments, the impact on the plexus is obtained by several impacts across the GI lumen in targeting inner layers of the duodenum wall and in a form of at least part of a circle to leave most of the tissue without any or minimized impact and reduce side effects of intervention.

According to some embodiments, the impact on the plexus is obtained by several impacts across the GI lumen in targeting inner layers of the duodenum wall and in a form of line along the lumen to leave most of the tissue without any impact and reduce side effects of intervention.

According to some embodiments, the impact on the plexus is obtained by several impacts across the GI lumen in targeting inner layers of the duodenum wall and in a form of helix along the lumen to leave most of the tissue without any impact and reduce side effects of intervention; according to some embodiments helical patterns are created to cross each other, such as to form a shape of a net or a stent so as to increase the effect of treatment on the neural plexus.

According to some embodiments, methods and apparatus are provided to ensure shielding of surrounding tissues or layers thereof from damage such as thermal damage so as to leave most of the tissues without any impact and reduce side effects of the aforementioned interventions.

According to some embodiments, methods and apparatus are provided to decrease sensitivity to inter and intra patient mucosa and villi variability by using an energy source such as laser, ultra-sound or RF that is absorbed by the different layers of the duodenum or jejunum or the interface with extrinsic nerves but wherein any impact of the layers until the submucosa are are partially or completed shielded by active cooling of lumen surface.

According to some embodiments, methods and apparatus are provided to ensure shielding of mucosa and villies from damage such as thermal damage so as to leave most of the tissues between the lumen and the submucosa without any impact and reduce side effects of the aforementioned interventions by means of cooling. According to some embodiments means for cooling include mechanical means for stretching at least part of the small intestine to enable cooling fluid (gas or liquid) to penetrate between the mucosa villi.

According to some embodiments cooling can be done by contact with a cold element placed in the lumen such as chilled balloon, cold finger, multiple cold wires, etc.

According to some embodiments cooling can be done with cold liquids in direct contact. According to some embodiments cooling is performed by use of cold gases.

According to some embodiments, a modulated energy source is used to treat the target area; according to some embodiments, the modulated energy source is a laser energy source used to treat the target area, in some embodiments the modulated energy source is an ultrasound energy source used to treat the target area; in some embodiments the modulated energy source is an ultrasound energy source used to treat the target area.

According to some embodiments, a frequency of an energy source is chosen such that the absorption pattern of energy is such that would reach effective energy flux in target tissue, and would reach non-effective energy flux at non target tissue following target tissue; according to some embodiments a frequency of modulated energy source is chosen such that the absorption coefficient corresponds to the distance of target tissue from the source of energy, and the width of that target tissue area after which no effect is desired.

According to some embodiments, the shape of treatment in depth is determined by the shape of the beam, such that closer tissue to the beam is affected in a smaller geometrical shape than deeper tissue by a de-focused beam.

According to some embodiments optical element is used to focus the laser beam on the surface of the lumen that is actively cooled According to some embodiments, elements of the enteric nervous system (ENS), the intrinsic nervous system, are targeted to modulate its function upon passage of a meal through the duodenum and/or stomach. Chemical substances such as antibodies may be used according to some embodiments of the present invention to selectively target elements of ENS. According to some embodiments such chemical substances provide selectivity of targeting elements of the nervous system present within the tissue wall.

According to some embodiments, the blocking of the signals triggered by food either by chemical sensors or mechanical sensors may also modulate motility related functions of the GI tract organs, such as modulation of gastric accommodation and relaxation triggered by a meal passing through the duodenum and/or stomach.

According to some embodiments, this object is achieved by providing a method to block and/or affect signals generated when a meal passes also through the jejunum.

According to some embodiments, this object is achieved by providing an instrument to block and/or affect signals generated when a meal passes also through the jejunum.

According to some embodiments, the present disclosure provides a method for blocking at least part of the neural activity in an organ of a subject in need thereof, the method comprising:

introducing at least one laser element into the organ;

actuating the laser element to emit laser radiation;

focusing the laser radiation to a target area within or in contact with at least part of the wall of the organ, wherein the target area comprises sensory nerves, such that the radiation is configured to cause or induce damage to at least part of the sensory nerves. Each possibility represents a separate embodiment of the present disclosure.

According to some embodiments, functional activity of tissue surrounding the sensory nerves is maintained, despite damage being caused to the at least part of the sensory nerves. According to some embodiments, damage to at least part of said sensory nerves occurs while maintaining functional activity of tissue surrounding said sensory nerves. According to some embodiments, damage to at least part of said sensory nerves occurs while tissue surrounding said sensory nerves maintains its ability to regain its functional activity after the treatment. According to some embodiments means are provided to ensure cooling and/or shielding of surrounding tissues or functional tissue components or layers in order to minimize damage and maintain the functional activity of said tissues, components or layers thereof.

According to some embodiments, the organ is a small intestine or duodenum. According to some embodiments, the wall of the organ is the wall of the duodenum or the duodenal wall. According to some embodiments, the organ is a duodenum and includes a duodenal wall.

According to some embodiments, causing damage to said sensory nerves comprises thermal damage. According to some embodiments, the laser radiation is configured to heat said target area to 45-75° C. According to some embodiments, causing damage to sensory nerves comprises ablation of said target area. According to some embodiments, said laser radiation is pulsed laser radiation. According to some embodiments, causing damage to said sensory nerves comprises causing mechanical damage.

According to some embodiments, the target area comprises at least part of Meissner's plexus, Auerbach's plexus or both. Each possibility represents a separate embodiment of the present disclosure. According to some embodiments, the target area comprises at least part of the Meissner's plexus. According to some embodiments, the target area is comprised in a sub-mucosal layer of the duodenal wall. According to some embodiments, the target area is comprised in a tunica muscularis layer of the duodenal wall. According to some embodiments, the target area is comprised in a mesenteric layer interfacing with the duodenal wall.

According to some embodiments, the subject is afflicted with a medical condition selected from the group consisting of: obesity, type 2 diabetes, insulin resistance, metabolic syndrome, and a combination thereof. Each possibility represents a separate embodiment of the present disclosure.

According to some embodiments, the sensory nerves are configured to be activated by food passing through the duodenum. According to some embodiments, the sensory nerves are configured to transmit signals from mechano-sensors and/or chemo-receptors located within said duodenal wall. Each possibility represents a separate embodiment of the present disclosure. According to some embodiments, the mechano-sensors and/or chemo-receptors are configured to be activated by food passing through the duodenum. According to some embodiments, causing damage to said sensory nerves results in blocking signals from mechano-sensors and/or other chemo-receptors located within said duodenal wall. Each possibility represents a separate embodiment of the present disclosure.

According to another aspect, the present disclosure provides a catheter for blocking at least part of the neural activity in an organ of a subject in need thereof, the catheter comprising:

a laser element configured to emit laser radiation; and a rotatable optical element configured to direct the laser radiation to one or more target areas within or in contact with at least part of a wall of the organ, wherein the target area comprises sensory nerves, such that the radiation is configured to cause damage to sensory nerves.

According to some embodiments, functional activity of tissue surrounding the sensory nerves is maintained, or is able to recuperate post procedure, despite damage being caused to the at least part of the sensory nerves. According to some embodiments the functional activity and structural-functional integrity of the surrounding tissues, components or layers thereof is maintained or is minimally affected, by use of means to cool and/or shield said functional tissue, components or layers thereof from the damage induced to the target tissue or nerves therein. According to some embodiments, the catheter is an endoluminal duodenal catheter. According to some embodiments, the laser element comprises at least one optic fiber. According to some embodiments, the laser radiation is pulsed laser radiation. According to some embodiments, the rotatable optical element deflects said laser radiation at an angle 90 degrees from a longitudinal axis of the catheter. According to some embodiments, the rotatable optical element deflects said laser radiation through an aperture in the catheter. According to some embodiments, the rotatable optical element is located within the distal head of the catheter. According to some embodiments, the rotatable optical element is located within the laser element locates at the distal head of the catheter. According to some embodiments, the organ is a small intestine or duodenum. According to some embodiments, the wall of the organ is the wall of the duodenum or the duodenal wall. According to some embodiments, the catheter is an endoluminal duodenal catheter.

According to some embodiments, the laser element comprises a rotatable optical element configured to focus said laser radiation to a plurality of target areas along a circular trajectory within said duodenal wall or in contact with said duodenal wall; according to some embodiments, the laser element comprises a rotatable optical element configured to focus said laser radiation to a plurality of target areas along a helical trajectory within said duodenal wall or in contact with said duodenal wall. Each possibility represents a separate embodiment of the present disclosure. According to some embodiments, the rotatable optical element is a rotatable prism. According to some embodiments, the rotatable optical element is a beam-splitter prism that defects the laser radiation into a first beam of laser radiation that is focused on said target area and a second beam of laser radiation that is focused on a detector. According to some embodiments, the catheter further comprises at least one lens element. According to some embodiments, the laser element within the catheter further comprises at least one lens element. According to some embodiments, the lens element is a correction lens element for correcting aberration.

According to some embodiments, the rotatable optical element is selected from a group consisting of a wide-angle lens, a dove prism, a reversion or "K" prism, a Delta or Pechan prism, a dispersive prism, a reflective prism, a beam-splitting prism, a deflective prism, a triangular prism, a trapezoidal prism, a Glan-Taylor prism or a Glan-laser prism, a high-powered laser-light right angle prism, a retroreflector and a combination thereof. Each possibility represents a separate embodiment of the present disclosure.

According to some embodiments, the optical element is a wide-angle lens system. According to some embodiments, the optical element is a lens capable of correcting f-theta distortion or f-sin(theta) distortion. According to some embodiments, the system further includes a focusing element that is positioned before the rotatable optical element and is not rotated, with long enough focal length to enable focusing on a target after. According to some embodiments, the rotatable optical element is a dove prism, a reversion or "K" prism, a Delta or Pechan prism, or any other associated prism known in the art.

According to other embodiments, the rotatable optical element is a dispersive prism, a reflective prism, a beam-splitting prism or a deflective prism. According to some embodiments, the prism is a low-loss deflective prism. According to some embodiments, the dispersive prism is a triangular, a Pellin-Broca prism, an Abbe Prism or a compound prism.

According to other embodiments, the prism has a triangular or trapezoidal shape. According to other embodiments, the form of the prism is made from glass (i.e., BK7 glass) and is designed for an adequate laser beam.

According to other embodiments, the prism is a Glan-Taylor prism or a Glan-laser prism. According to other embodiments, the prism is an equilateral glass prism.

According to other embodiments, the prism is selected from a group consisting of anamorphic Prism Pairs, a high-powered laser-light right angle prism, a hollow retroreflector, a laser-line right angle prism, a N-BK7 Corner Cube Retroreflector or a UV Fused Silica Corner Cube Retroreflector.

According to some embodiments, a prism compressor or a pulse compressor is used in conjunction with the prism.

According to some embodiments, a connector is used to connect a fiber leading laser to the actuator; according to some embodiments, a disposable catheter is comprised of a connector of an optic-fiber leading to an optical apparatus reflecting the laser light to the tissue. According to some embodiments a laser source is set in a console made to stand beside the patient bed during treatment, and a connector is used to connect the catheter to the laser source.

According to some embodiments, a mirror is used instead of a beam to manipulate the beam. According to some embodiments imaging tools are used to select the target and align focal plane in the target. According to some embodiments the lumen and/or the duodenal wall is manipulated to determine/force the target area to be within a preset focal plane. Each possibility represents a separate embodiment of the present disclosure. According to some embodiments laser is selected to absorb energy and elevate temperature at the target, according to some embodiments pulsed laser is selected to modify tissue by mode of ablation or similar. According to some embodiments, speed of motion is used to control the thermal effect. According to some embodiments the interface with vagal or ganglion extrinsic nerves is targeted. According to some embodiments a laser beam is linearly scanned in the interface according to some embodiments mean to create a linear, line, spot at the target is used. According to some embodiments the optical element can control the orientation of the focused beam around the axis of the duodenum and the same or other element can scan the spot beam over the duodenum axis. According to some embodiments the optical element can control the orientation and a line spot is generated without need to scan by means such as diode array, using a diffusing fiber with optics.

According to some embodiments, the catheter further comprises an actuator for rotating the rotatable optical element. According to some embodiments, the catheter further comprises a controller for controlling the actuator in accordance with an input signal from an input device. According to some embodiments, the catheter is used with an endoscope.

According to another aspect, the present disclosure provides a system for use in blocking at least part of the neural activity in at least one neural region in an organ of a subject in need thereof, the system comprising:
  a catheter for blocking at least part of the neural activity in the organ of a subject in need thereof, the catheter comprising:
    a laser element configured to emit laser radiation; and
    a rotatable optical element configured to direct the laser radiation to one or more target areas within or in contact with at least part of a wall of the organ, wherein the target area comprises sensory nerves, such that the radiation is configured to cause or induce/trigger damage to sensory nerves. Each possibility represents a separate embodiment of the present disclosure.

According to some embodiments, the rotatable optical element is further configured to focus the laser radiation to said one or more target areas, wherein the energy at the target area is focused to be above that of a surrounding area.

According to some embodiments, the system further includes an imaging device configured to capture structural information related to the duodenal wall or an area in contact with at least part of a duodenal wall. According to some embodiments, the imaging device is an endoscope. According to some embodiments, the imaging device is selected from the group consisting of: an optical imaging device, thermal imaging device, ultrasonic imaging device, Near Infra-Red imaging device, Infra-Red imaging device, Optical Coherence Tomography (OCT) based imaging device and a combination thereof. Each possibility represents a separate embodiment of the present disclosure. According to some embodiments, the structural information comprises a location of layers of said duodenal wall. According to some embodiments, the structural information comprises a location of a mesenteric layer in contact with the at least part of the duodenal wall.

According to some embodiments, the system further includes a controller configured to determine said one or more target area based on the structural information. According to some embodiments, the controller modifies power settings of the laser generator according to structural information obtained. According to some embodiments, the controller modifies focal depth/length parameters according to structural information. According to some embodiments, the system further comprises means of cooling and or shielding the surrounding tissue, components or layers thereof from the thermal damage induced to the target tissue. According to some embodiments said surrounding tissue, components or layers thereof are the mucosal surface of the duodenal wall and/or components thereof such as, but not limited to the duodenal villous structures and adjacent layers or components.

According to some embodiments, the organ is a small intestine or duodenum. According to some embodiments, the wall of the organ is the wall of the duodenum or the duodenal wall. According to some embodiments, the catheter is an endoluminal duodenal catheter.

According to some embodiments, the laser element comprises at least one optic fiber. According to some embodiments, the optical element is a rotatable optical element. According to some embodiments, the rotatable optical element is a prism.

According to some embodiments, functional activity of tissue surrounding the sensory nerves is maintained, despite damage being caused to the at least part of the sensory nerves. According to some embodiments the damage is not immediate but laser or other energy modalities trigger processes that lead to injury and death.

According to some embodiments, the system further comprises at least one pressure-inducing element configured to exert pressure on at least part of said duodenal wall. According to some embodiments, the at least one pressure-inducing element is in the form of a balloon. According to some embodiments, the at least one pressure-inducing element is configured to hold said laser element in place. According to some embodiments, the at least one pressure-inducing element is configured to manipulate the duodenal wall such that a pre-set optical path is achieved between the laser element and target area. According to some embodiments, the at least one pressure-inducing element is configured to manipulate the duodenal wall such that a required pressure on the duodenal wall is achieved. According to some embodiments, the system further comprises a controller configured to determine the pressure exerted by said at least one pressure-inducing element. According to some embodiments, the controller is configured to adjust the pressure exerted by said at least one pressure-inducing element, typically so that a pre-set optical path is achieved between said laser element and target area, or that a required pressure is maintained on the duodenal wall. According to some embodiments, the at least one pressure-inducing element is configured to contain coolant or shielding material that is to minimize exerted thermal damage to surrounding tissue, components or layers thereof. According to some embodiments said surrounding tissue, components or layers thereof are the mucosal surface of the duodenal wall and/or components thereof such as, but not limited to, the duodenal villous structures and adjacent layers or components.

According to some embodiments, there is provided a method for reducing neural activity in an organ of a subject, the method includes introducing at least one laser emitting device including a cooling mechanism into the organ, emitting a laser beam from the laser emitting device to contact a target area on or beneath a wall of the organ and lowering a temperature of the organ using the cooling mechanism, thereby selectively damaging at least one sensory nerve located at the target area to at least partially reduce the neural activity while maintaining functional activity of tissue surrounding the neurons within the target area and/or surrounding the target area.

According to some embodiments, the organ includes a duodenum and the wall includes a duodenal wall.

According to some embodiments, the target area includes at least part of an area selected from the group consisting of a Meissner's plexus and an Auerbach's plexus.

According to some embodiments, the target area is selected from the group consisting of a sub-mucosal layer of the duodenal wall, a tunica muscularis layer of the duodenal wall and a mesenteric layer interfacing with the duodenal wall.

According to some embodiments, the at least one sensory nerve includes at least one nerve that is activated by food passing through the duodenum.

According to some embodiments, the at least one sensory nerve includes at least one nerve that transmits signals from at least one of mechano-sensors or chemo-receptors located within the duodenal wall.

According to some embodiments, the mechano-sensors or chemo-receptors are activated by food passing through the duodenum.

According to some embodiments, damage to the at least one sensory nerve results in blocking signals from at least one of mechano-sensors or chemo-receptors located within the duodenal wall.

According to some embodiments, the laser emitting device includes a rotatable optical element configured to direct the laser beam to a plurality of target areas along a trajectory on or within the duodenal wall.

According to some embodiments, the rotatable optical element is selected from a group consisting of a wide-angle lens, a dove prism, a reversion or "K" prism, a Delta or Pechan prism, a dispersive prism, a reflective prism, a beam-splitting prism, a deflective prism, a triangular prism, a trapezoidal prism, a Glan-Taylor prism or a Glan-laser prism, a high-powered laser-light right angle prism, a retroreflector and combinations thereof.

According to some embodiments, emitting the focused laser beam includes damaging the at least one sensory nerve without adversely affecting functional activity of tissue surrounding the at least one sensory nerve.

According to some embodiments, impeding adverse damage to the functional activity of tissue surrounding the at least one sensory nerve includes cooling or thermal shielding of tissue surrounding the at least one sensory nerve.

According to some embodiments, the cooling or thermal shielding of tissue surrounding the at least one sensory nerve includes the infusion, irrigation or rinsing of tissue surrounding the at least one sensory nerve with a coolant material.

According to some embodiments, the coolant is selected from physiological solutions or biocompatible gels.

According to some embodiments, the cooling or thermal shielding of tissue surrounding the at least one sensory nerve includes the infusion, irrigation or rinsing of the mucosal tissue or the villous structures contained therein.

According to some embodiments, emitting the focused laser causes thermal damage to the at least one sensory nerve.

According to some embodiments, the laser beam is configured to heat the target area to 45-75° C.

According to some embodiments, emitting the focused laser beam includes ablating the at least one sensory nerve.

According to some embodiments, emitting the focused laser beam includes emitting pulsed laser radiation.

According to some embodiments, emitting the focused laser beam causes thermal damage to the at least one sensory nerve causing mechanical damage.

According to some embodiments, the subject is afflicted with a medical condition selected from the group consisting of obesity, type 2 diabetes, insulin resistance, metabolic syndrome, and combinations thereof.

According to some embodiments, there is provided a catheter for reducing neural activity in an organ of a subject, the catheter includes an elongated catheter body having a proximal end and a distal end, a laser emitting element coupled with the catheter body at or near the distal end and configured to emit a focused laser beam, a cooling mechanism coupled with the catheter body, configured to lower a temperature of the organ, and a rotatable optical element coupled with the laser emitting element and configured to direct the focused laser beam to one or more target areas on or beneath a wall of the organ, wherein the target area includes at least one sensory nerve, such that the laser beam is configured to cause damage to the at least one sensory nerve.

According to some embodiments, the organ includes a duodenum and the wall includes a duodenal wall.

According to some embodiments, the catheter includes an endoluminal duodenal catheter.

According to some embodiments, the laser emitting element includes at least one optical fiber.

According to some embodiments, the rotatable optical element includes a rotatable prism.

According to some embodiments, the rotatable optical element is selected from a group consisting of a wide-angle lens, a dove prism, a reversion or "K" prism, a Delta or Pechan prism, a dispersive prism, a reflective prism, a beam-splitting prism, a deflective prism, a triangular prism, a trapezoidal prism, a Glan-Taylor prism or a Glan-laser prism, a high-powered laser-light right angle prism, a retroreflector and combinations thereof.

According to some embodiments, the focused laser beam is configured to heat the one or more target areas to a temperature of 45-75° C.

According to some embodiments, the focused laser beam includes pulsed laser radiation.

According to some embodiments, the rotatable optical element deflects the laser beam at an angle of 90 degrees from a longitudinal axis of the catheter body.

According to some embodiments, the rotatable optical element deflects the focused laser beam through an aperture in the catheter body.

According to some embodiments, the rotatable optical element is located within a distal portion of the catheter body.

According to some embodiments, the catheter further includes an actuator coupled with the rotatable optical element for rotating the rotatable optical element.

According to some embodiments, the catheter further includes a controller coupled with the actuator for controlling the actuator in accordance with an input signal from an input device.

According to some embodiments, the catheter further includes a handle coupled with the catheter body at or near the proximal end, wherein the input device is coupled with the handle.

According to some embodiments, the rotatable optical element includes a beam-splitter prism that deflects the laser beam onto a first beam of laser radiation that is focused on the target area and a second beam of laser radiation that is focused on a detector.

According to some embodiments, the catheter further includes a lens coupled inside the catheter body.

According to some embodiments, the lens includes a correction lens for correcting aberration.

According to some embodiments, the catheter body has an outer diameter selected to fit through with a lumen of an endoscope.

According to some embodiments, there is provided a system for reducing neural activity in at least one neural region in an organ of a subject, the system includes a catheter including an elongated catheter body having a proximal end and a distal end, a laser emitting element coupled with the catheter body at or near the distal end and configured to emit a focused laser beam, a cooling mechanism coupled with the catheter body, configured to lower a temperature of the organ, and a rotatable optical element coupled with the laser emitting element and configured to direct the focused laser beam to one or more target areas on or beneath a wall of the organ, wherein the target area includes at least one sensory nerve, such that the laser beam is configured to cause damage to the at least one sensory nerve.

According to some embodiments, the organ includes a duodenum and the wall includes a duodenal wall.

According to some embodiments, the catheter includes an endoluminal duodenal catheter.

According to some embodiments, the system further includes an imaging device configured to capture structural information related to the duodenal wall or an area in contact with at least part of the duodenal wall.

According to some embodiments, the system further includes a controller configured to determine the one or more target areas based on the structural information.

According to some embodiments, the imaging device includes an endoscope.

According to some embodiments, the imaging device is selected from the group consisting of an optical imaging device, thermal imaging device, ultrasonic imaging device, Near Infra-Red imaging device, Infra-Red imaging device, Optical Coherence Tomography (OCT) based imaging device and combinations thereof.

According to some embodiments, the structural information includes a location of layers of the duodenal wall.

According to some embodiments, the structural information includes a location of a mesenteric layer in contact with the duodenal wall.

According to some embodiments, the laser element includes at least one optical fiber.

According to some embodiments, the rotatable optical element includes a rotatable prism.

According to some embodiments, the rotatable optical element is selected from a group consisting of a wide-angle lens, a dove prism, a reversion or "K" prism, a Delta or Pechan prism, a dispersive prism, a reflective prism, a beam-splitting prism, a deflective prism, a triangular prism, a trapezoidal prism, a Glan-Taylor prism or a Glan-laser prism, a high-powered laser-light right angle prism, a retroreflector and combinations thereof.

According to some embodiments, the laser beam is configured to heat the one or more target areas to a temperature of 45-75° C.

According to some embodiments, the laser beam includes pulsed laser radiation.

According to some embodiments, the system further includes at least one pressure-inducing element coupled with the catheter body and configured to exert pressure on at least part of the wall of the organ.

According to some embodiments, the at least one pressure-inducing element includes a balloon.

According to some embodiments, the at least one pressure-inducing element is further configured to hold the laser emitting element in place.

According to some embodiments, the system further includes a controller configured to determine the pressure exerted by the at least one pressure-inducing element.

According to some embodiments, the pressure-inducing element further includes laser transmissive cooling or thermal shielding material.

According to some embodiments, the laser transmissive cooling or thermal shielding material is selected from physiological solutions or biocompatible gels.

According to some embodiments, the laser transmissive cooling or thermal shielding material contained within the pressure-inducing element is used for cooling or thermal shielding of the mucosal tissue or the villous structures contained therein.

According to some embodiments, there is provided a method for reducing neural activity in an organ of a subject, the method includes advancing a distal end of a flexible, laser emitting catheter into a small intestine of the subject, identifying a target area on or beneath a wall of the small intestine, emitting a focused laser beam from the laser emitting catheter to contact the target area, and lowering a temperature of the organ using a cooling mechanism, thereby selectively damaging at least one sensory nerve located at the target area to at least partially reduce the neural activity while maintaining functional activity of tissue surrounding the neurons within the target area and/or surrounding the target area.

According to some embodiments, identifying the target area is performed using a visualization device located in the small intestine.

According to some embodiments, identifying the target area is performed before the advancing step.

According to some embodiments, the distal end of the laser emitting catheter is advanced into the duodenum, and wherein the wall of the small intestine includes a duodenal wall.

According to some embodiments, the method further includes repeating at least the emitting step to damage more than one sensory nerve at the target area or at a different target area.

According to some embodiments, emitting the focused laser beam includes directing the beam with a rotatable optical element coupled with the laser emitting catheter.

According to some embodiments, directing the beam includes angling the beam so that it passes through an aperture on a side of the catheter.

According to some embodiments, the method further includes splitting the beam into two beams, wherein a first beam of the two beams is directed at the target area.

According to some embodiments, there is provided a system for use in blocking at least part of neural activity in at least one neural region in an organ of a subject in need thereof, the system includes a catheter for blocking at least part of the neural activity in the organ of a subject in need thereof. The catheter includes an elongated catheter body having a proximal end and a distal end, a laser emitting element coupled with the catheter body at or near the distal end and configured to emit a focused laser beam, a cooling mechanism coupled with the catheter, configured to lower a temperature of the organ, and a scanning optical element coupled with the laser emitting element and configured to direct the focused laser beam to one or more target areas on or beneath a wall of the organ, wherein the target area includes at least one sensory nerve, such that the laser beam is configured to cause damage to the at least one sensory nerve.

According to some embodiments, the scanning of the laser targets the VAN interface with the duodenum to elevate temperature and induce injury in nerves.

According to some embodiments, the scanning optical element enables deflection of the light of one of; (i) a line parallel to the lumen axis; (ii) around the lumen axis.

According to some embodiments, the laser radiation includes a wavelength configured to be strongly absorbed by a pigment inserted to enhance absorption at the target.

According to some embodiments, there is provided a method for reducing blocking at least part of the neural activity in an organ of a subject in need thereof, the method includes introducing at least one light emitting element emitting device and a cooling mechanism into the organ, actuating the light source element to activate a photosensitizer to induce injury at target area on or beneath, within or in contact with at least part of a wall of the organ and lowering a temperature of the organ utilizing the cooling mechanism, thereby selectively damaging at least one sensory nerve located at the target area to at least partially reduce the neural activity while maintaining functional activity of tissue surrounding the neurons within the target area and/or surrounding the target area.

According to some embodiments, the photosensitizer includes an anti-body that specifically binds to an element of the neural system.

According to some embodiments, there is provided a method for reducing neural activity in an organ of a subject, the method includes introducing into the organ a catheter including at least one ultrasound emitting device and a cooling mechanism, emitting a modulating ultrasound beam from the ultrasound emitting device to contact a target area on or beneath a wall of the organ and cooling at least the wall of the organ with the cooling mechanism, thereby selectively damaging at least one sensory nerve located at the target area to at least partially reduce the neural activity while maintaining functional activity of tissue surrounding the neurons within the target area and/or surrounding the target area.

According to some embodiments, the organ includes a duodenum and the wall includes a duodenal wall, and the cooling mechanism includes an irrigation mechanism configured to provide irrigation fluids to the duodenum.

According to some embodiments, the modulating ultrasound beam includes a collimated ultrasound beam.

According to some embodiments, the modulating ultrasound beam includes a diverting ultrasound beam.

According to some embodiments, the modulating ultrasound beam includes a partially focused ultrasound beam.

According to some embodiments, the modulating ultrasound beam includes a focused ultrasound beam.

According to some embodiments, the ultrasound emitting device is configured to emit ultrasound beams at controllable intensities.

According to some embodiments, the ultrasound transducer is further configured to perform ultrasound imaging.

According to some embodiments, the method further includes obtaining ultrasound imagery prior to emitting the ultrasound beam.

According to some embodiments, the method further includes introducing an imaging ultrasound transducer and obtaining ultrasound imagery prior to emitting the ultrasound beam.

According to some embodiments, the ultrasound emitting device includes an ultrasound transducer.

According to some embodiments, the ultrasound emitting device includes a piezoelectric ultrasound transducer.

According to some embodiments, the method further includes introducing an inflatable pressure-induced structure and inflating the pressure induced structure against the wall of the organ.

According to some embodiments, the pressure induced structure is a balloon including latex.

According to some embodiments, the pressure induced structure is a balloon including silicone.

According to some embodiments, the method further includes approximating the ultrasound emitting device to the wall of the organ.

According to some embodiments, the method further includes rotating the ultrasound emitting device and positioning it in a desired orientation.

According to some embodiments, irrigation fluids include saline.

According to some embodiments, there is provided a catheter for reducing neural activity in an organ of a subject, the catheter includes an elongated catheter body having a proximal end and a distal end, an ultrasound emitting element coupled with the catheter body at or near the distal end and is configured to emit a modulating ultrasound beam to one or more target areas on or beneath a wall of the organ, and a cooling mechanism coupled with the catheter, configured to lower a temperature of the organ wall, wherein the target area includes at least one sensory nerve, such that the laser beam is configured to cause damage to the at least one sensory nerve.

According to some embodiments, the organ includes a duodenum and the wall includes a duodenal wall, and the cooling mechanism includes an irrigation mechanism configured to provide irrigation fluids to the duodenum.

According to some embodiments, the ultrasound emitting element is further configured to provide ultrasound imagery of the organ and an environment thereof.

According to some embodiments, the catheter further includes an ultrasound imagery device coupled with the catheter body and configured to provide ultrasound imagery of the organ and an environment thereof.

According to some embodiments, the modulating ultrasound beam includes a collimated ultrasound beam.

According to some embodiments, the modulating ultrasound beam includes a diverting ultrasound beam.

According to some embodiments, the modulating ultrasound beam includes a partially focused ultrasound beam.

According to some embodiments, the modulating ultrasound beam includes a focused ultrasound beam.

According to some embodiments, the ultrasonic emitting element is configured to radially emit ultrasonic waves covering a full circular range (360 degrees).

According to some embodiments, the ultrasonic emitting element is configured to radially emit ultrasonic waves covering a portion of a circular range (less than 360 degrees).

According to some embodiments, the ultrasonic emitting element is a first ultrasonic emitting element and the catheter further includes a second ultrasonic emitting element coupled with the catheter body at or near the distal end and is configured to emit a modulating ultrasound beam to one or more target areas on or beneath a wall of the organ.

According to some embodiments, the one or more target areas of the first ultrasonic emitting element are not the same one or more target areas of the second ultrasonic emitting element.

According to some embodiments, the catheter further includes an inflatable structure connected to the catheter body and configured to inflate and press against the wall of the organ.

According to some embodiments, the inflatable structure is further configured to locate the catheter body at a desired location within the organ.

According to some embodiments, the desired location is a centered location having relatively equal distance from the wall of the organ at different directions.

According to some embodiments, the irrigation mechanism is configured to provide irrigation fluids to the organ and the inflatable structure is configured to confine the irrigation fluid in a desired space within the organ.

According to some embodiments, the catheter body is rotatable and configured to enable positioning the ultrasound emitting element at a desired orientation.

According to some embodiments, the catheter further includes a first inflatable structure at the distal end of the catheter body and a second inflatable structure at the proximal end of the catheter body; the first inflatable structure and the second inflatable structure are configured to inflate and press against the wall of the organ.

According to some embodiments, the irrigation mechanism is configured to provide irrigation fluids to an area confined by the first inflatable structure, the second inflatable structure and the wall of the organ.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 1A schematically illustrates a section of a duodenum, depicting various layers of the duodenal wall.

FIG. 1B schematically illustrates a lateral cross section through a duodenum, depicting various layers of the duodenal wall.

DETAILED DESCRIPTION

Figure 2A:
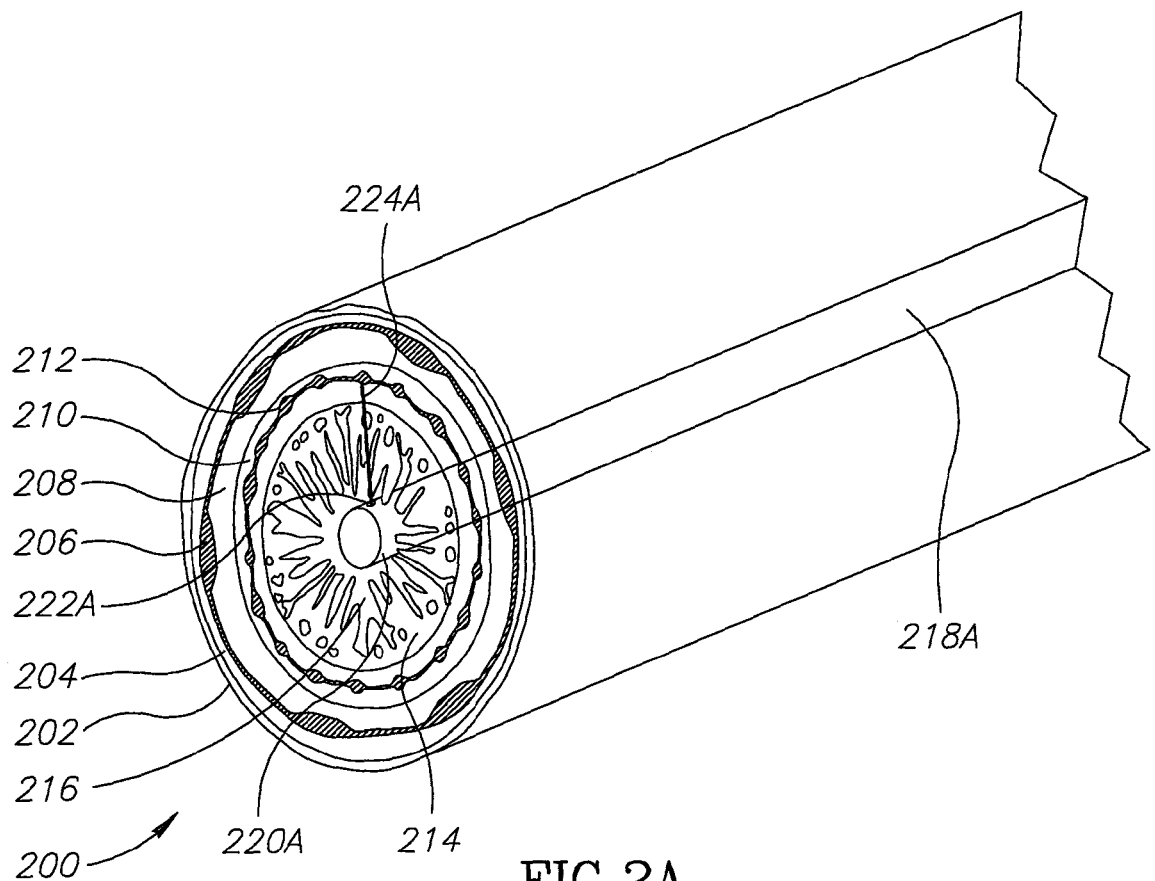
FIG. 2A schematically illustrates a catheter, which is inserted into the lumen of the duodenum, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The terms "comprises", "comprising", "includes", "including", "having" and their conjugates, as used herein, mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure. In the description and claims of the application, each of the words "comprise" "include" and "have", and forms thereof, are not necessarily limited to members in a list with which the words may be associated.

As used herein, the singular form "a", "an" and "the" include plural references unless the context clearly dictates otherwise. For example, the term "a compound" or "at least one compound" may include a plurality of compounds, including mixtures thereof.

As used herein the term "about" refers to plus/minus 10% of the value stated. As used herein, the term "plurality" refers to at least two.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

According to one aspect, the present disclosure provides a method for blocking at least part of the neural activity in an organ of a subject in need thereof, the method comprising:
  introducing at least one laser element into the organ;
  actuating the laser element to emit laser radiation;
  focusing the laser radiation to a target area within or in contact with at least part of a wall of the organ, wherein the target area comprises sensory nerves, such that the radiation is configured to cause damage to at least part of the sensory nerves.

According to some embodiments, the organ is a small intestine or duodenum. According to some embodiments, the wall of the organ is the wall of the duodenum or the duodenal wall.

According to some embodiments, functional activity of tissue surrounding the sensory nerves is maintained, despite damage being caused to the at least part of the sensory nerves. According to some embodiments, tissue surrounding the sensory nerves is minimally affected. According to some embodiments, tissue surrounding the sensory nerves is minimally affected such as it can regain its functional capacity post treatment. According to some embodiments the functional activity and structural-functional integrity or ability to recuperate of said surrounding tissues, components or layers thereof is maintained by use of means to cool and or shield said functional tissue, components or layers thereof from the damage induced to the target tissue or nerves therein.

I. BIOLOGICAL DEFINITIONS

As used herein, the term "duodenum" refers to the part of the small intestine of a vertebrate's gastrointestinal tract which is situated between the stomach and the jejunum. According to some embodiments, the duodenum comprises the pylorus of the stomach. According to some embodiments, the pylorus of the stomach comprises at least one of: the pyloric antrum, the pyloric canal and a combination thereof. Each possibility represents a separate embodiment of the present disclosure. According to some embodiments, the duodenum comprises the duodenal-jejunal junction. According to some embodiments, the duodenum comprises the lumen and the duodenal wall surrounding the lumen. As used herein, the terms "duodenal wall" and "wall of the duodenum" are used interchangeably.

According to some embodiments, the duodenal wall comprises the following layers from the lumen outwards: the mucosa villi layer, the submucosa layer which comprises the submucosal plexus, the circular muscle layer, the myentric plexus, the longitudinal muscle layer and the peritoneum/mesenteric layer. According to some embodiments, the combination of the circular muscle layer and longitudinal muscle layer is referred to herein as the tunica muscularis.

According to some embodiments, the terms "submucosal plexus" and "Meissner's plexus" are used interchangeably and refer to a neural plexus residing in the submucosa layer of the duodenal wall. According to some embodiments, the submucosal plexus transmits neural signals within the duodenum. According to some embodiments, the submucosal plexus transmits neural signals to nerves extrinsic to the duodenum, such as, but not limited to the vagus, duodenal ganglia, sympathetic nerves, parasympathetic nerves and a combination thereof. Each possibility represents a separate embodiment of the present disclosure. According to some embodiments, the submucosal plexus comprises mainly sensory neurons. According to some embodiments, the submucosal plexus transmits neural signals resulting from activity of chemical and/or mechanical sensors in the duodenum. Each possibility represents a separate embodiment of the present disclosure. According to some embodiments, the submucosal plexus transmits neural signals resulting from activity of chemical and/or mechanical sensors in the duodenum which are configured to be activated by passage of food through the duodenum. Each possibility represents a separate embodiment of the present disclosure.

According to some embodiments, the terms "Auerbach's plexus" and "Myentric plexus" are used interchangeably and refer to a neural plexus residing in the tunica muscularis of the duodenal wall. According to some embodiments, signals from mechano-sensors and/or chemo-receptors in the duodenal wall which are induced by passage of food through the duodenum pass through the Myentric plexus.

Reference is now made to FIG. 1A, showing a schematic representation of section (100) through part of a duodenum, depicting the various layers of the duodenal wall according to some embodiments. Lumen (102) is surrounded by mucosa (104), which in turn is surrounded by submucosa layer (106). Submucosa layer (106) comprises submucosal plexus (108). Submocosal plexus (108) innervates nerves (124a, 124b, 124c, 124d, 124e and 124f) which are part of vein, arteries and nerves (VAN) arrays (122a, 122b, 122c, 122d, 122e and 122f), respectively, present in mesenteric layer (120) of the duodenal wall. According to some embodiments, nerves (124a, 124b, 124c, 124d, 124e and 124f) transfer signals outside of the duodenum to nerves such as, but not limited to, vagal nerves, sympathetic nerves, parasympathetic nerves or a combination thereof. Blood vessels of VAN (vein, arteries and nerves) arrays (122a, 122b, 122c, 122d, 122e and 122f) are connected to blood vessels (110) in the duodenal wall. Circular muscle layer (112) surrounds submucosa layer (106). Myentric plexus (116) is present in intermuscular stroma (114) which resides between circular muscle (112) and longitudinal muscle (118). Longitudinal muscle (118) is surrounded by mesenteric/peritoneum layer (120). FIG. 1B depicts a cross section through duodenum section (100), showing lumen (102), mucosa (104), submucosa layer (106) which comprises submucosal plexus (108), circular muscle (112), Myentric plexus (116), longitudinal muscle (118) and mesenteric/peritoneum layer (120), according to some embodiments.

According to some embodiments, blocking at least part of the neural activity in an organ, such as a duodenum, refers to blocking at least part of the neural activity in sensory neurons of the organ. According to some embodiments, blocking at least part of the neural activity in a duodenum refers to blocking neural activity in at least one target area. According to some embodiments, blocking at least part of the neural activity in a duodenum refers to blocking sensory neural activity in at least one target area. According to some embodiments, blocking at least part of the neural activity in a duodenum refers to blocking at least part of the neural activity in response to passage of food through the duodenum. According to some embodiments, blocking at least part of the neural activity in a duodenum refers to blocking at least part of the neural activity in sensory neurons in response to passage of food through the duodenum. According to some embodiments, passage of food through the duodenum induces neural activity in the duodenum. According to some embodiments, passage of food through the duodenum induces activity of sensory neurons in the duodenum. According to some embodiments, passage of food through the duodenum induces neural activity in the duodenum as a response to signals triggered by the food passage, such as, but not limited to, neurohormonal signals, signals received from mechano-sensors, signals received from chemo-sensors and a combination thereof. Each possibility represents a separate embodiment of the present disclosure.

According to some embodiments, blocking neural activity in a target area refers to at least one of: reducing neural conductance within at least some neurons in the target area, abrogating neural conductance within at least some neurons in the target area, reducing neural conductance within at least some synapses in the target area, abrogating neural conductance within at least some synapses in the target area or a combination thereof. Each possibility represents a separate embodiment of the present disclosure. As used herein, the terms "neuron" and "nerve" are used interchangeably.

According to some embodiments, a target area is an area that contains neural structures which resides within a duodenal wall or in contact with at least part of a duodenal wall. According to some embodiments, the target area resides within at least one layer of the duodenal wall. According to some embodiments, the target area resides at the interface between duodenal wall and sensory nerves that are configured to transmit neural signals out of the duodenum, such as, but not limited to, neurons in VAN (vein, arteries nerves) arrays. According to some embodiments, a target area comprises neurons configured to transmit internal neural signals within the duodenum. According to some embodiments, a target area comprises sensory neurons configured to transfer signals between neural plexuses and/or chemical/mechanical sensors within the duodenal wall. Each possibility represents a separate embodiment of the present disclosure. According to some embodiments, a target area comprises sensory neurons configured to transmit neural signals outside of the duodenum to various ganglia and/or nerves such as, but not limited to, vagal nerves and/or various sympathetic and/or parasympathetic nerves. According to some embodiments the target area comprises of non-sensory neurons contributing to the hormone secretion in the duodenal area. In some embodiments the target area comprises of neural axons or cell bodies of neurons or ganglia or a combination of the above. Each possibility represents a separate embodiment of the present disclosure.

According to some embodiments, a target area comprises sensory neurons configured to transmit signals in response to passage of food through the duodenum. As used herein, the term "sensory neurons" relates to neurons configured to transmit neural stimuli corresponding to sensory stimuli. According to some embodiments, sensory neurons are activated by physical and/or chemical stimuli, such as, but not limited to, mechano-sensors and/or chemo-receptors on the duodenal wall. Each possibility represents a separate embodiment of the present disclosure. According to some embodiments, sensory neurons within a target area in the disclosed method relates to sensory neurons configured to transmit sensory stimuli induced by passage of food through the duodenum. As used herein, the term "motor neurons" relates to neurons configured to induce muscle movement, either directly or indirectly.

According to some embodiments, a target area comprises sensory neurons configured to transmit signals in response to signals received from mechano-sensors and/or chemo-receptors within the duodenal wall. Each possibility represents a separate embodiment of the present disclosure. According to some embodiments, a target area comprises sensory neurons configured to transmit signals in response to signals received from mechano-sensors and/or chemo-receptors within the duodenal wall in response to food passage through the duodenum. Each possibility represents a separate embodiment of the present disclosure.

According to some embodiments, the target area comprises at least part of the myentric plexus, the submucosal plexus or a combination thereof. Each possibility represents a separate embodiment of the present disclosure. According to some embodiments, the target area comprises at least part of the submucosal plexus. According to some embodiments, the target area comprises at least part of the neurons within VAN arrays present in the mesenteric layer of the duodenal wall. According to some embodiments, the target area comprises at least part of the neurons connecting the duodenum to VAN arrays present in the mesenteric layer of the duodenal wall.

According to some embodiments, the target area comprises at least part of the neurons within regions selected from the group consisting of: the myentric plexus, the submucosal plexus, duodenal branches of the vagus nerve, sympathetic nerves innervating the duodenal wall, parasympathetic nerves innervating the duodenal wall, VAN arrays in the duodenal wall and a combination thereof. Each possibility represents a separate embodiment of the present disclosure. According to some embodiments, the target area comprises the anterior (left) vagal nerve. According to some embodiments, the target area comprises the interface of the anterior (left) vagal nerve with the duodenum. According to some embodiments, the target area comprises at least part of the hepatic branch of the left vagal nerve and/or at least part of the gastroduodenal branch of the vagal nerve. Each possibility represents a separate embodiment of the present disclosure.

According to some embodiments, a target area may further comprise motor neurons. According to some embodiments, a target area within the Myentric plexus may further comprise motor neurons. Without wishing to be bound by any theory or mechanism, motor neurons may be able to regenerate following damage, thus induction of damage to sensory neurons within a target area while maintaining functional activity of motor neurons within the target area is enabled.

According to some embodiments surrounding tissues, components or layers thereof are the tissues surrounding the target tissue and/or layers of the duodenal wall as described above and/or the aforementioned neural structures therein. According to some embodiments the surrounding tissues, components or layers thereof include, but are not limited to, the mucosal surface of the duodenal wall and/or components thereof such as, but not limited to, the duodenal villous structures and adjacent layers or components of the duodenal wall.

II. LASER ELEMENT AND CATHETER

According to some embodiments, the disclosed method comprises introduction of at least one laser element into an organ, such as the lumen of a subject's duodenum. According to some embodiments, a laser element is an element configured to emit laser radiation. According to some embodiments, a laser element refers to an optomechanic system configured to deliver laser radiation. As used herein, the terms laser element, optomechanic system and optomechanical head are used interchangeably. According to some embodiments, a laser element is an element configured to emit focused laser radiation. According to some embodiments, the laser element is comprised in, and possibly located within, a catheter. According to some embodiments, the laser element is configured to emit non-focused laser. According to some embodiments, the laser element is configured to emit culminated laser. Each possibility represents a separate embodiment of the present disclosure. According to some embodiments, the laser element is attached to a catheter. According to some embodiments, a laser is connected to the catheter and/or laser element through at least one optical fiber. According to some embodiments the optical fiber is connected to a laser light generator using fiber welding. According to some embodiments the optical fiber is connected to a laser light generator using a fiber connector. According to some embodiments the connector is a cooled connector. According to some embodiments, the optomechanical head is introduced into the lumen of a subject's duodenum by using a catheter. According to some embodiments, the optomechanical head is introduced into the lumen of a subject's duodenum by using an endoscope. As used herein, the terms "catheter" and "endoluminal duodenal catheter" are used interchangeably and refer to a catheter which is configured to be introduced into the lumen of a duodenum. According to some embodiments, the catheter is configured to be introduced into the lumen of a duodenum through the mouth of a subject. According to some embodiments, the catheter is configured to be introduced through the colon. According to some embodiments the catheter is configured to be introduced into the lumen of the duodenum through the nose. According to some embodiments, the catheter has a proximal region and a distal region. In certain embodiments, the distal region has one or more apertures. According to some embodiments, the distal region of the catheter has a larger diameter than the proximal region of the catheter. According to some embodiments, the distal region is made of a different material than the proximal region of the catheter, such as, but not limited to including a hydrophilic coating.

According to some embodiments, a laser element comprises at least one optic fiber. According to some embodiments, a laser element comprises at least part of an optic fiber. According to some embodiments, the optic fiber is configured to emit laser radiation. According to some embodiments, the optic fiber is functionally connected to a laser source. According to some embodiments, the laser element is functionally connected to a laser source. According to some embodiments, the laser element comprises the laser source. According to some embodiments, the laser source is external to the subject to which the laser element is inserted.

According to some embodiments, the laser element comprises a rotatable optical element. According to some embodiments, the rotatable optical element is a rotatable prism. According to some embodiments, the rotatable optical element is a rotatable mirror. According to some embodiments, the rotatable optical element is a rotatable beam splitter. According to some embodiments, the rotatable optical element is located in the distal region of the catheter. According to some embodiments the laser element comprises of a static lens. According to some embodiments the laser comprises of a static lens geometrically configured to create a shaped lesion. According to some embodiments the laser comprises of a static lens geometrically configured to create a lesion in the shape of a circular 'doughnut' shape.

Reference is now made to FIG. 2A depicting use of the disclosed method, system and apparatus, according to some embodiments. Catheter (218A) which comprises laser element (220A) is introduced into lumen (216) of duodenum (200). Laser element (220A) emits focused laser radiation (224A) through optical window (222A). Laser radiation (224A) crosses mucosal layer (214) and is focused on submucosa layer (210) to target submucosal plexus (212). According to some embodiments laser element (220A) which may be an optomocechanical head, is configured to target submucosal plexus (212). According to certain embodiments selective targeting is achieved by using chemical substances that bind to elements of the neural system. According to other embodiments, laser element (220A) may emit laser radiation focused on part on the tunica muscularis layers such as circular muscle (208) and longitudinal muscle layer (204) . . . . According to other embodiments, laser element (220A) may emit laser radiation focused on part of myentric plexus (206) residing between circular muscle (208) and longitudinal muscle layer (204). According to certain embodiments, laser element (220A) may emit laser radiation focused on a target area in mesentry layer (202) comprising sensory neurons which innervate the duodenal wall. According to some embodiments, the laser radiation may be in the form of a line focused on a target area or a a spot scanned across the interface area in mesentry layer (202) comprising sensory neurons which innervate the duodenal wall. According to certain embodiments, laser element (220A) may emit laser radiation focused on a target area on other areas within the lumen (216) of duodenum (200).

Figure 2B:
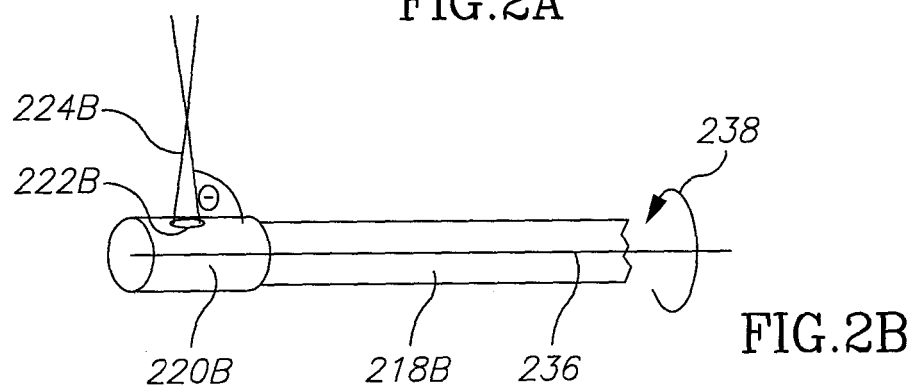
FIG. 2B schematically illustrates an endoluminal duodenal catheter, which emits a laser beam, according to certain embodiments.

FIG. 2B illustrates an endoluminal duodenal catheter according to some embodiments. Catheter (218B) comprises laser element (220B), which emits laser radiation (224B) through aperture (222B), according to some embodiments. According to some embodiments, laser radiation (224B) has angle (θ) relatively to catheter (218B). According to some embodiments, angle (θ) may be 90 degrees, or have an acute or obtuse angle configured to deliver laser radiation (224B) to a desired target area. According to some embodiments, laser element (220B) is rotatable, such that laser radiation (224B) may be focused to a plurality of target areas within a substantially circular trajectory. According to some embodiments, laser element (220B) is rotatable around longitudinal axis (236) of catheter (218B). According to some embodiments, an actuator is used to rotate the laser element. According to some embodiments, rotation angle (238) of laser element (220B) may be, but is not limited to, 0, 30, 45, 70, 90, 120, 150, 180 or 360 degrees around longitudinal axis (236) of catheter (218B). Each possibility represents a separate embodiment of the present disclosure.

Figure 2C:
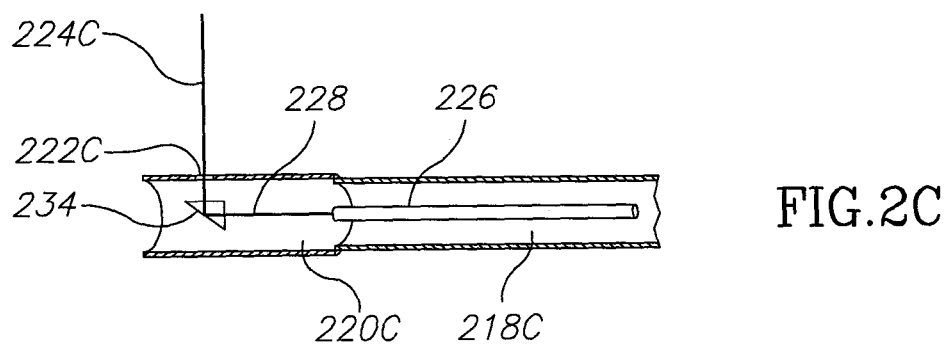
FIG. 2C schematically illustrates a longitudinal cross section through a catheter, according to certain embodiments.

FIG. 2C illustrates, according to some embodiments, a longitudinal cross section through the endoluminal duodenal catheter illustrated in FIG. 2B. Catheter (218C) comprises optomechanical head (220C) and optic fiber (226). According to some embodiments, optic fiber (226) is functionally connected to a laser source. Optic fiber (226) is at least partly comprised within optomechanical head (220C) and emits laser radiation (228). Laser radiation (228) is directed at rotatable prism (234) which deflects laser radiation (228) to laser radiation (224C). Although rotatable prism (234) is depicted as a triangular prism it is to be noted that any suitable shape may be used, such as, but not limited to, pyramidal, hexagonal or cuboidal. Other such prisms, or any other associated prisms or lens elements known in the art may be used. Additional detail is provided below in Section VIII regarding optical lens systems.

As shown, laser radiation (224C) exits optomechanical head (220C) through optical window (222C) and is directed towards a target area within the duodenal wall. According to some embodiments, optical window (222C) is an aperture. According to other embodiments, the walls of catheter (218C) are transparent, obviating the need for an aperture or optical window. According to some embodiments, more than one aperture is located in the walls of the catheter (218C). According to some embodiments, optical window (222C) may be located at an angle and/or position which allows laser radiation (224C) to exit optomechanical head (220C).

Figure 2D:
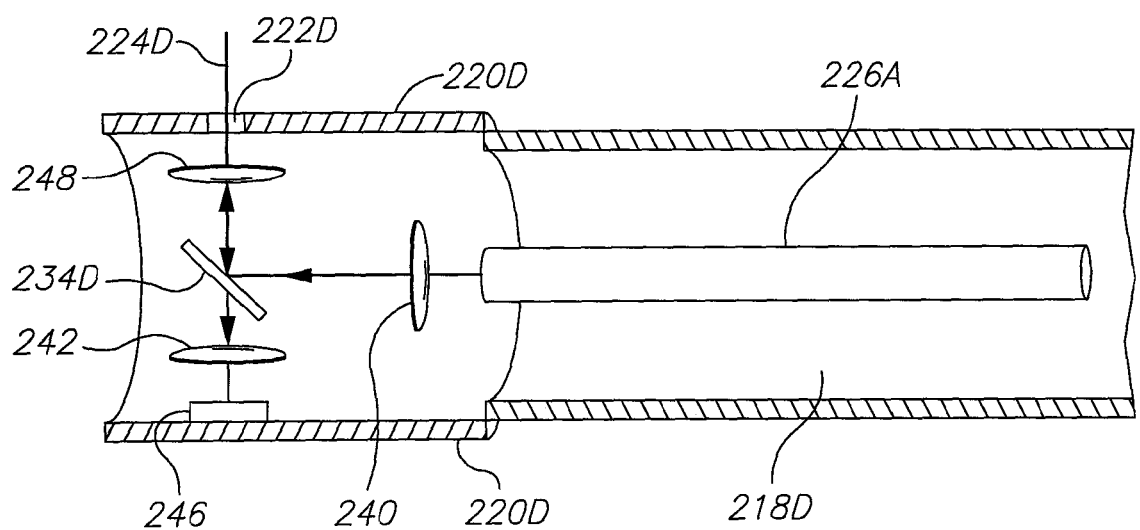
FIG. 2D schematically illustrates a longitudinal cross section through a catheter, according to certain embodiments.

FIG. 2D illustrates a longitudinal cross section through an endoluminal duodenal catheter, according to certain embodiments of the present disclosure. Catheter (218D) comprises laser element (220D) and optic fiber (226A). According to some embodiments, optic fiber (226A) emits laser radiation (224D) through lens (240) towards reflecting beam splitter (234D). Laser radiation (224D) passes through lens (248) and optical window (222D) towards a target area. According to some embodiments, reflecting beam splitter (234D) is a partially reflective mirror configured to enable some of the laser radiation reflected back from the target area and/or some of the scattered radiation to pass through lens (242) and be collected by imaging element (246). Imaging element (246) may be any suitable element for capturing information about the structure of the duodenum and/or surrounding tissue. According to some embodiments, imaging element (246) is configured to enable determining whether laser beam (224D) is focused on the desired target area and/or monitoring the irradiation process in real time. Each possibility represents a separate embodiment of the present disclosure. According to some embodiments, laser element (220D) includes means to rotate around the longitudinal axis of catheter (218D) together with lenses (240, 242), reflecting beam splitter (234D) and imaging element (246). According to some embodiments, imaging element (246) may comprise single or multiple detectors such as CMOS and/or CCD. According to some embodiments, imaging element (246) is not configured to rotate and can enable imaging only during part of the rotation around the longitudinal axis of catheter (218D). Non-limiting examples of imaging elements, may be, but not limited to a liner array camera or an array detector that is stationary and surrounds catheter (218D) such as a CCD or a CMOS chip linear array. According to some embodiments, imaging element (246) includes or is functionally connected to a processor or a controller to control and process information about the structure of the duodenum and/or surrounding tissue. According to some embodiments, the processor or controller is configured to process information regarding changes in target area characteristics upon interaction with the laser beam. According to some embodiments, the optical path used for focusing may be used for imaging if required, such as, but not limited to, using the confocal optics principle. Alternatively, a different optical path may be used for focusing laser radiation at a target area and imaging. According to non-limiting examples, imaging may be performed using technologies such as, but not limited to, Near Infra-Red (NIR), visible direct of fluorescence based optical imaging, ultrasound based imaging, photoacousticmicroscopy, Optical Coherence Tomography (OCT) based imaging or any combination thereof. According to some embodiments, for implementation of photoacoustic imaging/microscopy that is based on the photoacoustic effect in which the pulse energy induces an acoustic wave that is sensitive to laser energy absorption and mechanical characteristics of the tissue, at least one acoustic transducer is attached to the catheter with direct or semi-direct contact with the tissue or through interface through liquid. Each possibility represents a separate embodiment of the present disclosure.

III. LASER ELEMENT AND TYPES OF LASER RADIATION

According to some embodiments, the disclosed method comprises focusing laser radiation to a target area within or in contact with at least part of an organ of a subject, such as a subject's duodenum and/or duodenal wall to selectively ablate and/or damage neurons, such as, but not limited to sensory nerves including, but not limited to sensory nerves in the submucosal plexus or the myentric plexus of the duodenum. Each possibility represents a separate embodiment of the present disclosure.

According to some embodiments, the laser radiation is laser radiation not configured to be significantly absorbed in a tissue of an organ of a subject, such as a subject's duodenum. According to some embodiments, laser radiation not configured to be absorbed in tissue outside the target area may pass through at least one layer of the duodenum on its way to the target area without causing damage to the at least one layer of the duodenum. In a non-limiting example, laser radiation not configured to be significantly absorbed in tissue outside the target area which is directed at a target area within the submucosal layer of the duodenum may traverse through the mucosal layer of the duodenum without damaging it. According to some embodiments, laser radiation not configured to be absorbed in tissue outside the target area is laser radiation configured to induce an energy peak sufficient to cross a fluence threshold to damage a tissue or initiate a process leading to damage only within the target area. Each possibility represents a separate embodiment of the present disclosure.

According to some embodiments, laser radiation not configured to be absorbed in tissue outside the target area is selected from the group consisting of: pulsed laser or CW laser or Quasi CW radiation in Near Infra-Red (NIR) or visible spectrum and a combination thereof. Each possibility represents a separate embodiment of the present disclosure. According to some embodiments, NIR laser radiation is typically in the range of 700-1350 nm. According to some embodiments, the laser radiation is typically in the range of 700-1350 nm. According to some embodiments, the laser radiation is in a range selected from the group consisting of: 700-900 nm, 700-1100 nm, 1000-1350 nm and 1000-1200 nm, 1200-1700 nm, 1500-1550 nm. Each possibility represents a separate embodiment of the present disclosure. According to a non-limiting example, a suitable NIR laser radiation is produced by a pulsed neodymium-doped yttrium aluminum garnet (Nd:YAG) laser emitting radiation at a wavelength of 1064 nm.

According to some embodiments, the laser radiation is a pulsed laser radiation to initiate non-linear based interaction processes and non-linear energy absorption and interaction with the tissue. Without wishing to be bound by any theory or mechanism, short pulsed focused laser directed at a tissue may result in a non-linear interaction with the tissue such that plasma formation and/or photo-ablation occur only at a site in the tissue in which the energy peak at a given area has an energy flux high enough to cross a pre-determined threshold. According to some embodiments, photo-ablation in the presence of a high enough peak power in the focus area may be accompanied with some level, even if small, of absorption of the laser beam by the tissue. By this means, laser that is not absorbed or not strongly absorbed by the tissue might be used so that high energy is not significantly impacting the mucosal layer so as to not cross the flux threshold in areas on which the beam is not focused.

According to some embodiments, focused pulsed laser is configured not to be absorbed in tissue outside of the target area of the laser. According to some embodiments, focused pulsed laser is configured not to be significantly absorbed in tissue outside of the target area of the laser. According to some embodiments, significant absorbance of laser radiation in a tissue is absorbance configured to cause damage to the tissue. By mode of example, Q Switched Nd:YAG laser can be used to initiate damage at flux in the order of 50-250 mJ/mm2 using laser at 1064 nm with 5-10 nsec pulses. According to other embodiments, fluxes of 25-75 mJ/mm2 may be employed if a second harmonic 532 nm laser is used. This flux may be lower as the absorption in the tissue is significantly higher. According to some embodiments, non-focused laser is configured to be absorbed in target tissue. According to some embodiments, laser tissue is configured to be absorbed by target tissue such that following tissue is exposed to lower energy flux thus not ablating it. According to some embodiments, laser tissue is configured to affect target tissue and not affect deeper tissue by means of power setting of the laser generator. According to some embodiments laser tissue is configured to affect target tissue and not affect deeper tissue by means of controlling the speed of motion of laser beam. Without wishing to be bound by any theory or mechanism, these levels of fluxes with the above-mentioned lasers are able to cross a threshold of ablation that leads to chemical and/or mechanical distrubtion of the tissue and can cause direct or induced damage of the target area. Alternatively, lower fluxes may be used with shorter pulses that induce plasma formation in the target area even when the absorption is very low. This may lower the threshold fluence by more than an order of magnitude depending on the pulse width and be in the range of 1 mJ/mm2 with fsec pulses even when the linear absorption is negligible (Alexander A. Oraevsky et al, IEEE JOURNAL OF SELECTED TOPICS IN QUANTUM ELECTRONICS, VOL. 2, NO. 4, DECEMBER 1996). A laser beam that passes through a tissue below these fluence thresholds, according to some embodiments, will not initiate the non-linear related damages effects and will minimize impact and damage to tissue outside the target area, on which the laser is not focused.

According to some embodiments, focused pulsed laser is minimally linearly absorbed in tissue outside of the target area of the laser. According to some embodiments, focused pulsed laser is minimally absorbed in tissue outside of the target area of the laser such that tissue outside the target area is not damaged. According to some embodiments, focused pulsed laser is minimally absorbed in tissue outside of the target area of the laser such that tissue outside the target area maintains functional activity. According to some embodiments, using a pulsed laser prevents absorption or induced non-significant absorption of laser radiation in the mucosa and/or tunica muscularis of the duodenal wall. Each possibility represents a separate embodiment of the present disclosure. Non-limiting examples of lasers that may be used to produce such laser radiation include micro Q-Switched Nd:YAG lasers such as, but not limited to, those manufactured by Kigre (MK-367) that are very compact and produce a beam that may cross ablation threshold when sufficiently focused, standard flash pumped Q-Switched lasers (including those that are self Q-Switched), high repetition rate Solid State Diode Pumped Nd:YAG lasers, fiber lasers which use small spots to obtain a high enough peak power to cause damage or any combination thereof. Each possibility represents a separate embodiment of the present disclosure. Other non-limiting examples include CW, quasi CW or Q switched lasers. Appropriate lasers can be, for example, double YAG in 532 nm, or laser diode in 500-1000 nm range, a laser in the 1,400-2,000 nm range or Holmium/Thuliium lasers at ~2 microns.

According to some embodiments, focused pulsed laser is partially linearly absorbed in tissue outside of the target but the flux is higher at the target to elevate the temperature of tissue upon laser beam absorption to a higher temperature in the focus target area compared to the non-focus area.

Figure 3A:
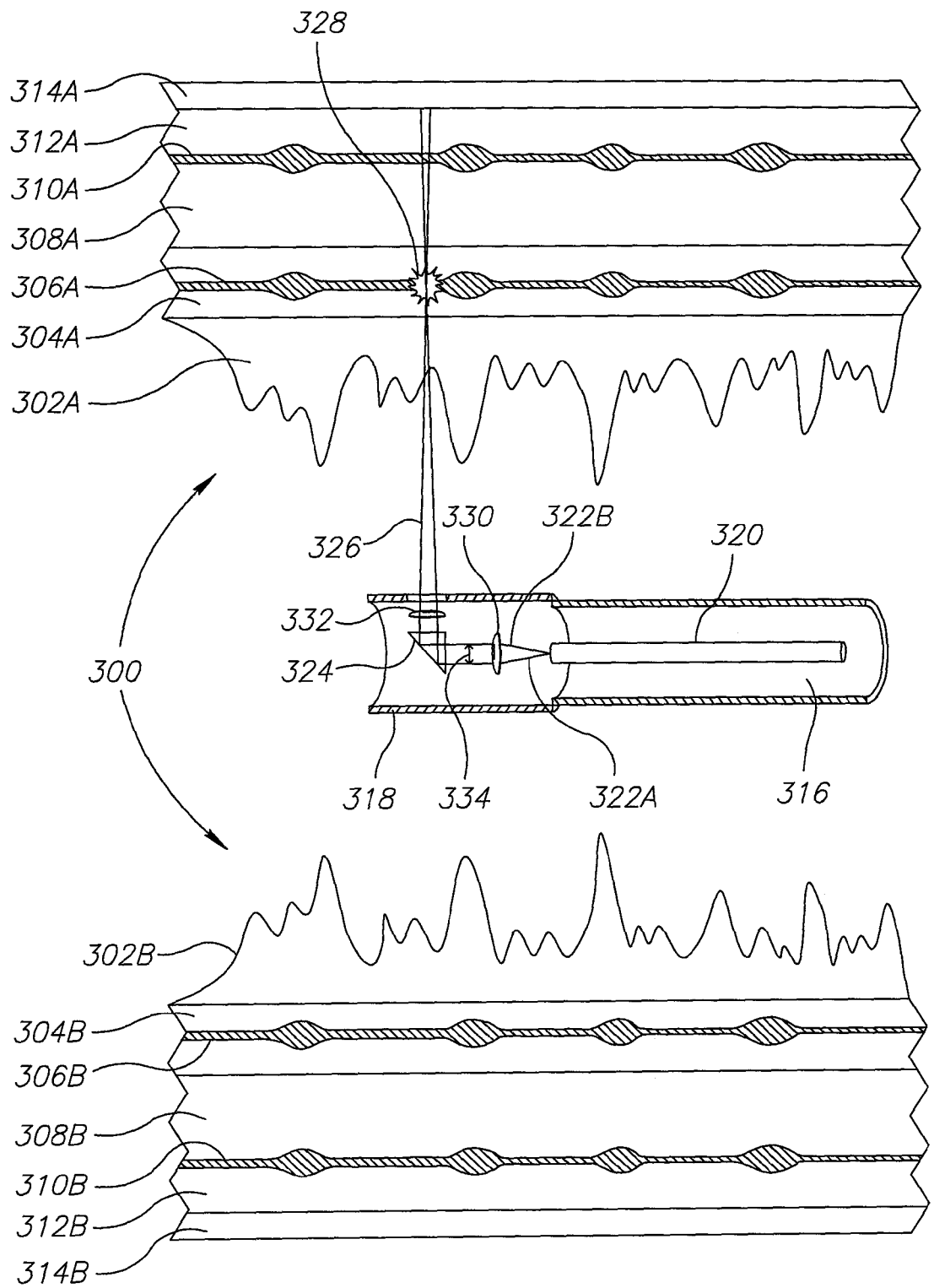
FIG. 3A schematically illustrates a longitudinal cross section through part of a duodenum and a catheter inserted within the lumen of the duodenum, according to some embodiments.

Reference is now made to FIG. 3A, illustrating, according to some embodiments, blocking of neural activity in the duodenal wall by use of laser radiation which is not configured to be significantly linearly absorbed in tissue outside the target area, according to some embodiments. FIG. 3A depicts a longitudinal cross section through part of duodenum (300) and catheter (316) which is introduced into the lumen of duodenum (300). The duodenum wall of duodenum (300) comprises the mucosal layer (302A, 302B), the submucosal layer (304A, 304B) which comprises submucosal plexus (306A and 306B, respectively), circular muscle (308A, 308B), myentric plexus (310A, 310B), longitudinal muscle (312A, 312B) and mesenteric layer (314A, 314B).

Catheter (316) comprises laser element (318) and optic fiber (320) which is partially comprised in laser element (318). Optic fiber (320) emits laser radiation (322A, 322B) which passes through collimating lens (330) and is then rotated by rotatable prism (324) and focused by focusing lens (332) such that focused laser radiation (326) is directed at target area (328). Target area (328) in the duodenal wall comprises part of the sensory neurons of submucosal plexus (306A). According to some embodiments, focusing lens (332) is configured to rotate together with the rotatable prism (324) and/or other means of reflection. According to some embodiments, collimating lens (330) is rotatable and is optionally part of the rotating laser element (318). According to some embodiments, laser element (318) further comprises at least one focusing element, such as, but not limited to, at least one lens (332), configured to focus laser radiation (326) at target area (328). According to some embodiments, the at least one focusing element is able to focus the laser radiation (326) at different angles, including, but not limited to, 0, 30, 45, 70, or 90 degrees from the longitudinal axis of the catheter (316), such that the laser radiation is configured to be directed at the desired target area.

According to some embodiments, laser radiation (326) is non-uniform such that the energy level of laser radiation (326) is the highest at target area (328) on which it is focused. According to some embodiments, laser radiation (326) is configured to induce nonlinear interaction with the tissue, such that the energy level of laser radiation (326) is only high enough to induce damage within target area (328) on which it is focused and not in surrounding tissue. Laser radiation (326) is laser radiation configured not to be absorbed or to be non-significantly absorbed in tissue. According to some embodiments, lens (332) is placed on a translator to enable control of focal plane. A typical focal length may be in the range of 2-25 mm, depending on the configuration. According to some embodiments, a typical beam diameter (334) of laser radiation (322A, 322B) is in the range of 1-20 mm. By mode of example, if a 5 mm collimated beam is obtained using collimating lens (330) for collimation of a Gaussian shape beam exiting from optic fiber (320), and a 15 mm focal lens is used as focusing lens (332), a spot in the range of 10 microns may be formed (depending on aberrations and scattering) with a focus depth in the range of tens of microns, thereby enabling localized damage. Each possibility represents a separate embodiment of the present disclosure.

According to some embodiments, laser radiation (326) is pulsed laser, quasi CW or CW laser or a combination thereof. Each possibility represents a separate embodiment of the present disclosure. According to some embodiments, laser radiation (326) is configured to induce damage only within target area (328) and to induce no damage or non-significant damage to mucosa (302A) which it passes in order to get to target area (328) and to duodenal layers (310A, 312A, 314A) which it passes after having arrived at target area (328). Each possibility represents a separate embodiment of the present disclosure.

According to some embodiments, laser radiation (326) is focused on target area (328) or, in some embodiments, its anatomical area (304A) and thus laser radiation (326) crosses the ablation threshold only within target area (328) or (304A), respectively. Each possibility represents a separate embodiment of the present disclosure.

According to some embodiments, laser radiation (326) is configured to have enough linear optical absorption to elevate tissue temperature upon absorption and yet not to be absorbed strongly at the surface to enable large enough penetration depth. By mode of example, a 808CW laser beam may be used as it is partially absorbed in a tissue but can effectively penetrate a few mm. Laser beam in the range of a 100 mW-10 Watts, depending on the spot size and illumination length, may be used to elevate the tissue temperature at the focal plane to a pre-determined thermal window such as 45-75 Celsius degrees. According to some embodiments, laser radiation (326) is focused on target area (328) and thus induces temperature elevation which results in thermal induced damage only within target area (328).

According to some embodiments, rotatable prism (324) and/or laser element (318) are configured to rotate and enable direction of laser radiation (326) to other target areas, such as, but not limited to a target area comprising part of the sensory neurons of submucosal plexus (306B). Each possibility represents a separate embodiment of the present disclosure.

According to some embodiments, rotatable prism (324) and/or laser element (318) are configured to rotate and enable direction of laser radiation (326) to several target areas, such as, but not limited to, a target area comprising part of the sensory and/or motility neurons in tunica muscularis layers such as myentric plexus (310B). Each possibility represents a separate embodiment of the present disclosure.

According to some embodiments, the laser radiation is configured to be focused on the target area via at least one aperture located in the wall of the catheter (316). According to some embodiments, the laser radiation is absorbable in the target area and tissue surrounding the target area. According to some embodiments, the laser radiation is focused on the target area such that it induces its main damage in the target area while minimizing its collateral impact on layers surrounding the target area.

According to some embodiments, the absorbable laser radiation is produced by a laser source selected from the group consisting of: continuous-wave (CW) laser, quasi continuous-wave laser, Q-switched laser and a combination thereof. Each possibility represents a separate embodiment of the present disclosure. According to non-limiting examples, the laser radiation is produced by a laser selected from the group consisting of: a double YAG laser emitting radiation at a wavelength of 532 nm, a laser diode emitting radiation at a wavelength of 808 nm-980 nm, a laser diode emitting radiation at a wavelength of 1500 nm, a 2 microns Holmium Thuliium and a combination thereof. Each possibility represents a separate embodiment of the present disclosure.

Figure 3B:
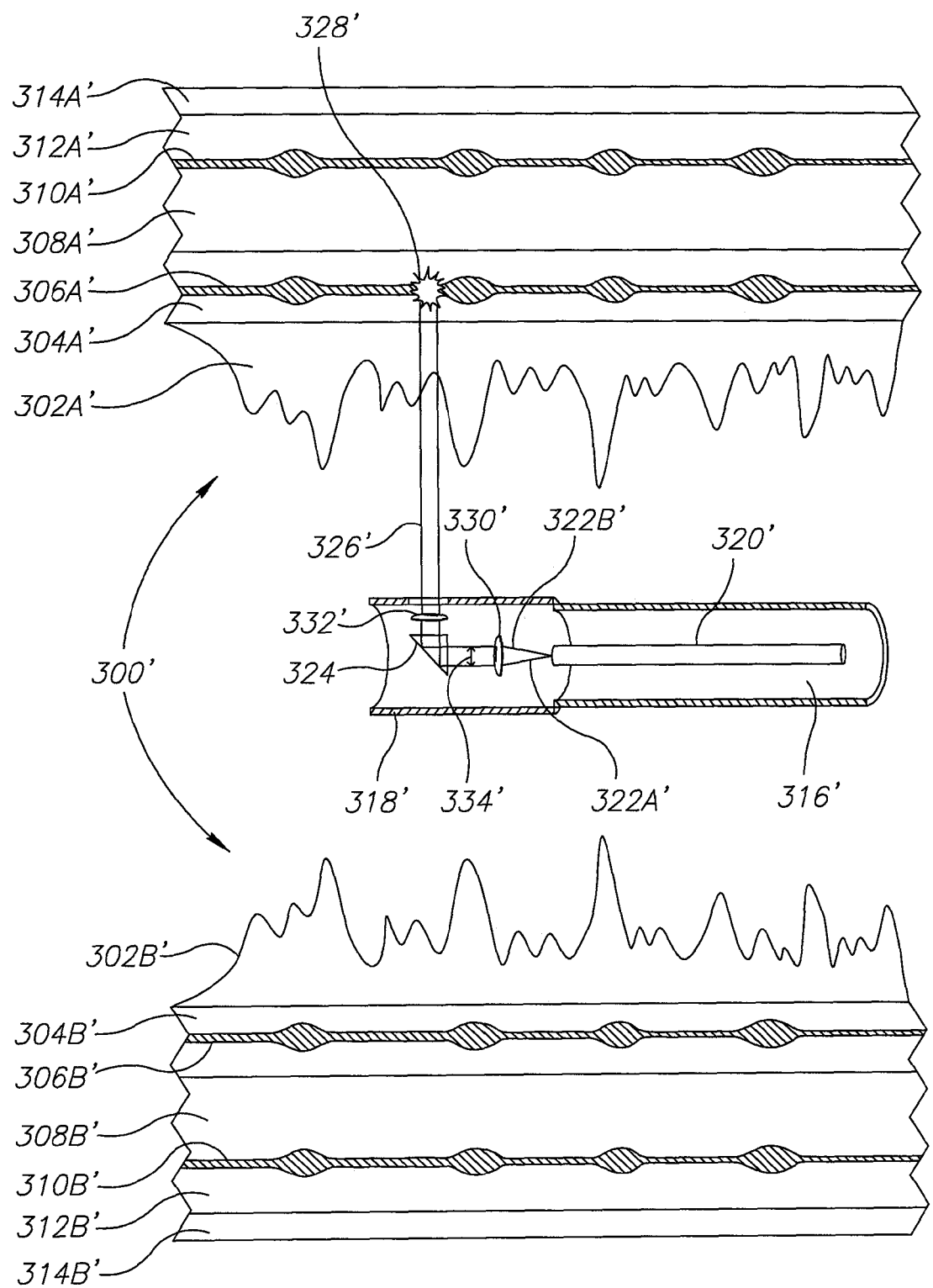
FIG. 3B schematically illustrates a longitudinal cross section through part of a catheter, according to certain embodiments.

According to some embodiments, the laser radiation is high power 808 nm radiation. According to some embodiments, a high power laser radiation such as an 808 nm radiation is configured to enable targeting a shape such as a longitudinal line across the duodenum simultaneously. According to the embodiment illustrated in FIG. 3B, targeting a shape such as a longitudinal line across the duodenum simultaneously may be achieved by passing laser radiation through cylindrical lens (332') directing laser radiation (226') at target area (328'). According to some embodiments, targeting a shape such as a longitudinal line across the duodenum simultaneously is directed at a focal plane in the peripheral wall of the duodenal wall to target interface of the duodenum with ganglia and/or vagal nerves and/or the VAN interface. Each possibility represents a separate embodiment of the present disclosure. Of note, other than cylindrical lens (332') and laser radiation (226'), all elements in FIG. 3B correspond to elements in FIG. 3A.

According to some embodiments, such laser radiation produced by a laser source such as CW or quasi CW or pulsed laser may be focused on the outer layers of the duodenal wall using optics. Alternatively, this can be done by using a focused beam longitudinally which is moved in a line pattern across the duodenum or by moving the laser element across the duodenum. According to other embodiments, a line spot may be focused on the target area and rotated around the lumen axis by using a cylindrical lens, as exemplified in FIG. 3B in which cylindrical lens (332') is focused on a focal plane parallel to the rotation axis. Each possibility represents a separate embodiment of the present disclosure. According to some embodiments, a laser such as an high power 808 nm laser might be used that so as to enable the exposure of a longitudinal line across the duodenum simultaneously; such as, the use of CW or quasi CW illumination; wherein optics is used to focus the beam at the outer section of the duodenum wall.

According to another embodiment, the laser radiation is produced by a laser that is coupled to a series of fibers (which form a bundle) illuminating at different length or using cylindrical diffusing fibers (such as MedLight Cylindrical light diffuser Model RD) combined with a reflector and cylindrical lens to get illumination in part of a circle. Embodiments based on such a fibers can be used also in combination with previous embodiments to create a circle like impact or to create a spiral or helical like impact. In another embodiment an array of laser diodes can be used to simultaneously direct laser radiation to the target area.

According to some embodiments, the damage induced by the laser radiation at the target area is higher than that induced in its surrounding. Without wishing to be bound by any theory or mechanism, the damage induced by the laser radiation at the target area is higher than that induced in its surrounding due to a higher temperature elevation at the target area. According to some embodiments, the damage induced by the focused laser radiation in its optical path is smaller than the damage induced at the focal plane of the focused laser radiation. According to some embodiments, the damage induced by the laser radiation at the target area is higher than that induced in its surrounding despite intensity attenuation and/or absorption and/or scattering of the laser radiation. Each possibility represents a separate embodiment of the present disclosure. According to some embodiments, the focal plane of the focused laser radiation is at the target area of the laser radiation.

In yet another embodiment, a 2.9 laser with free running pulses ranging from micro-hundreds of seconds to microseconds (such as 3 Mikron Er:YAG lasers) or a pico-sec (such as PIRL manufactured by Attodyne Lasers) or nano-sec laser can be used to generate very thin controlled cuts in the duodenal wall by ablation. Controlled cuts may be performed with other lasers such as, but not limited to, Thulmium or 355 nm. According to some embodiments, a second laser may be used in conjunction with the laser source producing the disclosed laser radiation in order to facilitate coagulation. According to some embodiments laser cutting of sub-mucosal plexus can be accompanied with energy induced damage of neural elements in the tunica muscularis with mechanical cutting to avoid wall perforation. According to some embodiments, mechanical cutting depth is determined by imaging. According to some embodiments, the controlling and imaging cutting depth is done in real time.

IV. LASER ABSORPTION IN TARGET AREA TISSUE AND TISSUE OUTSIDE OF TARGET AREA

Figure 4:
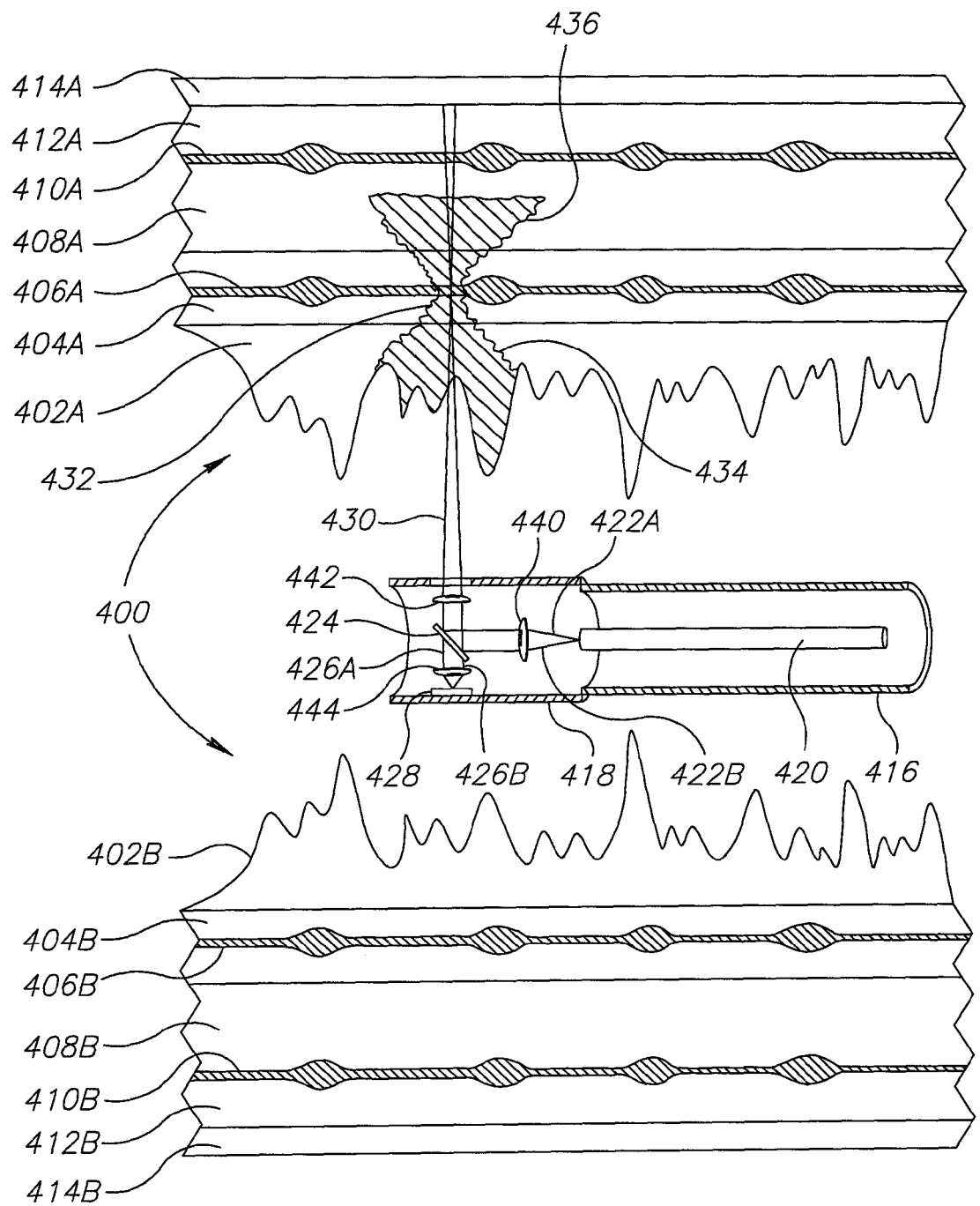
FIG. 4 schematically illustrates a longitudinal cross section through part of a duodenum and a catheter inserted within the lumen of the duodenum, according to some embodiments.
Figure 4B:
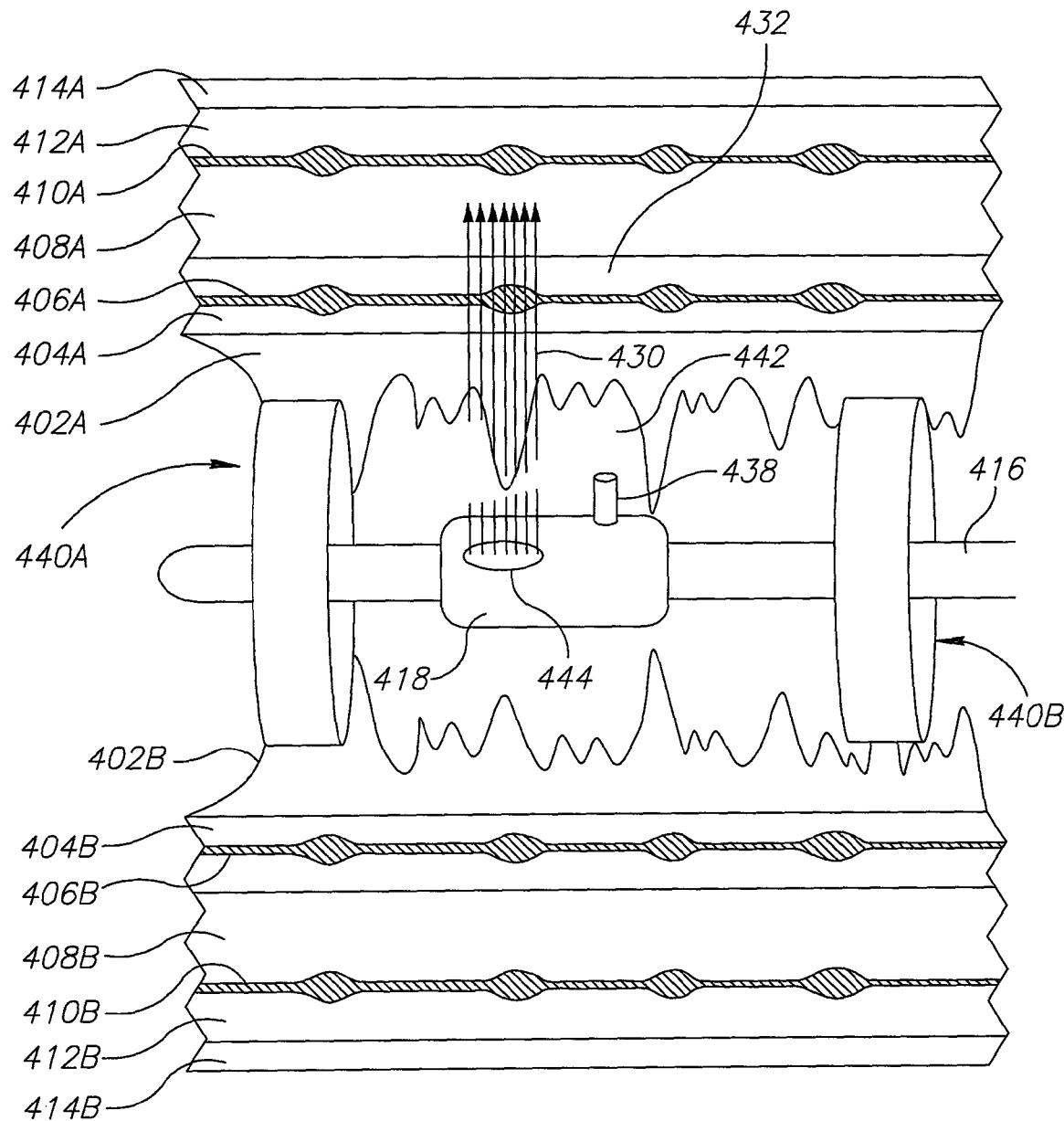
FIG. 4B schematically illustrates a longitudinal cross section through part of a duodenum and a catheter inserted within the lumen of the duodenum with stretch/confining devices at it proximal and distal sides, mucosal coolant, and non-focused laser radiation, according to some embodiments.
Figure 4C:
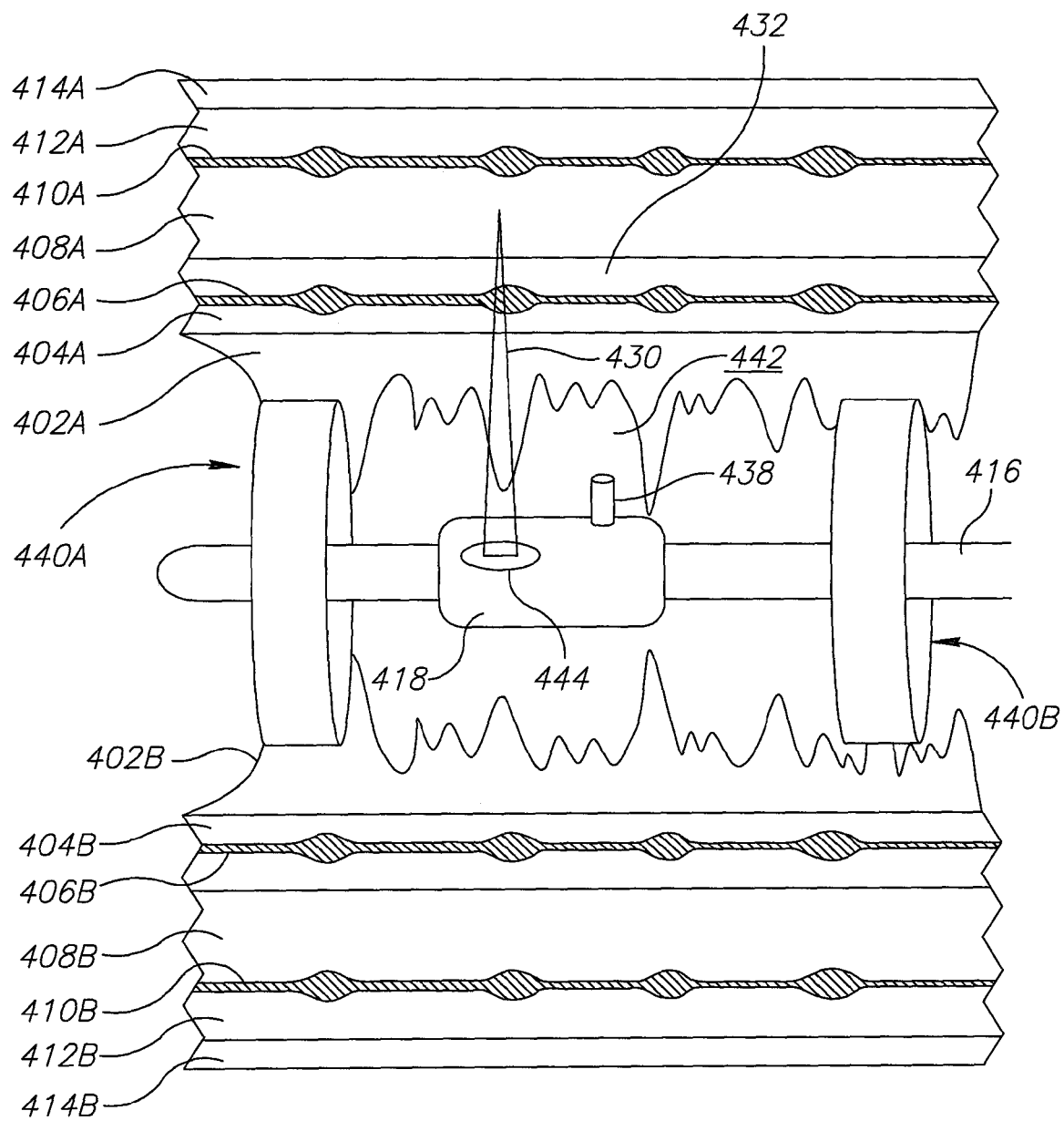
FIG. 4C schematically illustrates a longitudinal cross section through part of a duodenum and a catheter inserted within the lumen of the duodenum with stretch/confining devices at it proximal and distal sides, mucosal coolant, and focused laser radiation, according to some embodiments.

Reference is now made to FIGS. 4, 4B & 4C, illustrating, according to some embodiments, blocking of neural activity in the duodenal wall by use of laser radiation which can be absorbed in tissue outside the target area. FIG. 4 depicts a longitudinal cross section through part of duodenum (400) and catheter (416) which is introduced into the lumen of duodenum (400), according to some embodiments. The duodenum wall of duodenum (400) comprises the mucosal layer (402A, 402B), the submucosal layer (404A, 404B) which comprises submucosal plexus (406A and 406B, respectively), circular muscle (408A, 408B), myentric plexus (410A, 410B), longitudinal muscle (412A, 412B) and mesenteric layer (414A, 414B).

Catheter (416) comprises laser element (418) and optic fiber (420) which is partially comprised in laser element (418). According to some embodiments, laser element (418) is rotatable. Optic fiber (420) emits laser radiation (422A, 422B) which is collimated by lens (440) and manipulated by rotatable beam splitter (424) such that the laser radiation (430) is either emitted through an overture in the laser element or is focused through lens (442) at target area (432) in the duodenal wall. Target area (432) comprises part of the sensory neurons of submucosal plexus (406A). Laser radiation (426A, 426B) which is back reflected and/or scattered is directed at imaging element (428) through lens (444). Imaging element (428) may be a camera or any imaging element known in the art. According to some embodiments, lens (440) may be used to generate the desired focus at the target area, obviating the need for lens (442).

According to some embodiments, laser element (418) further comprises at least one focusing element on a translator to align focal point, such as, but not limited to, at least one lens (442), configured to focus laser radiation (430) at target area (432). According to some embodiments laser element (418) may be used in the lumen of the duodenum or other lumens to create a series of impacts. According to some embodiments, lens (442) is a cylindrical lens which creates a line spot perpendicular to the lumen axis and is optionally rotated in steps in order to create a circular impact in a cross-sectional plan of the duodenum perpendicular to the lumen axis.

According to some embodiments the target is other layers such as mulscularis or periphery of duodenum.

According to some embodiments, the energy level of laser radiation (430) is the highest at target area (432) on which it is focused. According to a non-limiting example, a spot 100 micron in diameter of a 1 Watt a CW laser at 808 nm is obtained at the target to elevate the temperature by a few seconds to tens of seconds of illumination of the target area to induce damage. According to some embodiments, laser radiation (430) is absorbed in areas (434) and (436) surrounding target area (432) wherein the temperature elevation induced is maintained below that which induces damage within the illumination period. According to some embodiments, the energy level provided to duodenal tissue by laser radiation (430) is higher in target area (432) than in areas (434) and (436). According to some embodiments, the damage induced by laser radiation (430) is higher in target area (432) than in areas (434) and (436). According to some embodiments, the thermal damage induced by laser radiation (430) is higher in target area (432) than in areas (434) and (436). According to some embodiments, the temperature elevation induced by laser radiation (430) is higher in target area (432) than in areas (434) and (436). According to some embodiments, the temperature elevation induced by laser radiation (430) is higher in target area (432) than in areas (434) and (436) such that thermal damage is induced only in target area (432) and not in areas (434) and (436). According to some embodiments, the ablation induced by laser radiation (430) is higher in target area (432) than in areas (434) and (436). According to some embodiments, the energy transferred to duodenal tissue by laser radiation (430) is higher in target area (432) than in areas (434) and (436) such that it is high enough to induce ablation in target area (432) and not in areas (434) and (436). According to some embodiments, the affect induced by laser radiation (430) is higher in target area (432) than in areas (434) and (436), so as to cause a physical effect in the target area (432), but not in areas (434) and (436).

FIG. 4B depicts the longitudinal cross section depicted in FIG. 4 with the catheter (416) comprising laser element (418), according to some embodiments. According to some embodiments, the laser radiation (430) is emitted through an overture (444) in the laser element at target area (432) in the duodenal wall. Target area (432) comprises part of the sensory neurons of submucosal plexus (406A). According to some embodiments the catheter (416) further comprises a cooling element (438) as well as means or devices for stretching or confining the section of the duodenal lumen to be treated (440A, 440B). According to some embodiments the means or devices for stretching or confining the section of the duodenal lumen to be treated include inserting of a balloon at the distal part (440A) and in some embodiments in the proximal part (440B).

FIG. 4C depicts the longitudinal cross section depicted in FIG. 4B with the catheter (416) comprising laser element (418), according to some embodiments. According to some embodiments, the laser radiation (430) is emitted through an overture (444) in the laser element and is focused at target area (432) in the duodenal wall. Target area (432) comprises part of the sensory neurons of submucosal plexus (406A). According to some embodiments the catheter (416) further comprises a cooling element (438) as well as means or devices for stretching or confining the section of the duodenal lumen to be treated (440A, 440B). According to some embodiments the means or devices for stretching or confining the section of the duodenal lumen to be treated include inserting of a balloon at the distal part (440A) and in some embodiments in the proximal part (440B).

According to some embodiments such cooling element (438) include, but are not limited to, a tube used to infuse or irrigate the treatment field with biocompatible coolant (442) prior to the application of laser energy to the tissue so as to shield the tissues, components and layers thereof surrounding the target area from thermal damage or minimize its effects. According to some embodiments the biocompatible coolant includes chilled physiological solution with non-limiting examples of such physiological solution include water or physiological saline. Other biocompatible coolants include, but are not limited to chilled biocompatible and/or biodegradable gels such as hyaluronic acid, glycosaminoglycan-based gels, polysaccharide hydrogels, and additional natural & synthetic hydrogels known in the art. According to some embodiments the tissue, components and layers thereof surrounding the target area is the mucosal layer (434) including the villous (villi) structures and additional structural-functional components contained therein. According to some embodiments means to fill the lumen are to be targeted/treated include inserting of a balloon at the distal part and in some embodiments in the proximal part such that the lumen can be filled with cooled liquid or gas and in some embodiment even pressurized to achieve a pre-determined diameter to facilitate optical alignment.

According to some embodiments, the laser radiation is configured to cause damage to at least part of the sensory nerves within the target area while maintaining functional activity of tissue surrounding the sensory nerves. According to some embodiments, the laser radiation is configured to cause damage to at least part of the sensory nerves within the target area while maintaining functional activity of tissue surrounding the sensory nerves within the target area.

According to some embodiments, the laser radiation is configured to cause damage to at least part of the nerves within the target area while maintaining functional activity of tissue surrounding the nerves within the target area. According to some embodiments, the laser radiation is configured to cause damage to at least part of the sensory nerves within the target area while maintaining functional activity of tissue surrounding the target area. According to some embodiments, the damage is acute sub-ablative damage. According to some embodiments, inducing acute sub-ablative damage to nerves leads to a series of biochemical steps culminating in neural cell death. According to some embodiments, efferent neurons are able to recover from damage induced according to the present disclosure. According to some embodiments, efferent neurons are able to recover from damage induced according to the present disclosure such that they maintain their functional activity.

According to some embodiments, the damage to the neurons is selected from the group consisting of: thermal damage, ablation, mechanical damage and a combination thereof. Each possibility represents a separate embodiment of the present disclosure. According to some embodiments, one type of damage to the neurons is denervation. According to some embodiments, the damage significantly reduces or completely abrogates neural activity of sensory neurons within the target area. Each possibility represents a separate embodiment of the present disclosure. According to some embodiments, the damage results in cutting and/or removing of at least part of the sensory neurons in the target area. Each possibility represents a separate embodiment of the present disclosure. According to some embodiments, the damage prevents propagation of neural signal within neurons and/or synapses at the target area. Each possibility represents a separate embodiment of the present disclosure.

V. DAMAGE TO TARGET AREA

According to some embodiments, damage to sensory neurons in at least one target area within an organ of a subject, such as a subject's duodenum and/or within or in contact with at least part of a duodenal wall results in blocking at least part of the signals generated in the target area such as but not limited to those induced by food passage through the duodenum. According to some embodiments, the signals induced by food passage through the duodenum are signals induced by chemo-receptors and/or mechano-sensors within the duodenal wall. Each possibility represents a separate embodiment of the present disclosure. According to some embodiments, damage to sensory neurons in at least one target area within or in contact with at least part of a duodenal wall results in modulation of motility in at least part of the gastrointestinal (GI) tract. According to some embodiments, modulation of motility refers to at least one of modulation of gastric accommodation and relaxation triggered by meal passing through the duodenum and/or stomach. Each possibility represents a separate embodiment of the present disclosure. According to certain embodiments, the present disclosure provides a method for blocking at least part of sensory neurons activated by passage of food through the jejunum.

According to some embodiments, the damage is achieved by a single burst of the laser radiation towards the target area. According to some embodiments, the damage is achieved by a plurality of bursts of the laser radiation towards the target area. As used herein, the term "plurality" refers to at least two. According to some embodiments, the plurality of bursts of laser radiation are provided uniformly in time. According to some embodiments, the plurality of bursts of laser radiation are provided with uniform intensity. According to some embodiments, the plurality of bursts of laser radiation are provided in varying amounts of time. According to some embodiments, the plurality of bursts of laser radiation are provided with varying intensity. According to some embodiments, a beam compressor or a pulse compressor is used in conjunction with the elements used to rotate, manipulate or scan the beam. According to some embodiments, focusing the laser radiation on the target area induces damage in a form selected from the group consisting of: a straight line, a curved line, a circle, a circle sector, a helix, a dot, a spot and a combination thereof. Each possibility represents a separate embodiment of the present disclosure. In certain embodiments, damage to a target area, such as, but not limited to, the submucosal plexus is induced by focusing the laser radiation to a plurality of locations along the target area. Without wishing to be bound by any theory or mechanism, focusing the laser radiation to a plurality of locations along a target area may facilitate impacting the target area while minimizing side effects and/or damage to surrounding tissue.

According to some embodiments, the laser radiation is configured to cause damage to neurons within the target area with causing no damage or minimal damage to tissue surrounding the neurons in the target area. Each possibility represents a separate embodiment of the present disclosure. According to some embodiments, the laser radiation is configured to cause damage to sensory neurons within the target area with causing no damage or minimal damage to tissue surrounding the sensory neurons in the target area. According to some embodiments the tissue surrounding the target area is shielded from the thermal effects of the laser radiation. According to some embodiments the thermal shield to the tissue surrounding the target area is provided by cooling of the tissue. According to some embodiments the surrounding tissue is the mucosal tissue or layer and components thereof including, but not limited to, the villi. Each possibility represents a separate embodiment of the present disclosure.

According to some embodiments, nerves are more sensitive to thermal damage than tissues such as, but not limited to, vasculature, muscle and lymphatic vessels. According to some embodiments, exposing nerves to a temperature of about 45-75° C. for approximately 10 seconds or 20 seconds or 30 seconds induces thermal damage to the nerves. According to some embodiments, exposing nerves to a temperature of about 45-55° C., 55-75° C. or 60-75° C. for durations of approximately 0.1 second, 1 second, 5 seconds, 10 seconds, 30 seconds, 1 minute, 5 minutes or 10 minutes induces thermal damage to the nerves by a short exposure of less than a minute typically. Each possibility represents a separate embodiment of the present disclosure.

According to some embodiments, thermal damage to nerves significantly reduces or abrogates neural activity in the nerves. According to some embodiments, exposure of nerves to heat of at least about 60° C., typically at least about 65° C. degrees for about 30-60 seconds, typically about 20-50, 10-40 or 5-30 seconds is sufficient to induce thermal damage in the nerves. Each possibility represents a separate embodiment of the present disclosure. It is to be noted that inducing thermal heat in nerves using high temperatures may be done in seconds, while inducing thermal heat using lower temperature may require several minutes. The time required to induce temperature elevation at the target area may be less than a minute when temperature such as 65° C. are reached, may be above 10 minutes at lower temperatures or may be seconds at higher temperatures. Without wishing to be bound by any theory or mechanism, exposing a target area comprising neurons to laser energy may induce thermal damage in nerves prior to damaging other tissues within the target area. Accordingly, focusing laser radiation to a target area may be used to induce thermal damage to neurons within the target area without inducing damage to other tissues within the target area. Without wishing to be bound by any theory or mechanism, exposing a target area comprising neurons to laser energy may induce thermal damage while the cooling of surrounding or adjacent tissue may shield said tissue from the thermal damage induced by the laser energy. Accordingly, cooling of the mucosal surface may be used to spare the mucosa from the thermal effects induced within or at the target area or diminish its effect and maintain its structural integrity and functional activity.

VI. METHODS AND SYSTEMS FOR TREATING A MEDICAL CONDITION

According to some embodiments, the present disclosure provides a method for treating a medical condition selected from the group consisting of: obesity, type 2 diabetes mellitus, insulin resistance and a combination thereof in a subject, the method comprising:
 introducing at least one laser element into a lumen of the subject's duodenum;
 actuating the laser element to emit laser radiation;
 focusing the laser radiation to a target area within or in contact with at least part of a duodenal wall, wherein the target area comprises sensory nerves, such that the radiation is configured to cause damage to at least part of the sensory nerves while maintaining functional activity of tissue surrounding the sensory nerves.

According to some embodiments, the disclosed method of treatment is configured to modulate selective and local signals induced by food and/or physiological functions associated with food ingestion. According to some embodiments, interventions, such as damage induced by laser radiation, may be performed at several locations along the duodenal wall and/or in contact with the duodenal wall in order to target pathways and sensors spread across the various layers of the duodenal wall and to affect various mechanisms involved in conditions such as, but not limited to, type 2 diabetes and obesity. According to some embodiments, one or more locations along the duodenum can be impacted according to the disclosed methods. According to some embodiments, locations proximal to the duodenum such as the distal gastric region and/or pylorus of the stomach may be impacted. According to some embodiments, locations distal to the duodenum such as the duodenal-jejunal junction and the jejunum may be impacted. According to some embodiments, the term "impacted" refers to an area on which laser radiation is focused. According to some embodiments, the term "impacted" refers to an area comprising sensory neurons on which laser radiation is focused.

According to another aspect, the present disclosure provides an endoluminal duodenal catheter for blocking at least part of the neural activity in a duodenum of a subject in need thereof, the catheter comprising:
 a laser element configured to emit laser radiation; and
 a rotatable optical element configured to direct the laser radiation to one or more target areas within or in contact with at least part of a duodenal wall, wherein the target area comprises sensory nerves, such that the radiation is configured to cause damage to sensory nerves while maintaining functional activity of tissue surrounding the sensory nerves.

According to some embodiments, at least a part of a laser element is configured to emit laser radiation.

According to some embodiments, the catheter comprises a laser element configured to emit laser radiation. According to some embodiments, the catheter further comprises a laser source functionally connected to the laser element. According to some embodiments, the laser element comprises at least one optic fiber configured to emit laser radiation. According to some embodiments, the laser element comprises at least one focusing element configured to focus the laser radiation to the target area. According to some embodiments, the catheter further comprises at least one mechanical element configured to induce damage, such as, but not limited to, a blade, a rotating knife and a combination thereof. According to some embodiments the catheter further comprises means of delivering a cooling or thermal shielding material to tissues, components or layers thereof surrounding the target area. Such means of delivery may include but are not limited to, a tube configured to deliver coolant material to tissues, components or layers thereof surrounding the target area. Non limiting examples of such coolant material include biocompatible coolant such as chilled physiological solutions and biocompatible gels. Non-limiting examples of such physiological solutions may include water or physiological saline; and non-limiting biocompatible and/or biodegradable gels may include hyaluronic acid, glycosaminoglycan-based gels, polysaccharide hydrogels, and additional natural & synthetic hydrogels known in the art. According to some embodiments said tissue, components and layers thereof surrounding the target area is the mucosal layer including the villous (villi) structures and additional structural-functional components contained therein.

VII. PRESSURE-INDUCING ELEMENT

According to some embodiments, the endoluminal duodenal catheter further comprises at least one pressure-inducing element. According to other embodiments, the disclosed system comprises at least one pressure-inducing element. According to some embodiments, the at least one pressure-inducing element is configured to exert pressure on at least part of the duodenal wall. According to some embodiments, the at least one pressure-inducing element is configured to exert pressure on at least part of the duodenal wall and stretch it benefiting from its compliant structure. According to some embodiments, the at least one pressure-inducing element is configured to exert pressure on at least part of the duodenal wall thus controlling the distance between the target area and optical axis and determining the optical path length. According to some embodiments, the at least one pressure-inducing element is configured to exert pressure on at least part of the duodenal wall thus changing thickness of the duodenal wall or part thereof. According to some embodiments, changing thickness of the duodenal wall or part thereof enables to shorten the optical path of the laser radiation and/or bring the target area to a desired thickness. Each possibility represents a separate embodiment of the present disclosure. According to some embodiments, the at least one pressure-inducing element is configured to hold the laser element in place and/or to fix the laser element in a predetermined location. According to some embodiments, the at least one pressure-inducing element is in the form of a balloon. Without wishing to be bound by any theory or mechanism, exerting pressure on the duodenal wall using at least one pressure-inducing element may serve to overcome the inter and intra patient variability in the thickness and/or shape of the duodenal wall layers that may induce alteration in laser absorption and/or heat transfer interaction at the targeted layer.

According to some embodiments, the at least one pressure-inducing element is functionally connected to the catheter and/or laser element. Each possibility represents a separate embodiment of the present disclosure. According to some embodiments, the at least one pressure-inducing element surrounds and/or connected to at least part of the catheter/and or laser element. Each possibility represents a separate embodiment of the present disclosure. According to some embodiments, the at least one pressure-inducing element comprises at least part of the laser element. According to a non-limiting example, the pressure-inducing element is a balloon comprising at least part of the laser element.

According to some embodiments, the pressure-inducing element is constructed from polymers that have high transparency configured to enable passage of laser radiation through the pressure-inducing element and withstand high-power laser radiation. According to some embodiments, the pressure-inducing element is made of at least one polyamide. Non-limiting examples of polyamides that may be used for construction of the pressure-inducing element are disclosed in the technical document found at web-address http://www2.basf.us//PLASTICSWEB/displayanyfile?id=0901a5e180004886.

Figure 5A:
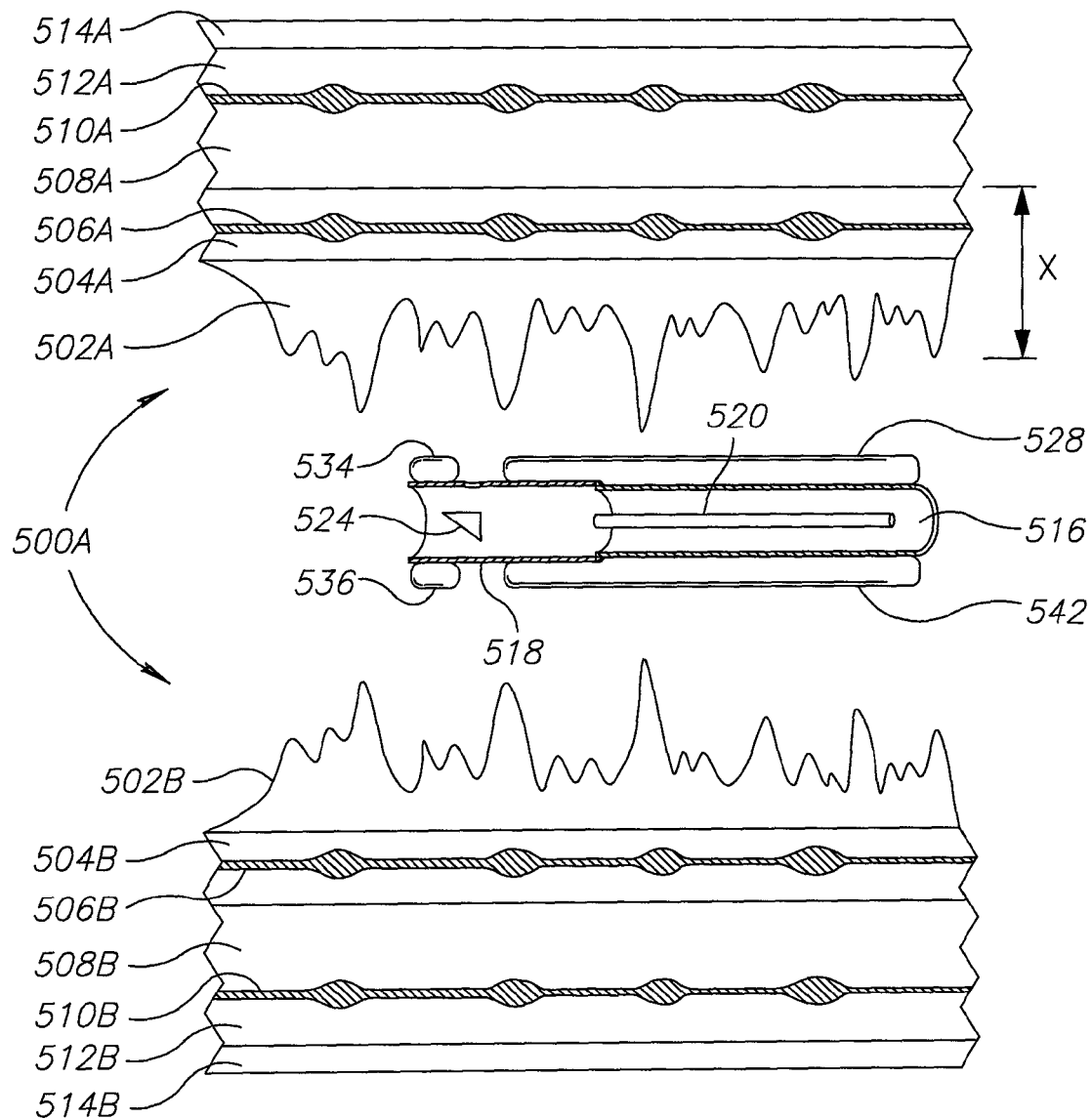
FIG. 5A schematically illustrates, according to some embodiments, a catheter which is inserted into the lumen of a duodenum comprising a laser element and deflated balloons.
Figure 5B:
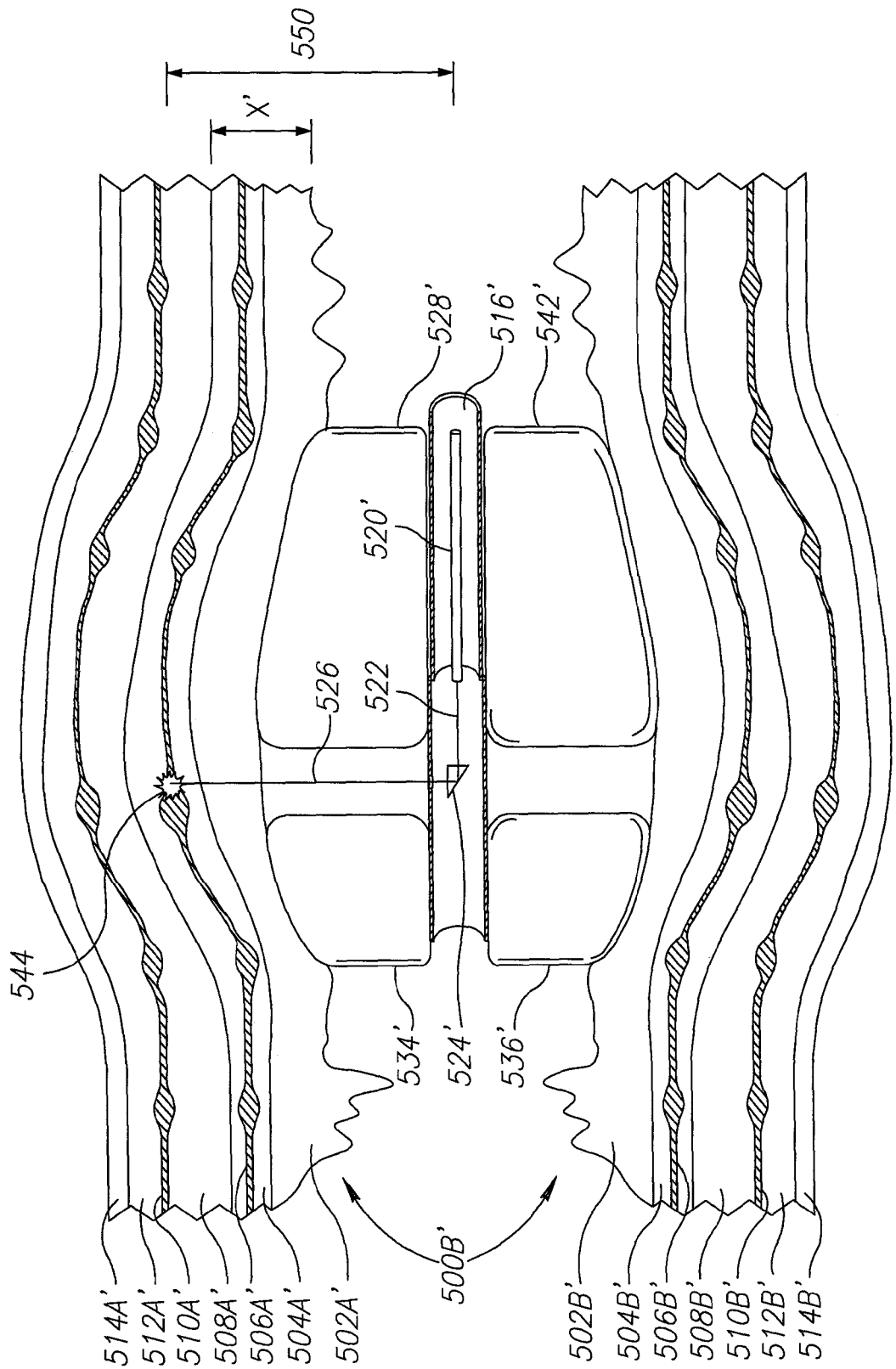
FIG. 5B schematically illustrates, according to some embodiments, a catheter which is inserted into the lumen of a duodenum comprising a laser element and inflated balloons which exert pressure on the duodenal wall.

Reference is now made to FIGS. 5A and 5B illustrating, according to some embodiments, a catheter comprising pressure inducing elements in the form of balloons.

FIG. 5A depicts a longitudinal cross section through part of duodenum (500A) and catheter (516) which is introduced into the lumen of duodenum (500A). The duodenal wall of duodenum (500A) comprises the mucosal layer (502A, 502B), the submucosal layer (504A, 504B) which comprises submucosal plexus (506A and 506B, respectively), circular muscle (508A, 508B), myentric plexus (510A, 510B), longitudinal muscle (512A, 512B) and mesenteric layer (514A, 514B), according to some embodiments. FIG. 5B depicts the longitudinal cross section depicted in FIG. 5A after deflated pressure-inducing elements (528, 534, 536, and 542) have been inflated to pressure-inducing elements (528', 534', 536', and 542') and induced pressure on the duodenal wall of duodenum (500B), according to some embodiments. Accordingly, FIG. 5B depicts a longitudinal cross section through part of duodenum (500B) and catheter (516') which is introduced into the lumen of duodenum (500B). The duodenal wall of duodenum (500B) comprises the mucosal layer (502A', 502B'), the submucosal layer (504A', 504B') which comprises submucosal plexus (506A' and 506B', respectively), circular muscle (508A', 508B'), myentric plexus (510A', 510B'), longitudinal muscle (512A', 512B') and mesenteric layer (514A', 514B').

Catheter (516) comprises laser element (518) and optic fiber (520) which is partially comprised in laser element (518). Laser element (518) is not-actuated such laser radiation is not emitted. Optic fiber (520) is configured to emit laser radiation directed at rotatable prism (524) such that focused laser radiation is directed at a target area in the duodenal wall. Catheter (516) and laser element (518) comprise pressure-inducing elements (528, 534, 536, and 542) in the form of balloons which are deflated and do not induce pressure on the duodenal wall of duodenum (500A). According to some embodiments, Laser element (518) is configured to be actuated only once pressure-inducing elements (528, 534, 536, and 542) have been inflated and induced pressure on the duodenal wall. According to some embodiments, Laser element (518) is configured to be actuated only once pressure-inducing elements (528, 534, 536, and 542) have inflated and induced pressure on the duodenal wall such that pre-determined optical path length distance (550) is achieved. According to certain embodiments, a controller is used to control actuation of deflated pressure-inducing elements (528, 534, 536, and 542).

Following inflation of deflated pressure-inducing elements (528, 534, 536, and 542) to pressure-inducing elements (528', 534', 536', and 542'), pressure was induced on duodenal wall of duodenum (500B) such that the thickness of duodenal wall layers is reduced. According to some embodiments, deflated pressure-inducing elements (528, 534, 536, and 542) are inflated to pressure-inducing elements (528', 534', 536', and 542') until pre-determined optical path length (550) is reached. According to some embodiments, submucosal layer (504A) and mucosal layer (502A) having thickness (X) turn into submucosal layer (504A') and mucosal layer (502A') having lower thickness (X') following the pressure induced by inflated pressure-inducing elements (528', 534', 536', and 542'). Concomitantly or following inflation of pressure-inducing elements (528', 534', 536', and 542'), optic fiber (520'), comprised in laser element (518'), emits laser radiation (522) which is rotated by rotatable prism (524') such that laser radiation (526) is directed at target area (544) comprising part of submucosal plexus (506A'). According to some embodiments, due to the pressure exerted on the wall of duodenum (500B) by inflated pressure-inducing elements (528', 534', 536', and 542') at least layers (502A') and (504A') are thinner and thus the optical path of laser (526) is shortened and less subject to variability in shape of villi mucosal surface. According to some embodiments, catheter (516') may be repositioned by deflating inflated pressure-inducing elements (528', 534', 536', and 542'), moving catheter (516') and re-inflating the pressure-inducing elements at the desired position.

According to some embodiments laser element (518) is located inside a transparent balloon which enables passage of laser radiation such that there is no need for an opening in the balloon. According to some embodiments the laser element can move along the lumen axis inside the balloon with no need to move the balloon to generate impact in several places along the lumen axis.

According to some embodiments the laser element is positioned in place by a tripod. In some embodiments the tripod is used to stretch the duodenum to predetermine optical distance (550).

According to certain embodiments, the pressure-inducing elements are inflated via air or via an inert gas. According to certain embodiments, the pressure-inducing element is filled with liquid to facilitate acquisition of acoustic wave associated with the photo-acoustic effect for purpose of optical alignment and/or on-line process monitoring. In certain embodiments, at least one acoustic transducer is assembled within the catheter. According to some embodiments the pressure-inducing element is filled with liquid to facilitate acquisition of acoustic wave associated with the photo-acoustic effect for purpose of optical alignment and/or on-line process monitoring with said liquid further used for cooling or thermal shielding of the tissues, components or layers thereof surrounding the target area. Non limiting examples of such coolant material include biocompatible coolants such as chilled physiological solutions and biocompatible gels which enables passage of laser radiation. According to some embodiments said tissue, components and layers thereof surrounding or adjacent to the target area is the mucosal layer (502A, 502B) including the villous (villi) structures and additional structural-functional components contained therein.

According to some embodiments, the present disclosure provides the disclosed endoluminal duodenal catheter for use in blocking at least part of the neural activity in a duodenum of a subject in need thereof. According to some embodiments, the present disclosure provides the disclosed endoluminal duodenal catheter for use in treatment of a medical condition selected from the group consisting of: obesity, type 2 diabetes, insulin resistance and a combination thereof in a subject.

According to another aspect, the present disclosure provides a system for use in blocking at least part of the neural activity in at least one neural region in a duodenum of a subject in need thereof, the system comprising:

an endoluminal duodenal catheter for blocking at least part of the neural activity in a duodenum of a subject in need thereof, the catheter comprising:
at least a part of a laser element configured to emit laser radiation; and
a rotatable optical element configured to direct the laser radiation to one or more target areas within or in contact with at least part of a duodenal wall, wherein the target area comprises sensory nerves, such that the radiation is configured to cause damage to sensory nerves while maintaining functional activity of tissue surrounding the sensory nerves;
an imaging device configured to capture structural information related to the duodenal wall or an area in contact with at least part of a duodenal wall; and
a controller configured to determine said one or more target area based on the structural information.

VIII. OPTICAL LENS SYSTEMS AND BEAM-SPLITTING OF LASER ELEMENT

According to some embodiments, the methods and systems use an optical element. According to some embodiments, the optical element is a rotatable optical element. According to some embodiments, the rotatable optical element is a wide-angle lens system. According to some embodiments, the rotatable optical element is a lens capable of correcting f-theta distortion or f-sin(theta) distortion. According to some embodiments, the rotatable optical element is a dove prism, a reversion or "K" prism, a Delta or Pechan prism, or any other associated prism known in the art.

According to other embodiments, the rotatable optical element is a dispersive prism, a reflective prism, a beam-splitting prism or a deflective prism. According to some embodiments, the prism is a low-loss deflective prism. According to some embodiments, the dispersive prism is a triangular, a Pellin-Broca prism, an Abbe Prism or a compound prism.

According to other embodiments, the prism has a triangular or trapezoidal shape. According to other embodiments, the form of the prism is made from glass (i.e., BK7 glass or fused silica) and is designed for a laser such as a diode laser, fiber laser or a nNd:YAG laser beam.

According to other embodiments, the prism is a Glan-Taylor prism or a Glan-laser prism. According to other embodiments, the prism is an equilateral glass prism.

According to other embodiments, the prism is selected from a group consisting of anamorphic Prism Pairs, a high-powered laser-light right angle prism, a hollow retroreflector, a laser-line right angle prism, a N-BK7 Corner Cube Retroflector or a UV Fused Silica Corner Cube Retroflector.

According to some embodiments, a prism compressor or a pulse compressor is used in conjunction with the prism.

According to some embodiments, the laser element may further comprise an actuator for rotating the rotatable optical element. The actuator may be a hydraulic, mechanical, or an electrical/electronic actuator; and, may utilize pins, gears, magnets, or other type of elements, that can initiate and control the rotation of the rotatable optical element.

According to some embodiments, the actuator uses a wire to initiate and control the rotation of the rotatable optical element.

According to some embodiments, the laser element may comprise a controller for actuating the optical rotator in accordance with an input signal from an input device. The controller may be processor and/or microprocessor based for precisely regulating the position of the actuator. The controller may contain circuitry necessary to interpret and execute instructions from an input device. As a result of interpreting and executing the instructions, the controller may output corresponding instructions and/or signals to initiate and regulate the actuator position.

According to some embodiments, the actuating of the rotatable optical element may be automatic, where the portion of a wide viewing field, and/or a region of interest within the wide view field, may be automatically selected from standard viewing angles typically used, including, but not limited to, 0, 30, 45, 70, 90, 120, 180 degrees from the longitudinal axis of the catheter.

According to some embodiments, the rotatable optical element is configured to rotate and/or split the laser beam emitted by the laser element. Each possibility represents a separate embodiment of the present disclosure. According to some embodiments, the rotatable optical element is configured to rotate the laser beam emitted by the laser element. According to some embodiments, the rotatable optical element is configured to enable rotational movement of laser radiation emitted by the laser element around the longitudinal axis of the duodenum. According to some embodiments, the rotatable optical element is configured to rotate concomitantly with movement of the laser element along the duodenum, such that the emitted laser radiation generates a spiral-like ablation pattern. According to some embodiments, the emitted laser radiation generates a helical-like ablation pattern. According to some embodiments, the emitted laser radiation generates a circular or cylindrical-like ablation pattern.

According to some embodiments, an optical is provided that may fold and rotate emitted laser radiation or a laser beam.

According to some embodiments, the rotatable optical element is configured to enable splitting of laser radiation. According to some embodiments, the rotatable optical element is configured to enable splitting of laser radiation such that part of the laser radiation is directed at a target area and part of the laser radiation is directed at an imaging element, such as, but not limited to, a camera. According to some embodiments, the camera includes a controller, the controller being able to process data provided by part of the laser radiation. According to some embodiments, the imaging element is located in the distal region of the catheter.

According to some embodiments, the laser element is rotatable. According to some embodiments, the laser element itself is a rotatable optical element. According to some embodiments, the laser element is rotatable such that the laser radiation emitted by the laser element is configured to move in at least part of a rotational trajectory around the longitudinal axis of the duodenum. Without wishing to be bound by theory or mechanism, using a laser element comprising a rotatable optical element, such as a rotatable prism, enables to ablate a ring-like target area along the duodenal wall.

According to some embodiments, the laser element further comprises an actuator for rotating the laser element itself. The actuator may be a hydraulic, mechanical, or an electrical/electronic actuator; and, may utilize pins, gears, magnets, or other type of elements, that can initiate and control the rotation of the rotatable optical element.

According to some embodiments, the laser element is functionally connected to a controller. According to some embodiments, the controller is configured to actuate the laser element to emit laser radiation. According to some embodiments, the controller is configured to start and/or stop and/or direct the rotation of the rotatable optical element. Each possibility represents a separate embodiment of the present disclosure. According to some embodiments, the controller is configured to determine the target area to which the laser radiation is directed. According to some embodiments, the controller is able to select standard angles of rotation including, but not limited to, 0, 30, 45, 70, or 90 degrees from the longitudinal axis of the catheter.

According to some embodiments, the laser element comprises at least one aperture configured to enable directed emission of laser radiation. According to some embodiments, the laser element comprises at least one focusing element, configured to focus the laser radiation. According to some embodiments, the laser element comprises at least one focusing element, configured to focus the laser radiation on a target area. According to some embodiments, the focusing element is at least one lens. According to some embodiments, the lens may be a correction lens. According to some embodiments, the focusing element allows the laser radiation to be tapered or allows the laser radiation to be channeled through a narrow element. According to some embodiments, the lens corrects aberration. The aberration may be spherical aberration, axial chromatic aberration and any other types of known aberrations in the art.

According to some embodiments, the lens does not contribute to distortion, lateral chromatic aberration, astigmatism or field curvature.

According to some embodiments, the lens is capable of removing f-theta distortion. An f-theta optical lens uniformly separates the light rays incident to a wide angle lens by a distance proportional to f-theta, where f is the focal distance of the lens system and theta is the angle of incidence of the image rays relative to optical axis. The f-theta optical lens provides a uniform distribution of the image field relative to the optical axis such that equivalent solid angles in the object will be imaged onto equivalently sized regions of the imaging area.

According to some embodiments, the lens is capable of removing f-sin(theta) distortion. In an f-sin(theta) optical system the radial height of an image relative to the image location of the optical axis is proportional to the sine of the corresponding object angle from which it originated. An f-sin(theta) optical system provides a uniform f-number across the image plane, and therefore uniform illumination and potentially uniform MTF. An f-sin(theta) optical system allows for equal solid angles in object space to be imaged onto equal areas of the image plane.

If the optical system does not correct the variation in information density attributable to the wide angle lens system, then it may be necessary to provide circuitry that can correct any distortion or uneven information density that can be present in the image signal or the region of interest signal. However, by utilizing an f-theta optical system, the need to incorporate corrective circuitry and the complexities associated with such manipulation can be avoided.

According to some embodiments, the system may further comprise an illumination system. The illumination system may provide light into the lumen of a subject's duodenum. The illumination system may be made of one or more light emitting diodes (LEDs). The illumination system may further include other known methods for providing light into the lumen of a subject's duodenum.

According to some embodiments, the system may further comprise a display, the display able to display a view the lumen of a subject's duodenum.

Figure 6:
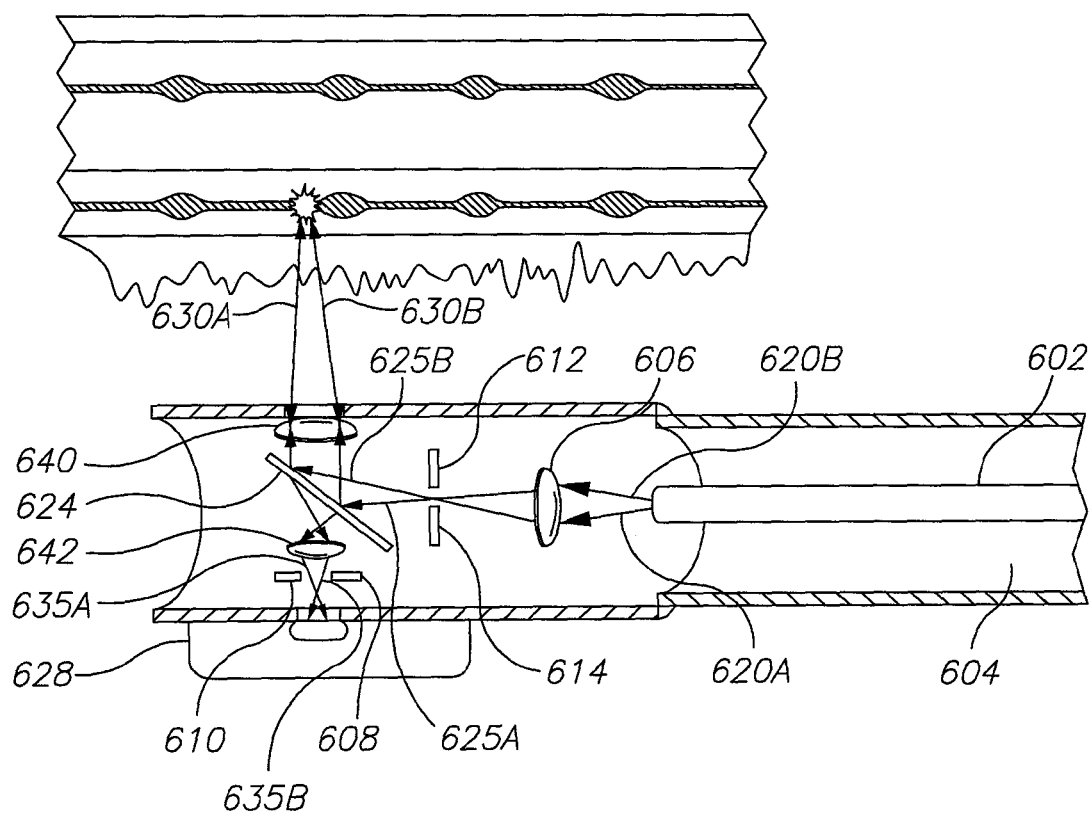
FIG. 6 schematically illustrates an endoluminal duodenal catheter, which emits a laser beam, according to some embodiments.

Reference is now made to FIG. 6, illustrating, according to some embodiments, blocking or modulation of neural activity in the duodenal wall by use of laser radiation which is not configured to be strongly absorbed in the lumen wall. FIG. 6 depicts a longitudinal cross section through part of duodenum and catheter (604) which is introduced into the lumen of duodenum, according to some embodiments.

Catheter (604) comprises laser element having optic fiber (602) which is partially comprised in the laser element. Optic fiber (602) emits laser radiation (620A, 620B) which passes through a focusing element, such as but not limited to, at least one lens element (606) and is rotated by rotatable beam splitter (624) such that focused laser radiation (630A, 630B) is directed at a target area. According to some embodiments, a second lens element (640) also is provided to focus laser radiation at target area. According to some embodiments, the at least one focusing element is able to focus the laser radiation at angles, including, but not limited to, 0, 30, 45, 70, 90 or 120 degrees from the longitudinal axis of the catheter (604).

The at least one lens element (606) may include aspherical, aspheric cylindrical or correction lens or other types of lenses that are able to focus the laser and reduce aberration. To assist in focusing the laser at the pre-determined target, physical means that are provided to select an appropriate layer of focus are also shown.

As shown in FIG. 6, physical means include blocking elements (612, 614, 608 and 610) that help control and/or focus the laser by producing a controlled aperture. According to some embodiments, elements (612, 614) are used to ensure that the laser beam generates a the required spot at the pre-determined layer. According to some embodiments, elements (608, 610) are used to form an aperture to assure the image acquired is from the layer of interesting and to block scattered light from other layers, in analogy to the principles of confocal microscopy.

Furthermore, an imaging element (628) is shown, such that laser radiation (635A, 635B) is back reflected, scattered or emanating from an adjunct source and is collected by imaging element (628). Imaging element (628) may be any suitable element for capturing information through lens (642) such as, but not limited to a single detector, detector arrays, camera or detector, such as a CCD and CMOS chips. According to some embodiments, imaging element (628) is configured to capture information about the structure of the duodenum and/or surrounding tissue and/or monitor the process on-line by monitoring changes in the optical characteristics of tissue following interaction of tissue with the laser beam. Each possibility represents a separate embodiment of the present disclosure.

Figure 7:
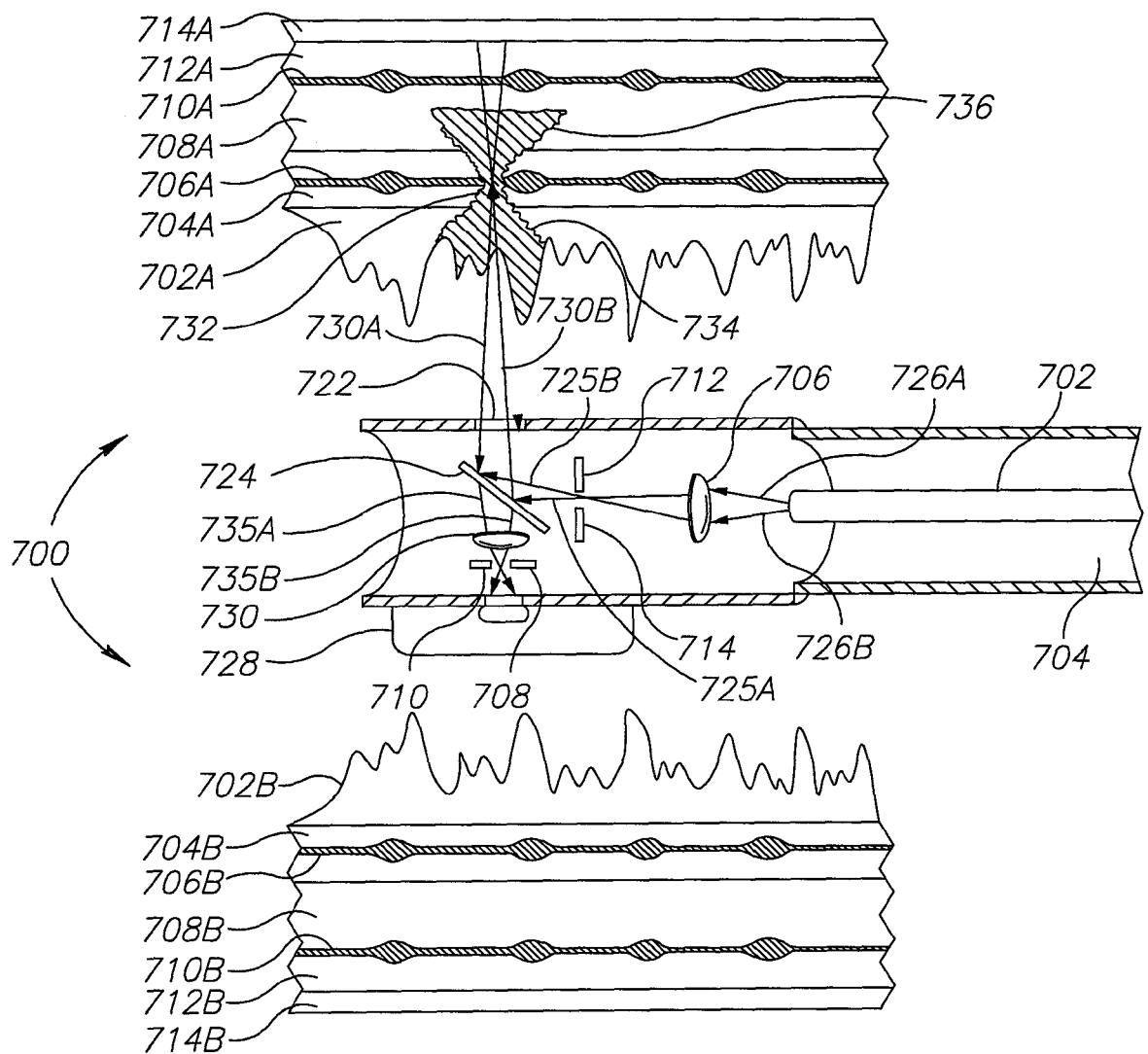
FIG. 7 schematically illustrates an alternative embodiment that uses a laser that is absorbed by the tissue, but the beam is focused to the targeted layer.

FIG. 6 further provides that rotatable beam splitter (624) is able to fold the laser, thereby creating automatically or semi-automatically a circular modulation of/impact on the tissue around the duodenal axis and optionally containing an accessory for imaging of the focus to enable selection of the appropriate layer. In certain embodiments rotatable beam splitter (624) is able to reflect the beam to the tissue through a lens and control the angle of deflection while having partial transmittance to enable light that is back reflected, scattered or fluorescence emitted from the tissue to pass through the beam splitter. In case of fluorescence, beam splitter (624) may be made from a dicrohic mirror known in the art so that the laser beam is effectively deflected while in other wavelengths the light energy passes through filtered by the aperture formed by element (610, 608) and transferred using lens (642) to imaging element (628) FIG. 7 illustrates an alternative embodiment to FIG. 6 that uses a laser that is partially absorbed by the tissue, but the beam is focused to the targeted layer to cause its main impact there while minimizing its collateral impact on layers above and below the targeted layer. In the figure the focus is in the sub mucosal layer Reference is now made to FIG. 7, illustrating, according to some embodiments, blocking of neural activity in the duodenal wall by use of laser radiation which can be partially absorbed in tissue outside the target area. FIG. 7 depicts a longitudinal cross section through part of duodenum (700) and catheter (704) which is introduced into the lumen of duodenum (700), according to some embodiments. The duodenum wall of duodenum (700) comprises the mucosal layer (702A, 702B), the submucosal layer (704A, 704B) which comprises submucosal plexus (706A and 706B, respectively), circular muscle (708A, 708B), myentric plexus (710A, 710B), longitudinal muscle (712A, 712B) and mesenteric layer (714A, 714B).

Catheter (704) comprises laser element and optic fiber (702) which is partially comprised in laser element. Optic fiber (702) emits laser radiation (726A, 726B) which is split by beam splitter (724) and passes through focusing lens (706) such that focused laser radiation (730A, 730B) is directed at target area (732) in the duodenal wall, which comprises part of the sensory neurons of submucosal plexus (4706A). According to some embodiments, since the laser element emits a large spot, focusing lens (706) is positioned before the beam rotator. According to certain embodiments, typical lenses with focal length of a few cm may be used in such a configuration to create a spot in the order of 100 micron to less than 1 mm in diameter, wherein according to the laser used single vs. multimode and spot required the lens is selected.

Beam splitter (724) with imaging lens (730) are used to collect back reflected, scattered, or fluorescence light from the tissue and direct it at imaging element (728). Laser radiation, such as radiation (735A, 735B) is directed at imaging element (728) through lens (730). Imaging element (728) may be a camera or any imaging element known in the art.

According to some embodiments the catheter (704) further comprises means of delivering a cooling or thermal shielding material to tissues, components or layers thereof surrounding the target area. Such means of delivery may include but are not limited to, a tube configured to deliver coolant material to tissues, components or layers thereof surrounding the target area. Non limiting examples of such coolant material include biocompatible coolant such as chilled physiological solutions and biocompatible gels. Non-limiting examples of such physiological solutions may include water or physiological saline; and non-limiting biocompatible and/or biodegradable gels may include hyaluronic acid, glycosaminoglycan-based gels, polysaccharide hydrogels, and additional natural & synthetic hydrogels known in the art. According to some embodiments said tissue, components and layers thereof surrounding the target area is the mucosal layer (702A, 702B) including the villous (villi) structures and additional structural-functional components contained therein.

According to some embodiments, a catheter is placed in the center of the lumen, that includes an optical head that can fold and rotate the beam, with stand offs that can hold the catheter in place such as by use of a balloon with appropriate pressure to determine the relative position allowing repositioning by a physician if required by deflating and re-inflating or slipping over the lumen. The head may include means for automatic linear movement across the duodenum. The balloon can be constructed from polymers that have high transparency for the laser beam and can withstand a relative high power. An example of a material that may be use are polyamides [http://www2.basf.us//PLASTICSWEB/displayanyfile?id=0901a5e180004886].

Figure 8:
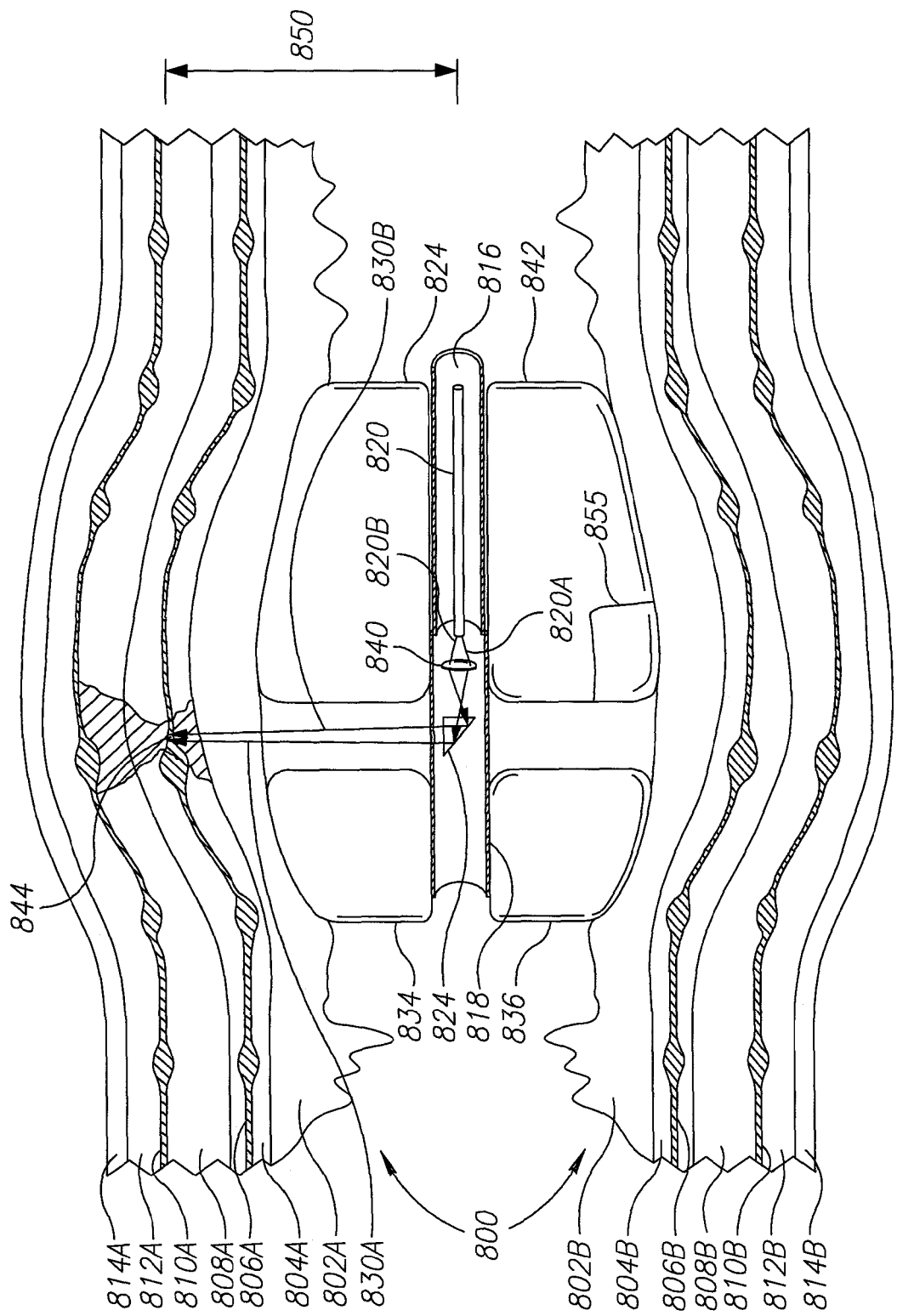
FIG. 8 schematically illustrates an embodiment of the endoluminal duodenal catheter of FIG. 6 showing the lens and its ability to split the laser beam.

Reference is now made to FIG. 8 illustrating, according to some embodiments, a catheter comprising pressure inducing elements in the form of balloons.

FIG. 8 depicts the longitudinal cross section depicted in after deflated pressure-inducing elements have been inflated to pressure-inducing elements (828, 834, 836, and 842) and induced pressure on the duodenal wall of duodenum (800), according to some embodiments. Accordingly, FIG. 8 depicts a longitudinal cross section through part of duodenum (800) and catheter (816) which is introduced into the lumen of duodenum (800). The duodenal wall of duodenum (800) comprises the mucosal layer (802A, 802B), the submucosal layer (804A, 804B) which comprises submucosal plexus (806A and 806B, respectively), circular muscle (808A, 808B), myentric plexus (810A, 810B), longitudinal muscle (812A8, 812B) and mesenteric layer (814A, 814B).

Catheter (816) comprises laser element and optic fiber (820) which is partially comprised in laser element. Optic fiber (820) is configured to emit laser radiation directed at rotatable prism (824) such that focused laser radiation is directed at a target area in the duodenal wall. Catheter (816) and laser element comprise pressure-inducing elements (828, 834, 836, and 842) in the form of balloons. According to some embodiments, Laser element (818) is configured to be actuated only once pressure-inducing elements (828, 834, 836, and 842) have been inflated and induced pressure on the duodenal wall. According to certain embodiments, a controller is used to control actuation of pressure-inducing elements (828, 834, 836, and 842).

Following inflation of deflated pressure-inducing elements to pressure-inducing elements (828, 834, 836, and 842), pressure was induced on duodenal wall of duodenum (800) such that the lumen is stretched to increase its effective diameter by utilizing its certain compliance capability such that pre-set optical path distance (850) between the target area and the optical axis of catheter (816) is achieved, According to certain embodiments the thickness of duodenal wall layers is reduced using pressure-inducing elements (828, 834, 836, and 842). Concomitantly or following inflation of pressure-inducing elements (828, 834, 836, and 842), optic fiber (820), comprised in laser element (818) emits laser radiation (820A, 820B) which is rotated by rotatable prism (824) such that laser radiation (830A, 830B) is directed at target area (844) comprising part of submucosal plexus (806A). According to some embodiments, due to the pressure exerted on the wall of duodenum (800) by inflated pressure-inducing elements (828, 834, 836, and 842) at least layers (802A) and (804A) are thinner and thus the optical path of laser (830A, 830B) is shortened. In certain embodiments the laser (830A, 830B) is focused at the required layer (such as submucosa 804A) by setting the predetermined optical distance (850) which guarantees the laser focal point is at the required layer regardless of inter and intra patient variability in lumen diameter and villi shape. According to other embodiments, the focusing lens (840) can be on variable translator to enable focusing on the required target based on imaging information. According to some embodiments, catheter (816) may be repositioned by deflating inflated pressure-inducing elements, moving catheter (816) and re-inflating the pressure-inducing elements at the desired position.

According to some embodiments pressure-inducing elements (828, 834, 836, and 842) are at least partially filled with liquid and include one or more acoustic transducers (855) to collect acoustic waves for the purpose of acousticoptic microscopy.

According to some embodiments the pressure-inducing elements (828, 834, 836, and 842) are filled with liquid used for cooling or thermal shielding of the tissues, components or layers thereof surrounding the target area. Non limiting examples of such coolant material include biocompatible coolants such as chilled physiological solutions and biocompatible gels which enables passage of laser radiation. According to some embodiments said tissue, components and layers thereof surrounding or adjacent to the target area is the mucosal layer (802A, 802B) including the villous (villi) structures and additional structural-functional components contained therein.

According to some embodiments, optic fiber (820) emits laser radiation (820A, 820B) which passes through a focusing element, such as but not limited to, at least one lens element (840) and is rotated by rotatable prism (824) such that focused laser radiation (830A, 830B) is directed at a target area. The at least one lens element (840) may include spherical or cylindrical lenses to produce round spots or lines and can include aspheric or cylindrical aspheric correction lens or other types of lenses that are able to focus the laser and reduce aberration. To assist in focusing the laser, physical means are provided to select an appropriate layer of focus is also shown.

In all of FIGS. 6-8, the rotatable optical elements are capable of rotating the beam and in some cases also enable light to be collected for imaging purposes. The same or other elements can be used to deflect the beam in angles different than 90 degrees or to scan a spot and generate a line parallel to the lumen axis. According to some embodiments, focusing elements such as lenses are used, which can further facilitate laser beam manipulation to direct the laser beam(s) on the target area and on imaging elements.

IX. IMAGING SYSTEMS

According to some embodiments, the imaging device is configured to capture structural information related to the duodenal wall or an area in contact with at least part of a duodenal wall, to determine that light is focused at the required layer (i.e., submucosal, muscularis, peripheral at the interface with ganglion or vagal nerves or in VAN interface) and/or to monitor interaction with tissue on-line for process control. Each possibility represents a separate embodiment of the present disclosure. According to some embodiments, the imaging device is configured to capture structural information related to the target area. According to some embodiments, the imaging device is configured to enable location of the target area based on structural information related to the duodenal wall or an area in contact with at least part of a duodenal wall. Each possibility represents a separate embodiment of the present disclosure. According to some embodiments, the imaging device is configured to enable visualization of the target area based on structural information related to the duodenal wall or an area in contact with at least part of a duodenal wall. Each possibility represents a separate embodiment of the present disclosure. According to some embodiments, the imaging device includes a camera or video device able to receive signals, such that the structural information related to the duodenal wall or an area in contact with at least part of a duodenal wall is able to be collected. According to some embodiments the imaging device provides information about the temperature at the target. According to some embodiments, the imaging device allows a user to focus the laser, such that that user has visual guidance within the duodenum of a subject, when using the catheter. According to some embodiments, visual guidance can be done automatically based on pre-determined algorithms.

According to some embodiments, the imaging device is configured to capture structural information related to thickness of at least one layer in the duodenal wall. According to some embodiments, the imaging device is configured to enable localization of the target area and/or a layer in the duodenal wall comprising the target area. Each possibility represents a separate embodiment of the present disclosure. According to some embodiments, the structural information relates to at least one of: thickness of duodenal wall layers, location of neurons, location of sensory neurons, location of blood vessels, blood flow through blood vessels, temperature, changes in optical characteristics of the target and lumen wall and a combination thereof. Each possibility represents a separate embodiment of the present disclosure.

According to some embodiments, the imaging device is an endoscope. According to some embodiments, the imaging device is an endoscope configured to be introduced into the lumen of the duodenum. According to some embodiments, the imaging device is an ultrasound endoscope configured to be introduced into the lumen of the duodenum and provide information about wall structure and thickness. According to some embodiments, the catheter comprises the imaging device. According to some embodiments, the imaging device is a camera video device, single chip or array detectors.

According to some embodiments the endoscopes further comprises means of delivering a cooling or thermal shielding material to tissues, components or layers thereof surrounding the target area. Such means of delivery may include but are not limited to, tubes threaded through the endoscope work channels configured to deliver coolant material to tissues, components or layers thereof surrounding the target area. Non limiting examples of such coolant material include biocompatible coolant such as chilled physiological solutions and biocompatible gels. Non-limiting examples of such physiological solutions may include water or physiological saline; and non-limiting biocompatible and/or biodegradable gels such as hyaluronic acid, glycosaminoglycan-based gels, polysaccharide hydrogels, and additional natural & synthetic hydrogels known in the art. According to some embodiments said tissue, components and layers thereof surrounding the target area is the mucosal layer including the villous (villi) structures and additional structural-functional components contained therein.

According to some embodiments, the imaging captured by the imaging device is optical imaging. According to some embodiments, imaging is thermal imaging. According to some embodiments, imaging is ultrasonic imaging. According to some embodiments, imaging is Infra-Red and/or Near Infra-Red imaging. Each possibility represents a separate embodiment of the present disclosure. According to some embodiments, imaging is Optical Coherence Tomography (OCT) based imaging. According to some embodiments, imaging is any combination of the above imaging modalities. According to a non-limiting example, the imaging device is configured to use ultrasound and/or NIR imaging and/or OCT imaging in order to capture structural information relating to target areas comprising different layers of duodenum wall and sensory neurons that interface with the duodenal wall, such as, but not limited to, ganglions and/or vagal nerves. Each possibility represents a separate embodiment of the present disclosure. According to some embodiments, the imaging device is configured to locate the target area. According to some embodiments, the imaging device is configured to locate the target area based on blood vessels residing near the target area using modalities such as, but not limited to, ultrasonic energy, NIR imaging and a combination thereof. Each possibility represents a separate embodiment of the present disclosure. According to some embodiments, the imaging device is configured to locate the target area based on detecting blood vessels and/or blood flow at vessels that are adjacent to sensory nerves of interest in the target area. Orientation of the imaging device and/or catheter may be induced by manual rotation across the lumen and/or by semiautomatic or automatic means. Each possibility represents a separate embodiment of the present disclosure.

According to some embodiments, the target area may be identified anatomically based on known landmarks, using imaging device, such as, but not limited to, an endoscope configured for optic imaging. In certain embodiments, the target area may be identified using an imaging device configured for Near-Infra-Red imaging and/or visible light imaging and/or OCT imaging and/or ultrasound imaging and/or photo-acoustic microscopy. Each possibility represents a separate embodiment of the present disclosure.

According to some embodiments, the target area may be identified through magnetic resonance imaging (MM), microwaves, external ultra-sound, X-rays or a combination thereof. Each possibility represents a separate embodiment of the present disclosure.

According to some embodiments, the imaging device is configured to capture structural information related to the duodenal wall or an area in contact with at least part of a duodenal wall and thus enable determining whether the catheter is in the desired location within the duodenum and/or if damage has been caused at the target area. Each possibility represents a separate embodiment of the present disclosure.

According to some embodiments, the disclosed method further comprises various types of imaging. According to some embodiments, the disclosed method further comprises imaging to obtain structural information of the duodenum. According to some embodiments, imaging is used to select the target area. According to some embodiments, imaging is used to monitor the changes and/or determine the impact induced by the laser radiation at the target area. According to some embodiments, imaging is performed prior to direction of the focused laser radiation to the target area in order to determine the location of the target area. According to some embodiments, imaging is performed using an imaging device, such as, but not limited to, an endoscope. According to some embodiments, the imaging device is configured to use more than one imaging modality, such as, but not limited to, ultrasonic imaging, NIR imaging, confocal imaging and OCT imaging.

According to some embodiments, the disclosed system comprises a controller. According to some embodiments, the controller is a processor. According to some embodiments, the controller is functionally connected with at least one of the laser element and the imaging device. Each possibility represents a separate embodiment of the present disclosure. According to some embodiments, the controller is configured to actuate the laser element to emit laser radiation. According to some embodiments, the controller is configured to receive input from the imaging device. According to some embodiments, the controller receives input from an input device. According to some embodiments, input devices are a mouse, keypad and/or a touchpad. According to some embodiments, the input devices are controlled by voice commands. According to some embodiments, the controller is configured to determine the identity and/or location of the one or more target area based on input relating to structural information received from the imaging device. According to some embodiments, the controller is configured to induce focusing of the laser radiation to the target area.

According to some embodiment the disclosed system comprises a controller that is configured to control the flow and/or temperature of a coolant material used for cooling or thermal shielding of tissues, components or layers thereof surrounding the target area. Non limiting examples include infusion pumps of chilled coolants to induce local hypothermia as known in the art. Non limiting examples of coolant material include biocompatible coolant such as chilled physiological solutions and biocompatible gels. Non-limiting examples of such physiological solutions may include water or physiological saline; or biocompatible and/or biodegradable gels such as hyaluronic acid, glycosaminoglycan-based gels, polysaccharide hydrogels, and additional natural & synthetic hydrogels known in the art. According to some embodiment cold gases are used that can be delivered through the catheter or generated on the spot such as, but not limited to, liquid nitrogen that evaporated close enough to the target that requires cooling. According to some embodiments said tissue, components and layers thereof surrounding the target area is the mucosal layer including the villous (villi) structures and additional structural-functional components contained therein.

According to some embodiments, the controller is functionally connected to the rotatable optic element. According to some embodiments, the controller is configured to actuate rotation and/or determine the direction and/or speed of rotation of the rotatable optic element. Each possibility represents a separate embodiment of the present disclosure. According to some embodiments, the controller is configured to induce rotation of the rotatable optic element such that the laser radiation moves in at least part of a circular trajectory around the longitudinal axis of the duodenum. According to some embodiments, the controller is configured to induce rotation of the rotatable optic element such that the laser radiation may be directed towards a plurality of target areas. According to some embodiments the controller can be configured to generate a circle of intervention for blocking the signals in one place in submucoasal and/or muscularis plexuses and then move the optical head a few millimeters to generate another circle of impact and so forth to block signals at different positions across the duodenal wall. In certain embodiments the distance of these circles is smaller at the proximal part of the duodenum and larger at more distal parts. In some examples the distance of the circles is in the range of 2-200 mm in the beginning and 10-50 mm in more distal parts.

According to some embodiments, an actuator is used to actuate and/or determine the direction and/or speed of rotation of the rotatable optic element. In certain embodiments, the actuator is controlled by voice commands.

According to some embodiments, the disclosed system comprises at least one pressure-inducing element. According to some embodiments, the controller is configured to actuate the at least one pressure-inducing element to induce pressure on the duodenal wall. According to some embodiments, the controller is configured to actuate the at least one pressure-inducing element to induce pressure on the duodenal wall such that the laser element is fixed in the right place in the lumen of the duodenum.

According to some embodiments, the controller is configured to actuate the at least one pressure-inducing element to induce pressure on the duodenal wall such that at least one layer in the duodenum wall changes thickness level. According to some embodiments, the controller is configured to be able to determine the level of pressure exerted by the at least one pressure-inducing element. According to some embodiments, the controller is configured to modulate the level of pressure exerted by the at least one pressure-inducing element depending on the required optical path required for the laser radiation to cause damage in the target area.

According to some embodiment the disclosed system comprises a controller that is configured to actuate an at least one pressure-inducing element, means or devices for stretching or confining the section of the duodenal lumen to be treated; to control the flow and/or temperature of a coolant material contained within the at least one pressure-inducing element used or contained in a luminal space confined between the means or devices for stretching or confining the section of the duodenal lumen to be treated; for cooling or thermal shielding of tissues, components or layers thereof surrounding the target area. Non limiting examples include infusion pumps of chilled coolant-containing balloons as known in the art. Non limiting examples of coolant material include biocompatible coolant such as chilled physiological solutions and biocompatible gels. Non-limiting examples of such physiological solutions may include water or physiological saline; or biocompatible and/or biodegradable gels such as hyaluronic acid, glycosaminoglycan-based gels, polysaccharide hydrogels, and additional natural & synthetic hydrogels known in the art. According to some embodiments said tissue, components and layers thereof surrounding the target area is the mucosal layer including the villous (villi) structures and additional structural-functional components contained therein.

According to certain embodiments, damage to neurons within a target area in the duodenal wall or in contact with the duodenal wall may be induced by at least one energy form selected from the group consisting of: laser radiation, electrical energy, microwave energy, ultrasound and a combination thereof. Each possibility represents a separate embodiment of the present disclosure. According to certain embodiments, electrical energy may be used in place of laser energy.

Figure 9:
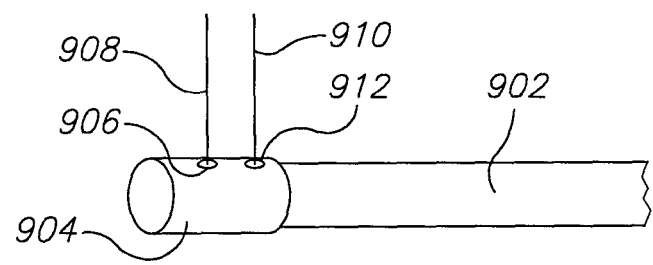
FIG. 9 schematically illustrates an endoscope having a catheter assembled on the endoscope.

FIG. 9 schematically illustrates an endoscope having a catheter assembled on the endoscope. FIG. 9 illustrates another embodiment wherein electrical energy is used instead of laser energy for the interaction with the tissue, by means of contact of the apparatus with the tissue. This can be achieved by the use of a catheter that assembles on an endoscope (as schematically illustrated) or in a stand-alone catheter.

According to FIG. 9, endoscope (902) includes a catheter (904) assembled on the endoscope. In certain embodiments the catheter or part of the catheter described in previous figures is assembled on an endoscope. In certain embodiments illustrated in FIG. 9 electrical energy is used to induce damage to neural elements by means known in the field of electrophysiology. In FIG. 9, electrical energy is shown passing through apertures (906, 912) in catheter (904), using wires (908) and (910) used to transmit high voltage to induce damage.

According to some embodiments, electrical energy is produced via a wire or via an electrical circuit According to some embodiments, protocols of Irreversible Electroporation (IRE) such as 1,500 V/cm; with pulse length, 70 µs or higher to induce permanent damage may be used. According to some embodiments, electrical energy is provided via a capacitor. According to some embodiments, electrical energy is provided via a device that transmits electrical energy. According to some embodiments, electrical energy is provided via terminal or pole that transmits electrical energy.

According to some embodiments, microwaves may be used in place of laser energy.

According to some embodiments, damage to neurons within a target area in the duodenal wall or in contact with the duodenal wall may be induced by use of ultrasound energy. According to some embodiments, the ultrasound energy is focused energy. Non-limiting example of applicable technologies known in the art include, but are not limited to, microfocused ultrasound, laser induced focused ultrasound (LGFU) or Enhancement of focused ultrasound with micro-bubbles. According to some embodiments, the ultrasound energy is non-focused energy. According to some embodiments, the ultrasound energy is focused such that it is configured to target the duodenal wall or layers within the wall or layers at the periphery of the wall or non-focused such that it is configured to target the interface of sensory nerved of the duodenum with the ganglia and/or vagal nerves. Each possibility represents a separate embodiment of the present disclosure.

According to some embodiments, there is provided a catheter with an ultrasound emitting element configured to beam ultrasound waves for performing modulation, attenuation, inhibition, denervation or excitation of nerve cells, nerve fibers, synapse interfaces or sensory elements in an organ. Each possibility represents a separate embodiment of the present disclosure. The catheter is configured to be introduced to a lumen of the organ and to emit an ultrasound beam within the lumen. According to some embodiments, the ultrasound emitting element is an ultrasound transducer. According to some embodiments, the ultrasound emitting element is a piezoelectric ultrasound transducer.

According to some embodiments, the ultrasound emitting element is configured to emit ultrasound beams with defined spatial properties. According to some embodiments, the spatial properties of the ultrasound beam are configurable.

Figure 10A:
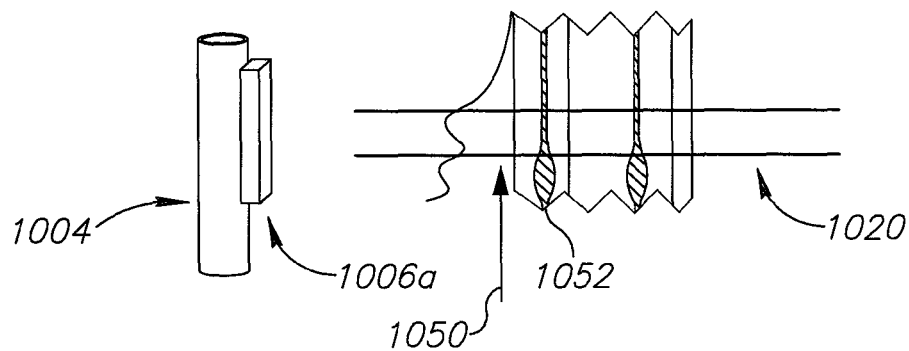
FIG. 10A schematically illustrates a catheter with an ultrasound emitting element which emits a collimated or nearly collimated ultrasound beam, according to some embodiments.

FIG. 10A schematically illustrates a catheter (1004) with an ultrasound transducer (1006a) associated therewith, according to some embodiments. Ultrasound transducer (1006a) is configured to emit a collimated ultrasound beam (1020) to a wall (1050) of a lumen to modulate a target neural structure (1052). Advantageously, collimated ultrasound beam (1020) has a relatively constant flux of energy and may be less sensitive to inter and intra variability of lumen dimensions and wall (1050) thickness as a whole and to specific layers that include neuronal structures (1052) such as but not limited to: nerve cells, nerves fibers, synapse interfaces, ganglia, and neural plexuses that may constitute a part of the enteric nervous system or the peripheral nervous system and composed of either extrinsic or intrinsic nerves, vagal or splanchnic nerves, parasympathetic nerves, sympathetic nerves, vein-artery-nerve (VAN) bundles, and combinations thereof.

Figure 10B:
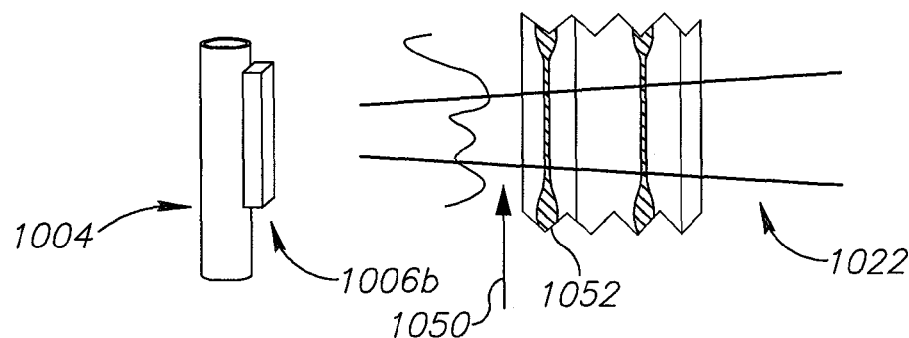
FIG. 10B schematically illustrates a catheter with an ultrasound emitting element which emits a diverting ultrasound beam, according to some embodiments.

FIG. 10B schematically illustrates a catheter (1004) with an ultrasound transducer (1006b) associated therewith, according to some embodiments. Ultrasound transducer (1006b) is configured to emit a diverting ultrasound beam (1022) to a wall (1050) of a lumen to modulate a target neural structure (1052). Advantageously, diverting ultrasound beam (1022) provides a low flux of energy as the beam progresses spatially and passes through wall (1050) or other targeted organs and is emitted from the lumen.

Figure 10C:
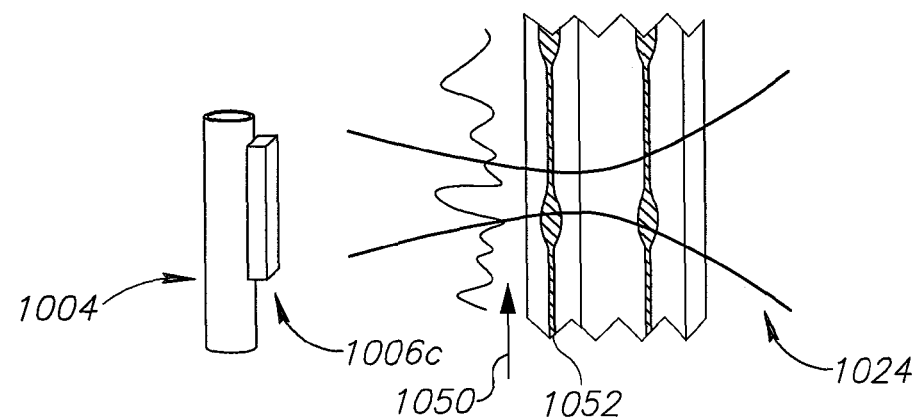
FIG. 10C schematically illustrates a catheter with an ultrasound emitting element which emits a partially focused ultrasound beam, according to some embodiments.

FIG. 10C schematically illustrates a catheter (1004) with an ultrasound transducer (1006c) associated therewith, according to some embodiments. Ultrasound transducer (1006c) is configured to emit a partially focused ultrasound beam (1024) to a wall (1050) of a lumen to modulate a target neural structure (1052). Advantageously, partially focused ultrasound beam (1024) has a relatively high flux of energy at or near neural structure (1052) to allow for a modulation thereof, and the flux of energy is reduced as the beam progresses and the impact on other non-targeted organs is reduced.

Figure 10D:
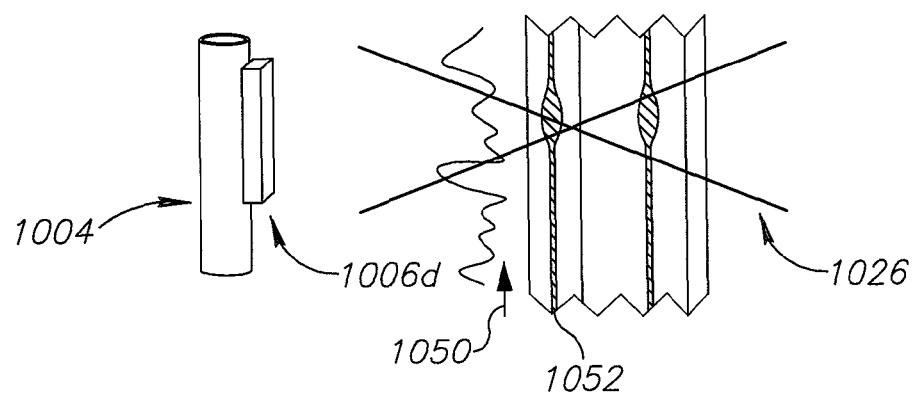
FIG. 10D schematically illustrates a catheter with an ultrasound emitting element which emits a focused ultrasound beam, according to some embodiments.

FIG. 10D schematically illustrates a catheter (1004) with an ultrasound transducer (1006d) associated therewith, according to some embodiments. Ultrasound transducer (1006d) is configured to emit a focused ultrasound beam (1026) to a wall (1050) of a lumen to modulate a target neural structure (1052). Advantageously, focused ultrasound beam (1026) has a relatively high selectivity of areas with a high flux of energy at or near neural structure (1052) to allow for a modulation thereof, and the flux of energy is reduced as the beam progresses and the impact on other non-targeted organs is reduced. Emitting focused ultrasound beam (1026) may require a close and complicated control of ultrasound transducer (1006d).

According to some embodiments, the ultrasound transducer is configured to emit circular ultrasound beams. Circular ultrasound beams are beams that propagate radially from the ultrasound transducer in a full circular range of 360 degrees around the ultrasound transducer.

According to some embodiments, the catheter comprises an inflatable structure. According to some embodiments, the inflatable structure is pressure induced, such as a latex balloon or a silicone balloon. The inflatable structure is configured to be inflated within the lumen and, according to some embodiments, to press against the walls of the lumen. According to some embodiments, the inflatable structure is configured to push the walls of the lumen to obtain a desired spacing between the ultrasound emitting element and the walls. According to some embodiments, the inflatable structure is configured to reduce structure variations of the lumen wall surface.

Figure 11:
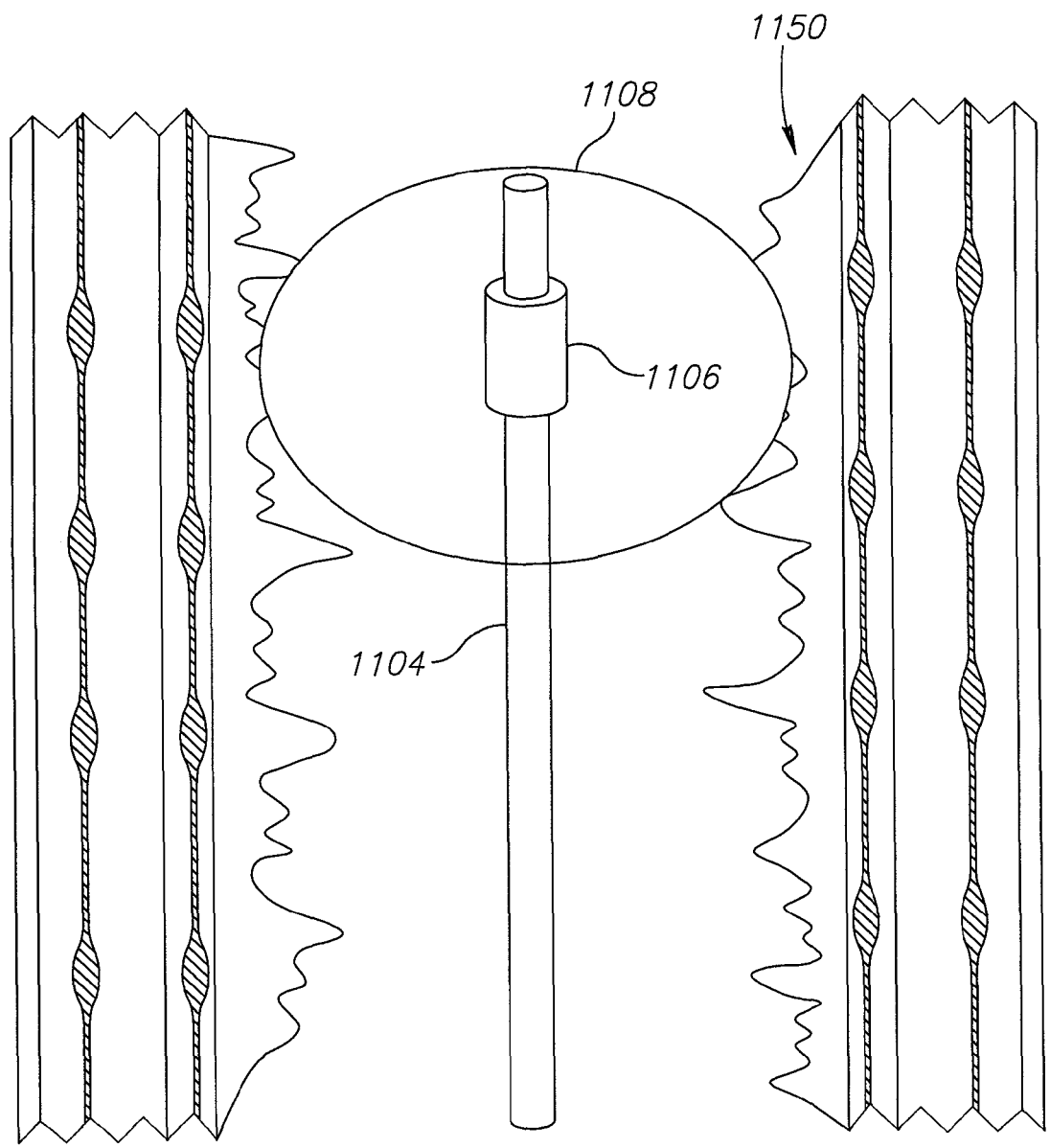
FIG. 11 schematically illustrates a catheter with an ultrasound emitting element and a surrounding balloon, according to some embodiments.

FIG. 11 schematically illustrates a catheter (1104) with a circular ultrasound emitting element (1106) and a balloon (1108) surrounding ultrasound emitting element (1106), according to some embodiments. Balloon (1108) is inflatable and configured to press against a lumen wall (1150). According to some embodiments, balloon (1108) is configured to enable passage of ultrasound energy. According to some embodiments, balloon (1108) is configured to be filled with fluids, such as water. According to some embodiments, the fluids in balloon (1108) act as a cooling agent to absorb heat from lumen wall (1150) or other bodily organs. According to some embodiments, balloon (1108) contains latex. According to some embodiments, balloon (1108) contains silicone materials. According to some embodiments, balloon (1108) is made from tear resistant material. According to some embodiments, balloon (1108) is made from materials that enable passing ultrasound beams therethrough. According to some embodiments, balloon (1108) is configured to place catheter (1104) and/or ultrasound emitting element (1106) in a centered location inside the lumen. Advantageously, positioning catheter (1104) and/or ultrasound emitting element (1106) in a centered location inside the lumen may result in a relatively even flux of energy on wall (1150).

According to some embodiments, balloon (1108) is at least partially inflated with liquid. According to some embodiments, the liquid includes water, saline or the like. According to some embodiments, the liquid is inserted into the balloon at a controlled temperature. According to some embodiments, warm liquid is inserted into balloon (1108) for raising the temperature of lumen wall (1150). According to some embodiments, low temperature liquid is inserted into balloon (1108) to lower the temperature of lumen wall (1150) or parts of catheter (1104), thereby mitigating/preventing damage to tissues that might be caused by heat.

Figure 12:
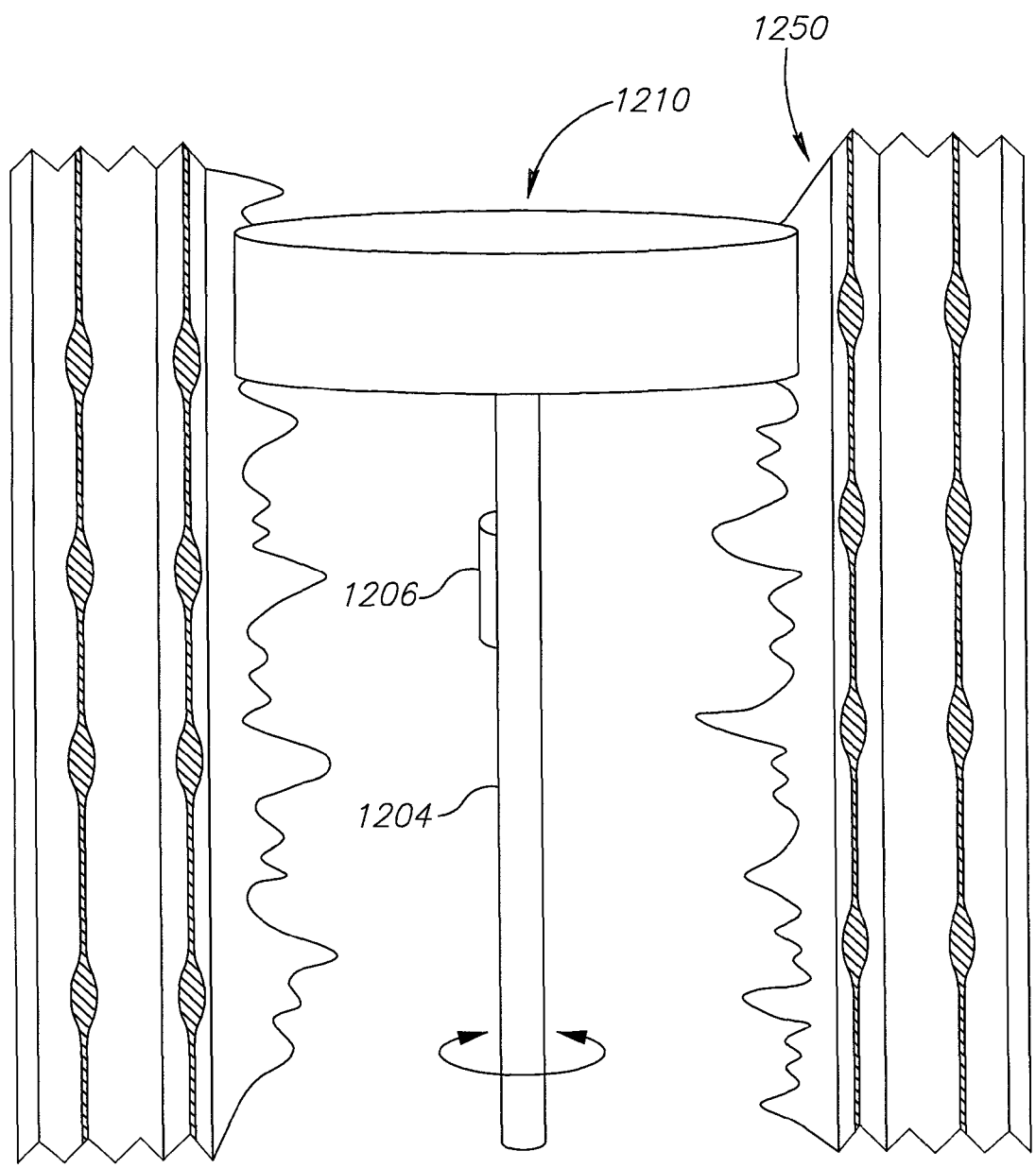
FIG. 12 schematically illustrates a rotatable catheter with an ultrasound emitting element and a distal balloon, according to some embodiments.

FIG. 12 schematically illustrates a catheter (1204) with an ultrasound emitting element (1206) and a distal balloon (1210), according to some embodiments. According to some embodiments, ultrasound emitting element (1206) is configured to emit ultrasound beams in a predetermined direction, angle and/or field. According to some embodiments, catheter (1204) and/or ultrasound emitting element (1206) are rotatable. Advantageously, rotating catheter (1204) and/or ultrasound emitting element (1206) may enable utilizing the directional beam for targeting various areas of a lumen wall (1250). According to some embodiments, beaming the ultrasound waves at various areas may enable modulation or denervation of a full circular range surrounding catheter (1204), or any portion of the circular range. According to some embodiments, distal balloon (1210) is mounted to a distal end of catheter (1204). According to some embodiments, distal balloon (1210) is mounted to a distal end of catheter (1204) such that when balloon (1210) is inflated, catheter (1204) is located at a relatively equal distance from lumen wall (1250) at various directions.

According to some embodiments, the catheter includes a cooling mechanism configured to lower the temperature of the organ or parts thereof. According to some embodiments, the cooling mechanism comprises an irrigation mechanism configured to deploy/provide irrigation fluids to the organ.

According to some embodiments, the catheter may include a warming mechanism configured to maintain or elevate the temperature of the organ or parts thereof. According to some embodiments, the warming mechanism comprises an irrigation mechanism configured to deploy/provide irrigation fluids to the organ. In some embodiments, the mucosa surface is warmed to a temperature in the area of 37 Celsius or above to increase impact of the ultrasound beam in the first layers of the duodenum wall rather than generating the main impact deeply below the surface which is less of interest in certain embodiments.

According to some embodiments the warming mechanism compromises a balloon filled with warm liquid. According to some embodiments, the balloon is made from tear resistant material. According to some embodiments, the balloon is made from materials that enable passing ultrasound beams therethrough. According to some embodiments, the balloon is configured to place catheter and/or ultrasound emitting element in a centered location inside the lumen. Advantageously, positioning catheter and/or ultrasound emitting element in a centered location inside the lumen may result in a relatively even flux of energy on wall. According to some embodiments the balloon is filled with warmed fluid at a temperature of 30-60 degrees Celsius. According to some embodiments the balloon is filled with warmed fluid at a controlled temperature.

According to some embodiments, the catheter may include an irrigation mechanism and the balloon is configured to confine the irrigation fluids in a desired space.

According to some embodiments, the catheter may include a second balloon mounted on the catheter at a proximal end. According to some embodiments, the distal balloon and the proximal balloon are configured to confine irrigation fluids in a space confined by the distal balloon, the wall of the lumen and the proximal balloon. According to some embodiments, the irrigation fluids include water. According to some embodiments, the irrigation fluids include saline. According to some embodiments, the irrigation fluids may facilitate coupling and/or cooling of the target area, organs of close proximity to the lumen, the lumen itself or parts thereof.

According to some embodiments, the ultrasound transducer is configured to beam ultrasound acoustic wave energy to the sides and can be used to create multiple overlapping areas of impact on non-overlapping modulation which can be accomplished by rotating the catheter.

Figure 13:
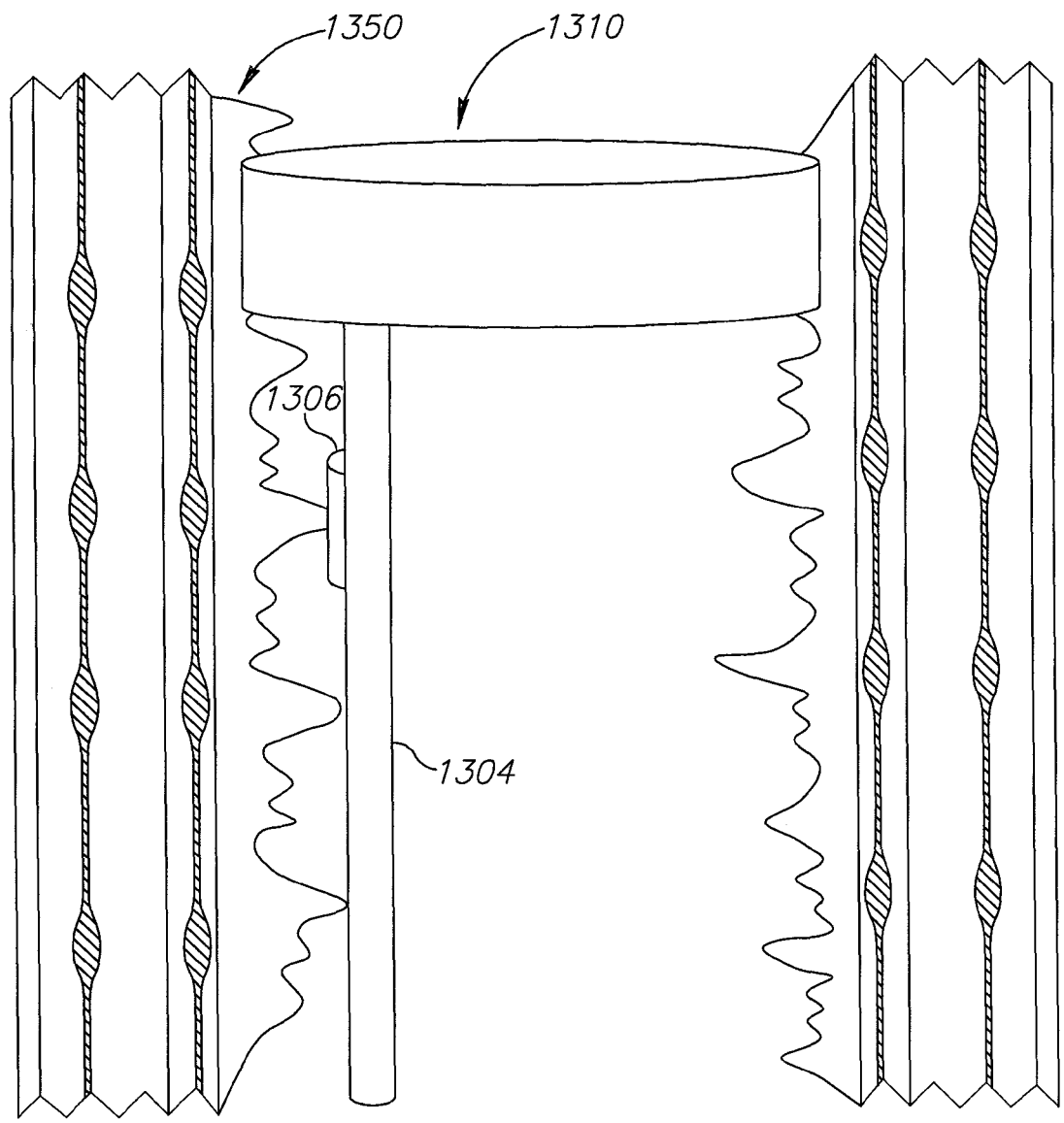
FIG. 13 schematically illustrates a catheter with an ultrasound emitting element and a distal balloon wherein the ultrasound emitting element is at close proximity to a wall of an organ, according to some embodiments.

FIG. 13 schematically illustrates a catheter (1304) with an ultrasound emitting element (1306) and a distal balloon (1310) wherein the ultrasound emitting element is at close proximity to a lumen wall (1350), according to some embodiments. According to some embodiments, balloon (1310) is configured to locate catheter (1304) and/or ultrasound emitting element (1306) at a close proximity to lumen wall (1350). According to some embodiments, balloon (1310) is configured to locate catheter (1304) and/or ultrasound emitting element (1306) at a direct contact with lumen wall (1350).

According to some embodiments, the catheter comprises an irrigation and/or cooling mechanism. Advantageously, having the catheter at a close proximity or direct contact with a lumen wall may provide highly effective cooling and/or irrigation of a desired area at the lumen wall.

According to some embodiments, the catheter includes ultrasound imaging capabilities. According to some embodiments, the ultrasound imaging capabilities are provided by an ultrasound imaging transducer. According to some embodiments, the ultrasound imaging capabilities are provided by a transducer additionally configured to provide modulating ultrasound beams.

According to some embodiments, the imaging capabilities may be utilized for obtaining imagery before, during and/or after the modulation of denervation process.

According to some embodiments, the ultrasounds transducers are configured to emit ultrasound beams at controlled variable intensities.

According to some embodiments, the catheter is assembled on an ultrasound endoscope.

According to some embodiments, the transducer is configured to emit an ultrasound beam with an exposure of approximately 30 seconds. According to some embodiments, the transducer is configured to emit an ultrasound beam with an exposure of no more than 60 seconds. According to some embodiments, the transducer is configured to emit an ultrasound beam with an exposure of no more than 100 seconds. According to some embodiments, the transducer is configured to emit an ultrasound beam with an exposure of at least 5 seconds.

According to some embodiments, the ultrasound transmission frequency is in the range of 100 KHz to 500 MHz, 200 KHz to 1 MHz, 1 MHz to 5 MHz, 3 MHz to 10 MH or 5 MHz to 40 MHz; each option may represent a different embodiment. According to some embodiments, the ultrasound frequency is tuned to be absorbed by the target area by means of frequency. According to some embodiments, ultrasound frequency is tuned to dispose maximal energy at target area, such that following target tissue, energy flux is too weak to damage the tissue.

A modulating ultrasound beam is an ultrasound beam having an energy and/or energy flux sufficiently high for modulation of neural structure or denervation. According to some embodiments, a modulating ultrasound beam has an intensity of approximately 5 to 150 Watt/$cm^2$ when modulation is at about 10 Mhz. According to some embodiments, a modulating ultrasound beam has an intensity of approximately 5 to 80 Watt/$cm^2$ when modulation is at about 20 Mhz. According to some embodiments, a modulating ultrasound beam has an intensity of less than about 300 Watt/$cm^2$.

According to some embodiments, a modulating ultrasound beam is an ultrasound wave having a frequency of approximately 20 MHz. According to some embodiments, a modulating ultrasound beam is an ultrasound wave having a frequency in the range of 200 KHz to 40 Mhz.

According to some embodiments, an imaging ultrasound beam is an ultrasound wave having a frequency of approximately 500 KHz-20 Mhz, for example, 500 KHz-700 Khz, 500 KHz-1 Mhz. According to some embodiments, an imaging ultrasound beam is an ultrasound wave having a frequency in the range of 5 MHz to 50 Mhz.

Figure 14A:
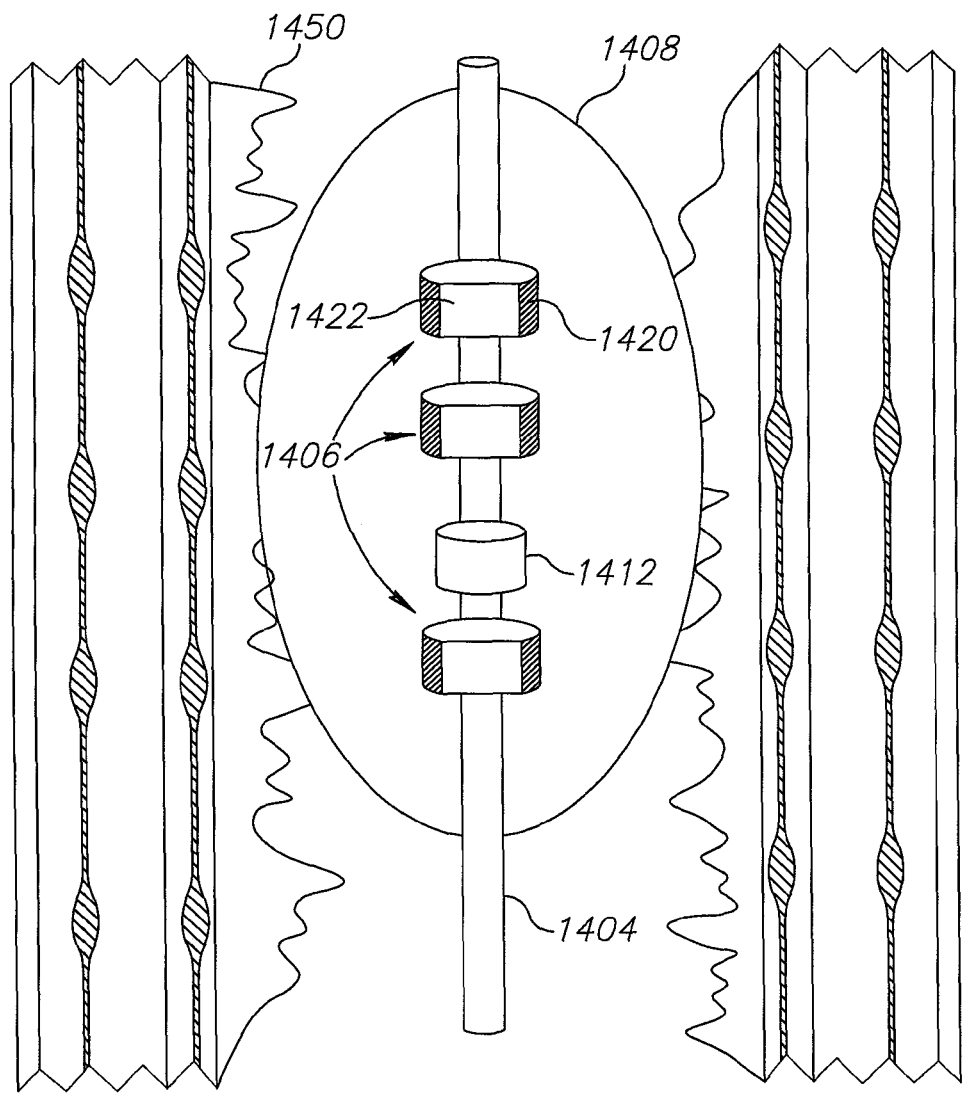
FIG. 14A schematically illustrates a catheter with an array of directional ultrasound emitting elements, an ultrasound imaging element and a surrounding balloon, according to some embodiments.

FIG. 14A schematically illustrates a catheter (1404) with an array of directional ultrasound emitting elements (1406), an ultrasound imaging element (1412) and a surrounding balloon (1408), according to some embodiments. Balloon (1408) surrounds catheter (1404), array of ultrasound emitting elements (1406) and ultrasound imaging element (1412). Balloon (1408) is designed to inflate and press against lumen wall (1450). According to some embodiments, a catheter may include more than one ultrasound emitting element, some of which are directional, and configured to emit ultrasound beams at defined directions. Ultrasound imaging element (1412) may be configured to enable obtaining ultrasound imagery of lumen wall (1450) or other bodily organs of interest. According to come embodiments, directional ultrasound emitting elements (1406) have ultrasound emitting sections (1420) and ultrasound blocking sections (1422). The locations of ultrasound emitting sections (1420) and ultrasound blocking sections (1422) determine the direction of ultrasound beams emitted from directional ultrasound emitting elements (1406).

According to some embodiments, after obtaining ultrasound imagery from ultrasound imaging element (1412), catheter (1404) and/or array of directional ultrasound emitting elements (1406) are rotated to a certain desired orientation such that ultrasound beams are emitted at a desired target and avoid beaming on other organs.

According to some embodiments, ultrasound imaging element (1412) is configured to provide a circle view, part of a circle, arrays that provide a circle view and/or arrays that provide a partial circular view.

According to some embodiments, the array of directional ultrasound emitting elements comprises multiple directional ultrasound emitting elements oriented for emitting ultrasound beams at the same direction/target-area. According to some embodiments, the array of directional ultrasound emitting elements comprises multiple directional ultrasound emitting elements, at least some of which are oriented for emitting ultrasound beams at different directions/target-areas.

According to some embodiments, the ultrasound transducer is configured to emit ultrasound beams in a full circular range of 360 degrees around the transducer. According to some embodiments, the ultrasound transducer is configured to emit ultrasound beams in a portion of a circular range around the transducer. According to some embodiments, the ultrasound transducer is configured to emit ultrasound beams in multiple portions of a circular range around the transducer.

According to some embodiments, the balloon may be inflated with saline. According to some embodiments, the balloon may be inflated with water.

Figure 14B:
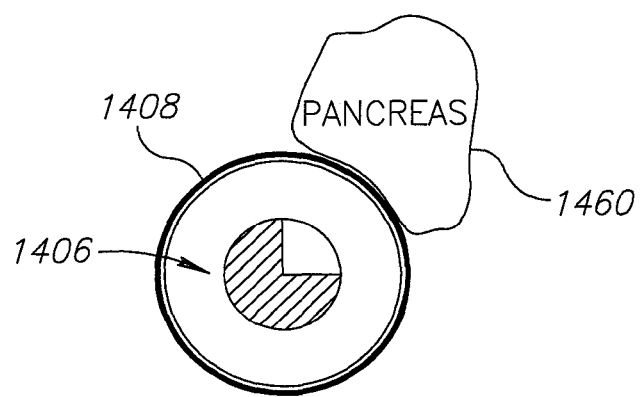
FIG. 14B schematically illustrates a lateral cross section of a catheter with an array of directional ultrasound emitting elements, an ultrasound imaging element and a surrounding balloon, according to some embodiments.

FIG. 14B schematically illustrates a lateral cross section of one of the directional ultrasound emitting elements (1406) of catheter (1404) (of FIG. 14A) having ultrasound emitting section (1420) and ultrasound blocking section (1422) and surrounding balloon (1408), according to some embodiments. Directional ultrasound emitting elements (1406) are oriented for emitting ultrasound beams without targeting a pancreas (1460) of a subject.

According to some embodiments, the imaging ultrasound is configured to provide ultrasound imagery of a full surrounding range of the catheter. According to some embodiments, the imaging ultrasound is configured to provide ultrasound imagery of a partial surrounding range of the catheter.

According to some embodiments, the energy and/or time of exposure and/or frequency of any one or combination of the ultrasound emitters/transducers and/or laser(s) may vary according to the organ and the surroundings thereof. In some embodiments, energy may be transmitted to a selected area, such as the interface of the duodenum with extrinsic nerves that constitute the VANs and other neural projections within the gastrointestinal mesentery, with the objective to impact the nerves that deliver information externally (extrinsic system) to the brain, spine or pancreas, by elevation of the temperature that will induce selective thermal ablation of the nerves in a manner that does not significantly impair blood supply so that the blood flow may cool it while the ultrasound beam elevates the temperature in surrounding and thus selectively ablate the extrinsic nerves with minimal collateral damage to the nerve surrounding tissue(s).

Figure 15:
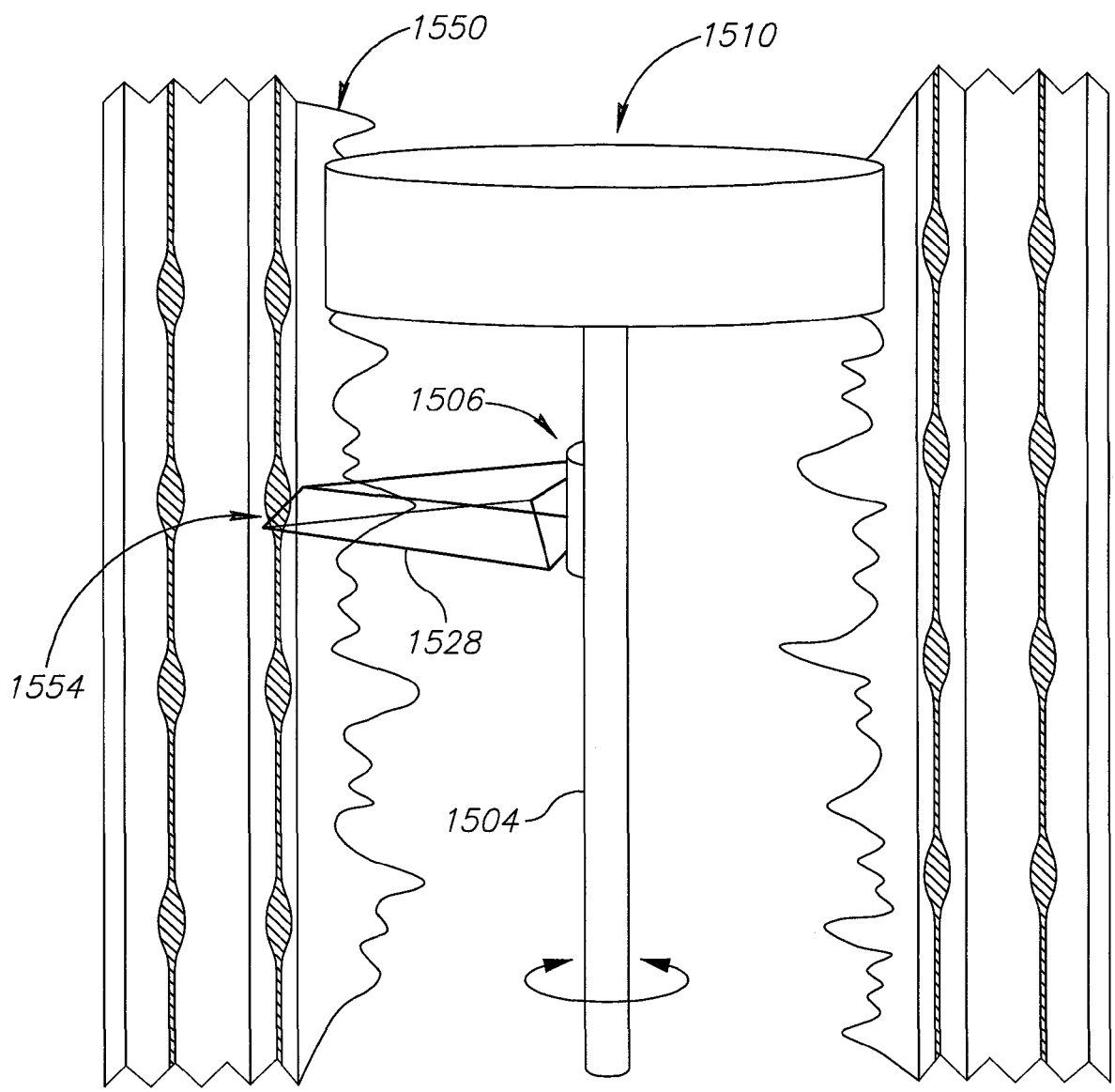
FIG. 15 schematically illustrates a catheter with a focused unidirectional ultrasound emitting element and a distal balloon, according to some embodiments.

FIG. 15 schematically illustrates a catheter (1504) with a focused unidirectional ultrasound emitting element (1506) and a distal balloon (1510) filled with saline, according to some embodiments. Distal balloon (1510) is configured to position catheter (1504) and/or unidirectional ultrasound emitting element (1506) in a desired location between lumen walls (1550). Unidirectional ultrasound emitting element (1506) is configured to emit an ultrasound beam (1528) that converts in a predetermined direction to target a desired area (1554), and may behave differently in other directions. According to some embodiments, focused unidirectional ultrasound emitting element (1506) is perpendicular to lumen wall (1550).

According to some embodiments, the acoustic energy may be delivered by focusing at least one beam of relatively intense ultrasound on the region. The high intensity, focused ultrasound, conventionally referred to by the acronym "HIFU", may generate thermal stress and/or cavitation that may selectively disrupt or destroy a tissue of interest within a target area. According to some embodiments, tissue, such as nerve structures, raised to and maintained at a temperature above about 42° Celsius, for example, may be modulated/damaged and mechanical stresses generated by cavitation may breach and tear cell membranes of that tissue.

According to some embodiments, the ultrasound transducer may be capable of focusing two or more different frequencies into a single focal target/zone/area.

According to some embodiments, the ultrasound transducer may be capable of generating an intensity pattern for example, by a plurality of elements independently capable of radiating acoustic energy.

According to some embodiments, the ultrasound transducer may further include a controller configured to simultaneously activate some of the elements while leaving at least one element inactivated and thus control/change the intensity pattern within the target area.

According to some embodiments, the ultrasound transducer may me spherically shaped. According to some embodiments, the transducer may include an array of transducers. According to some embodiments, the array of transducers is electronically or mechanically controlled for manipulating the emitted ultrasound beam for compensating for/dealing with aberration associated with the lumen wall or other tissue structures.

X. PHOTODYNAMIC THERAPY (PDT)

According to another aspect, the present disclosure provides methods and systems for selectively blocking at least part of the neural activity in a target area within at least part of an organ of a subject, such as a subject's duodenum and/or the duodenal wall or in contact with the duodenal wall by using photodynamic therapy (PDT) to cause damage to neurons, typically sensory neurons, within the target area while maintaining functional activity of tissue surrounding the neurons and/or surrounding the target area. Each possibility represents a separate embodiment of the present disclosure.

According to some embodiments, conventional photodynamic therapy (PDT) is used. Conventional photodynamic therapy (PDT) is based on the accumulation of a photosensitizer in a specific tissue to produce phototoxicity with minimal damage to surrounding tissue (Dougherty et al. J Natl Cancer Inst 90:889-905, 1998). Traditionally, PDT is thought to be mediated by the generation of ROS, especially singlet oxygen, in the presence of oxygen (Dougherty et al. J Natl Cancer Inst 90:889-905, 1998).

In vivo investigation of PDT in experimental gastrointestinal neoplasms has demonstrated important biological advantages. Full thickness intestinal damage produced by PDT, unlike thermal damage, does not reduce the mechanical strength of the bowel wall or cause perforation, because the sub-mucosal collagen is preserved.

According to some embodiments, PDT comprises illuminating a tissue comprising a photosensitizer material which had been administered to the subject systemically or locally with a light source configured to emit light which is configured to induce the photosensitizer to induce damage. Each possibility represents a separate embodiment of the present disclosure. According to some embodiments, PDT induces damage to tissue comprising a photosensitizer while inducing no damage or non-significant damage to the surrounding tissue. Each possibility represents a separate embodiment of the present disclosure. According to some embodiments, the damage is cytotoxic damage. According to some embodiments, the photosensitizer is promoted to an excited state upon absorption light to induce generation of reactive oxygen species, such as, but not limited to, singlet oxygen, thus inducing cytotoxic damage. According to some embodiments, a light source configured to emit light which is configured to induce a photosensitizer to induce damage is a laser source, such as, but not limited to diode lasers, He—Ne laser & argon laser. According to some embodiments, a light source may include a light emitting device, emitting light at a therapeutic window, such as but not limited to: 600-900 nm wavelength. According to some embodiments, a light source may include a fluorescent bulb to induce damage. According to some embodiments, a light source may include a Xenon lamp to induce damage.

According to some embodiments, a photosensitizer is a material configured to induce damage when exposed to visible light. According to some embodiments, a photosensitizer is a phototoxic material. According to some embodiments, the photosensitizer is selected from the group consisting of: methylene blue, toluidine blue, janus green B, protoporphyrin IX, hematoporphyrin, chlorin e6, chlorin p6, m-tetrahydroxyphenylchlorin, riboflavin, acridine orange, sulphonated zinc, sulfonated aluminum, phthalocyanine derivatives, phosphonated aluminum phthalocyanine, Pd-bacteriophephorbide, 2-[1-hexyloxyethyl]-2-devinyl pyropheophorbide-alpha, motexafin lutetium, azure-C, phenothiazine derivatives, aminolevulinic acid derivatives, porfimer sodium, verteporfin azadipyrromethenes derivatives, porphyrin derivatives, and haematoporphyrin derivatives and a combination thereof. Each possibility represents a separate embodiment of the present disclosure. According to certain embodiments, the photosensitizer comprises nanoparticles. According to some embodiments, the nanoparticles are used as carries thus increasing the photosensitizers' aqueous solubility, bioavailability and stability. According to non-limiting examples, the nanoparticles include, but are not limited to: colloid gold, quantum dots, paramagnetic nanoparticles, silica-based nanoparticles, polymer-based nanoparticles and a combination thereof. Each possibility represents a separate embodiment of the present invention. According to some embodiments, the nano-particles are introduced into the duodenal wall endoluminally.

According to some embodiments the photosensitizer comprises liposomes. According to some embodiments the liposomes are targeted liposomes. According to some embodiments the liposomes are administered to the subject systemically or locally. According to some embodiments, the liposomes are targeted to the small intestine, typically to the duodenum. Each possibility represents a separate embodiment of the present disclosure. According to some embodiments, the liposomes are targeted to neurons. According to some embodiments, the liposomes are targeted to sensory neurons. According to certain embodiments the liposome are passively targeted liposomes, actively targeted liposomes, or a combination thereof. Each possibility represents a separate embodiment of the present disclosure. According to some embodiments, actively targeted liposomes are antibody-modified liposomes or ligand-modified liposomes. Each possibility represents a separate embodiment of the present disclosure. According to certain embodiments at least one photosensitizer encapsulated in liposomes is released during or before the treated tissue is irradiated. Each possibility represents a separate embodiment of the present invention. According to certain embodiments the liposomes are thermo-sensitive liposomes, fusogenic liposomes, pH-sensitive liposomes, light-sensitive liposomes or a combination thereof. Each possibility represents a separate embodiment of the present disclosure. According to some embodiments, the liposomes are introduced into the duodenal wall endoluminally.

According to some embodiments, the disclosed methods comprise introducing at least one photosensitizer to at least one layer of the duodenal wall and/or to an area in contact with the duodenal wall. Each possibility represents a separate embodiment of the present disclosure.

According to some embodiments, at least one photosensitizer is introduced to at least one layer or the duodenal wall and/or to an area in contact with the duodenal wall. Each possibility represents a separate embodiment of the present disclosure. According to some embodiments, at least one photosensitizer is introduced to or proximal to the submucosal layer and/or the tunica muscularis layer of the duodenal wall. Each possibility represents a separate embodiment of the present disclosure. According to some embodiments, the at least one photosensitizer is introduced to at least one target area comprising neurons. According to some embodiments, the at least one photosensitizer is introduced to at least one target area comprising sensory neurons. According to some embodiments, the at least one photosensitizer is introduced by injection and/or micro-injection and/or micro infusion. Each possibility represents a separate embodiment of the present disclosure. Introduction of at least one photosensitizer to at least one layer or the duodenal wall may enable to induce selective damage to the at least one duodenal layer following illumination of the layer with suitable light. According to some embodiments, the disclosed methods further comprise introduction of at least one photosensitizer to the target area. According to some embodiments, the disclosed methods further comprise introduction of at least one photosensitizer conjugated to an antibody or antigen binding fragment to the target area. According to some embodiments, the disclosed methods further comprise introduction of at least one photosensitizer to the target area and irradiation of the target area with light which is configured to induce the photosensitizer to induce damage. According to some embodiments, the photosensitizer is conjugated to an antibody or an antigen binding fragment. Each possibility represents a separate embodiment of the present disclosure.

According to some embodiments, the present disclosure provides methods and systems for selectively blocking at least part of the neural activity in a target area within the duodenal wall or in contact with the duodenal wall by using targeted photodynamic therapy or photoimmuno-therapy (PIT) to cause selective damage to neurons within the target area, preferably sensory neurons, while maintaining functional activity of tissue surrounding the neurons and/or surrounding the target area. Each possibility represents a separate embodiment of the present disclosure.

According to some embodiments, the present disclosure provides methods and systems for selectively blocking at least part of the neural activity in a target area of at least part of an organ of a subject, such as a subject's duodenum and/or within the duodenal wall or in contact with the duodenal wall by using targeted photodynamic therapy or photoimmuno-therapy (PIT) to cause selective damage to neurons within the target area, preferably sensory neurons, while maintaining functional activity of tissue surrounding the neurons and/or surrounding the target area. Each possibility represents a separate embodiment of the present disclosure.

According to some embodiments, photoimmuno-therapy (PIT) relates to photodynamic therapy further comprising coupling and/or connecting at least one photosensitizer to an antibody or antigen-binding fragments such as, but not limited to, Fab fragments, Fab' fragments, F(ab')$_2$ fragments, single-chain Fv fragments (scFvs) or a combination thereof to yield a conjugate. Each possibility represents a separate embodiment of the present disclosure. According to some embodiments, the at least one photosensitizer is coupled with and/or connected to an antibody or antigen-binding fragment. Each possibility represents a separate embodiment of the present disclosure.

According to some embodiments, antigen-binding fragments of antibodies include, but are not limited to, Fab fragments, Fab' fragments, F(ab')2 fragments, and single chain Fv fragments. According to some embodiments, a photosensitizer coupled, connected or conjugated to an antibody or antigen-binding fragment retains the photosensitizing effects of said photosensitizer and the binding properties of the antibody or antigen binding fragment. Each possibility represents a separate embodiment of the present disclosure. According to some embodiments the at least one photosensitizer is coupled with and/or connected to an antibody or antigen-binding fragment via at least one linker, such linkers are known to those skilled in the art.

According to some embodiments, the antibody or antigen-binding fragment binds specifically to neurons. According to some embodiments, the antibody or antigen-binding fragment binds specifically to neurons and/or nerve fibers and/or synapses. Each possibility represents a separate embodiment of the present disclosure. According to some embodiments, the at least one photosensitizer is conjugated to an antibody or antigen binding fragment configured to specifically bind neuronal tissue by targeting neuronal elements such as, but not limited to: myelin basic protein, neurofilaments, choline acetyltransferase and Protein Gene Product 9.5 (PGP 9.5). Each possibility represents a separate embodiment of the present disclosure.

According to some embodiments, the antibody or antigen-binding fragment binds specifically to sensory neurons rather than motor neurons. According to certain embodiments a photosensitizer-antibody conjugate comprises an antibody or fragment thereof that targets sensory or afferent neural elements. According to non-limiting examples, the antibody or antigen binding fragment may be configured to bind antigens such as, but not limited to: Acid sensing ion channel 3 (ASIC3), Acid sensing ion channel 1 (ASIC1), Calcitonin gene related peptide (CGRP), Tyrosine hydroxylase, Substance P, Neuropeptide Y (NPY), 5HT3-receptor, P2X3, CaV channel. K+ channel, NaV channel, Transient Receptor Potential Vanilloid (TRPV) channel, Transient receptor potential cation channel subfamily M member 8 (TRPM8), Transient receptor potential cation channel subfamily A member 1 (TRPA1), Transient receptor potential cation channel subfamily C member 6 (TRPC6), Vesicular Glutamate Transporter 1 and 2 (VGLUT1/2) and Parvalbumin. Without wishing to be bound by any theory or mechanism, introducing at least one photosensitizer bound to a neural-specific antibody into at least one layer of the duodenal wall enables selectively causing damage to neurons within target areas illuminated with light suitable for PDT or PIT.

According to some embodiments, the disclosed method further comprises introducing into at least one layer of the duodenal wall and/or an area in contact with the duodenal wall at least one photosensitizer configured to induce damage to a target area when illuminated with a PDT-compatible light source.

According to some embodiments, the present disclosure provides a method for blocking at least part of the neural activity in a duodenum of a subject in need thereof, the method comprising:
introducing at least one photosensitizer to a target area within or in contact with at least part of a duodenal wall, wherein the target area comprises neurons, typically sensory neurons, and wherein said photosensitizer is configured to selectively cause damage to said target area when receiving radiation, typically laser radiation;
introducing at least one radiation emitting element, typically a laser element, into a lumen of the subject's duodenum;
actuating the radiation emitting element to emit radiation, such as, but not limited to, laser radiation, wherein said radiation is configured to induce said photosensitizer to cause damage;
focusing the radiation to said target area, thereby causing damage within the target area while maintaining functional activity of tissue surrounding the target area. Each possibility represents a separate embodiment of the present invention.

According to some embodiments, the present disclosure provides a method for blocking at least part of the neural activity in a duodenum of a subject in need thereof, the method comprising:
introducing to a target area within or in contact with at least part of a duodenal wall at least one photosensitizer configured to selectively bind and/or enter neurons, wherein the target area comprises sensory nerves, and wherein said photosensitizer is configured to selectively cause damage to said target area when receiving laser radiation;
introducing at least one laser element into a lumen of the subject's duodenum;
actuating the laser element to emit laser radiation, wherein said laser radiation is configured to induce said photosensitizer to cause damage;
focusing the laser radiation to said target area, thereby causing damage to neurons within the target area while maintaining functional activity of tissue surrounding said neurons.

XI. PIGMENTS AND PHOTOSENSITIZER

According to some embodiments, the disclosed methods comprise introducing at least one pigment to at least one layer of at least part of an organ, such as the duodenum and/or the duodenal wall and/or to an area in contact with the duodenal wall. Each possibility represents a separate embodiment of the present disclosure. According to some embodiments, the pigment is configured to have higher light and/or energy absorbance than the tissue to which it is introduced. Each possibility represents a separate embodiment of the present disclosure. According to some embodiments, the at least one pigment is introduced together with at least one photosensitizer. Without wishing to be bound by any theory or mechanism, introduction of a pigment into a tissue such that the pigment has higher absorbance than the tissue enhances the ratio between the impact of the laser radiation applied to the tissue and the lateral energy absorption of the tissue. According to some embodiments, the pigment enhances the energy absorbance of the target area to which it is introduced. According to some embodiments, the pigment is coupled with and/or connected to an antibody, an antibody fragment or an antigen binding fragment. Each possibility represents a separate embodiment of the present disclosure. According to some embodiments, the pigment is nanoparticle or liposome encapsulated. Each possibility represents a separate embodiment of the present disclosure.

According to some embodiments, the disclosed method further comprises introducing into at least one layer of the duodenal wall and/or an area in contact with the duodenal wall at least one pigment. According to some embodiments, the disclosed method further comprises introducing into at least one layer of the duodenal wall and/or an area in contact with the duodenal wall at least one pigment having higher absorbance than that of the tissue to which it is introduced.

A non-limiting example of a pigment which may be used according to the present disclosure is a Squaraine dye with a peak of absorption at about 630 nm. According to some embodiments, the pigment is configured to enable safe use and absorption in the near infra-red spectrum. According to some embodiments, the pigment may be designed to enable safe use and absorption in the near infra-red spectrum using methods such as, but not limited to, the Pariser-Pam-Pople molecular orbital method for the identification of near-infrared absorbing pigment candidates. According to some embodiments, Squaraine dye with a peak of absorption at about 630 nm may be used as a photosensitizer.

According to some embodiments, the blocking of the signals triggered by food, either by chemical sensors or mechanical sensors, may also modulate motility related functions of the GI tract organs, such as modulation of gastric accommodation and relaxation triggered by meal passing through the duodenum and/or stomach based on the principles in the prior art or direct impact on motility of a specific site. Each possibility represents a separate embodiment of the present disclosure.

Embodiments herein presented and similar can be used in other endoluminal applications that require impact of nerves surrounding the lumen, such as impact, damage, injury of nerves surrounding vessels as in renal denervation. The motivation for using these embodiments instead of the conventional RF based catheters is to enable more effective impact on nerves with minimization of lateral damage.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

What is claimed is:

1. A method for reducing neural activity in a duodenum of a subject, the method comprising:
    introducing at least one laser emitting device comprising a cooling mechanism into the duodenum;
    emitting a laser beam, at an intensity in the range of a 100 mW-10 W, from the laser emitting device to a target area in the duodenum, wherein the laser beam is configured to be absorbed by the different layers of the duodenum in the target area; wherein the laser beam has enough linear optical absorption to elevate tissue temperature at a focal plane of the laser beam to 45° C.-75° C.; and
    lowering a temperature of the target area using the cooling mechanism, thereby selectively ablating sensory nerves located in the target area's submucosal layer to at least partially reduce the neural activity within the submucosal layer while maintaining functional activity of the mucosal layer within the treated target area and/or surrounding the target area.

2. The method of claim 1, wherein the sensory nerves comprise at least one nerve that is activated by food passing through the duodenum; and/or wherein the sensory nerves comprise at least one nerve that transmits signals from at least one of mechano-sensors or chemo-receptors located within the duodenal wall.

3. The method of claim 1, wherein the laser emitting device comprises a rotatable optical element configured to direct the laser beam to a plurality of target areas along a trajectory on or within the duodenal wall.

4. The method of claim 3, wherein the rotatable optical element is selected from a group consisting of a wide-angle lens, a dove prism, a reversion or "K" prism, a Delta or Pechan prism, a dispersive prism, a reflective prism, a beam-splitting prism, a deflective prism, a triangular prism, a trapezoidal prism, a Glan-Taylor prism or a Glan-laser prism, a high-powered laser-light right angle prism, a retroreflector and combinations thereof.

5. The method of claim 1, wherein the cooling mechanism comprises infusion, irrigation or rinsing of tissue surrounding sensory nerves with a coolant material.

6. The method of claim 1, wherein emitting the laser beam comprises emitting pulsed laser radiation.

7. The method of claim 1, wherein said subject is afflicted with a medical condition selected from the group consisting of obesity, type 2 diabetes, insulin resistance, metabolic syndrome, and combinations thereof.

8. The method of claim 1, wherein the cooling mechanism is configured to lower the temperature of target area in the path of the laser beam's energy transfer.

9. The method of claim 1, wherein the laser beam has a wavelength of 808 nm-980 nm.

* * * * *